United States Patent
Helmann et al.

(10) Patent No.: US 7,309,484 B2
(45) Date of Patent: Dec. 18, 2007

(54) COMPOSITIONS AND METHODS FOR SCREENING ANTIBACTERIAL COMPOUNDS

(75) Inventors: John D. Helmann, Ithaca, NY (US); Thorsten Mascher, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/875,100

(22) Filed: Jun. 23, 2004

(65) Prior Publication Data

US 2005/0186653 A1    Aug. 25, 2005

Related U.S. Application Data

(60) Provisional application No. 60/480,649, filed on Jun. 23, 2003.

(51) Int. Cl.
*A61K 38/51* (2006.01)
*A61K 38/00* (2006.01)
*C12N 9/12* (2006.01)

(52) U.S. Cl. ............... 424/94.5; 514/12; 435/194
(58) Field of Classification Search ............ 435/15, 435/194, 252.3, 320.1; 424/94.5
See application file for complete search history.

(56) References Cited

OTHER PUBLICATIONS

Cao & Helmann et al., J. Bactereiology, 184(22), 6123-6129, 2002.*

\* cited by examiner

*Primary Examiner*—Maryam Monshipouri
(74) *Attorney, Agent, or Firm*—Burns & Levinson, LLP; Janine M. Susan; Jacob N. Erlich, Esq.

(57) ABSTRACT

The present invention pertains to compositions and methods used to ascertain if putative antibiotics trigger a cell envelope stress response in bacterial organisms. In one aspect of the invention, three two-component systems are described: LiaR & LiaS (formerly YvqCE); YvcP & YvcQ; and BceR & BceS (formerly YtsAB). These systems, for example, can be used to analyze antibiotics such as vancomycin, bacitracin, nisin, and ramoplanin, which interfere with the lipid II cycle in the cytoplasmic membrane.

7 Claims, 21 Drawing Sheets

Figure 5
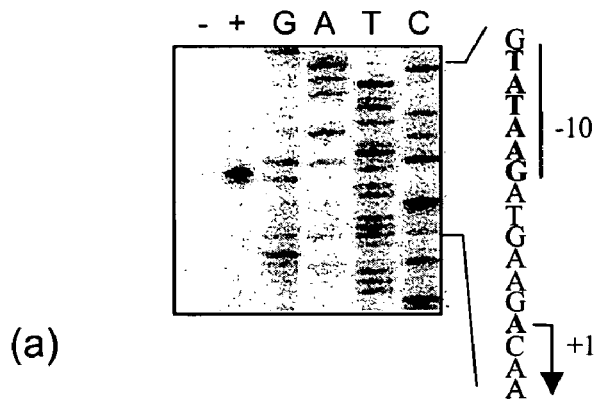
(a)
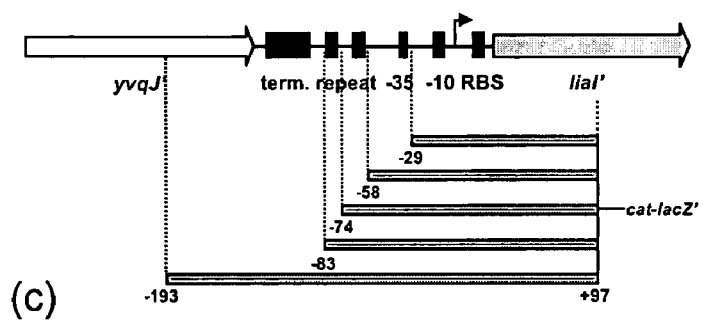
(b)
(c)
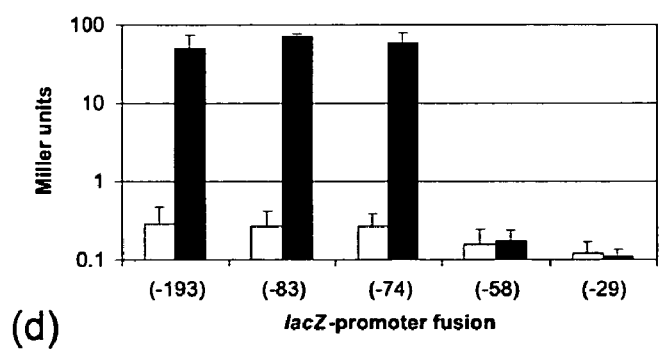
(d)

Figure 6
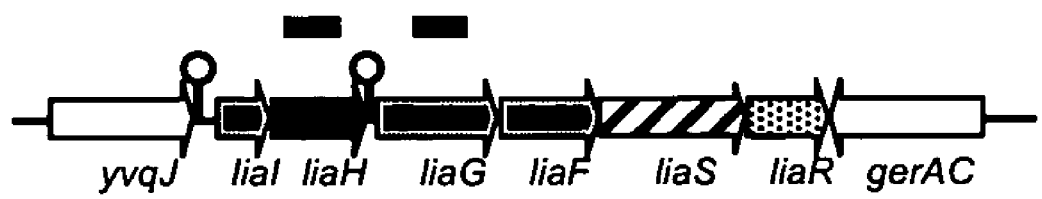
(a)
*liaH*   *liaG*
 −   +   −   +
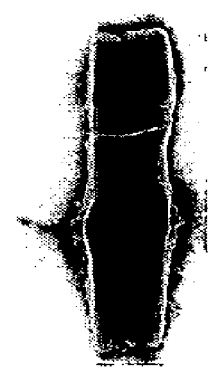
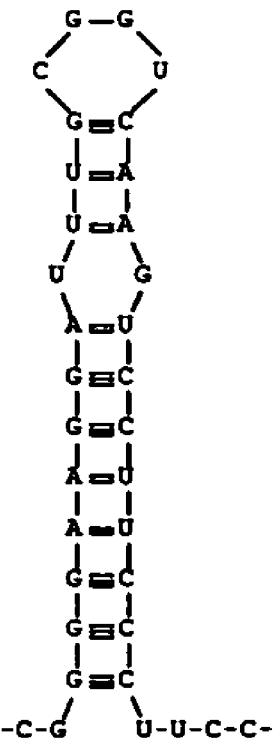
◄ ~4
◄ 1.1
(b)             (c)

```
BA1956      1  MSKFKMLKVTGAIIALFS------FLTIIWSTA----------------------FYVSS 32
BC1801      1  ------------------MKIKSLQG----------------------IRAKF 13
BC1957      1  ---MKMLKVFGAVLALFS------ILTIIWSTA----------------------FYVAT 29
BH3912      1  -----------------MIKTFIK----------------------ERGSW 12
BH2700      1  -----------------MFRTVFIAFIK----------------------DRSLF 16
BH0289      1  -----------------MRGIKQIYDCIY----------------------AYKLG 17
BH0272      1  -----------------MKLFIK----------------------DHLSF 11
BH1199      1  -----------MKKRRRLAQLQIQFIR----------------------NSLIV 21
BliBacS     1  -----------------MRKMIT----------------------DKKLL 11
BsuYtsB     1  -----------------MIKAFII----------------------ERRSW 12
BsuYvqE     1  -------------MRKKMLASLQIRAIR----------------------MTTGI 20
BsuYvcQ     1  -----------------MIKTYII----------------------DRLAI 12
BsuYbdK     1  ---------------MLLFTAVIS----------------------VPMLLL 15
CAC3516     1  -----------------MKIRIKI----------------------LLFLVMF 15
CAC1517     1  -----------------MNFRAIVK----------------------DRMAY 13
CAC0372     1  ---------------MYKKIIKNFMK----------------------EKLSY 16
CAC0225     1  ---------------MSFIRNIK----------------------DNFRF 13
CPE0841     1  -----------MKIRDIFE----------------------DKTFF 13
EF0927      1  -----------------MIILKVIK----------------------DRWLL 13
Lsa HPK1    1  -----------------MIFKKIIR----------------------DHLFH 13
LMO1741     1  -----------------MNWWSILK----------------------DKRFF 13
Sau MW0622  1  ---------------MNNLKWIAYIK----------------------SRMNW 17
SA2417      1  -----------------MTIIK----------------------SITQE 10
SA0615      1  ---------------MNNLKWIAYIK----------------------SRMNW 17
Sau SaeS    1  ------------MLSIRSQIIIG----------------------VVSS 15
SE2194      1  -----------------MKFAIIQ----------------------SIRNE 12
SE0428      1  -----------MNNFRWFWFIIK----------------------SRINW 17
GBS0964     1  -----------------MIRQIIR----------------------EHLIW 12
GBS0430     1  -----------------MKIKYIIV----------------------IGYLI 13
GBS0122     1  ---MTKLRRFRFPLRFYF------TLMFVLTIML----------------------FSVLA 29
SmuMbrD     1  -----------------MIRSIIR----------------------EYSIW 12
SP1632      1  -----------------MKIKSIIL----------------------VGYII 13
SP0084      1  -------------MLDWKQFFLAIIR----------------------SR-SR 17
BL1001      1  --MMASKKQQQSRLDAMK----PRVKFIDLISS----------------------LKLEL 32
SAV2971     1  ---MSDG--PAARRGPG-----DPWGGIRPIS----------------------IKTKL 27
SAV7391     1  --------MGVMTDGRGRRRAERLVGAAAIPRSGKEGTPREHRGTPTGGDKRSVSLFR 51
SCO5282     1  ---MSSRGREAARRNPGPRTTGEPWGGIRPIS----------------------IKTKL 34
SCO6424     1  ----------MARVPDAAAVP----------------------LFW 14
SCO5784     1  --------MGVVTDIRSRSRSAKIAAGVSCEKAG--------R------SGKRNVSLFW 37
SCO6163     1  ---MHATFLIALYAFAGAAAAGLVGAAILRLIRR----------------------RSLTA 36
ALR3155     1  ---------------MISMEIST----------------------ITEY 12
HaeArcB     1  ---------------MKNFKYIAQ----------------------SYVD 13
RS03089     1  -----------------MKLPVGRLIIK----------------------CFAVL 16
XneEnvZ     1  --------------MRRLWLSICALCIR----------------------ILSVM 19
TM1258      1  -----------------MRVIELED----------------------LDHIR 13
```

FIG. 10

```
                    Transmembrane Helix 1        Transmembrane Helix 2

BA1956      33  SILDALAIHLSPFVTYLISDIL---------SFIFMILVWILIAVLMRPKRE---------  75
BC1801      14  FIAFICSIFLAIVSIIVFQILIG----NIYSHVTALEEKYSFLYFIVFLIFTTTYFAFMT  69
BC1957      30  SLLNAFDVNVSPFVAFLISDMV---------GVVFIILIWTLIGILVRPKRE---------  72
BH3912      13  ILIIIFLQCFTVFIAYLDSAIP----LAP--VFYSVFLSSMIFLFFLAVRYKKETTFY---  64
BH2700      17  SLFYFLGVGSVLLFFYISHPAQS------BIMYPTLIACFLYILYLLIEWSKYGHFHR--  68
BH0289      18  FLLLIITNLIFIFFAWLAYPET--------PKVLVGLMIVFTIATISLSIFIIVRKQ---  66
BH0272      12  ILLYLITFICLPFIIEQLDGFEN------HYDYFSFIAITLLMSLLVIRYLRRKKMY---  62
BH1199      22  SFFAVLFTVVIMTYDDIAGLTMLFDKQIVRLPILVFITLLSMIAIGLIACMMQSLPIKRKL  81
BliBacS     12  LLIIQCAAIAALLFIYMKTAS---------LGVFSTMLFIFLFAVTALIETMRLRFIDRL  62
BsuYtsB     13  IAAFLFQQALMLFIAFVDPSIS----FGN--VLYMVYLCTLFFIIFLWFRVRKETAFY---  64
BsuYvqE     21  SLLLFVCLASFMMFYYRLDPLVLLSSSWFGIPFIEILLLISVTVGFASGYMYGNRLKTRI  80
BsuYvcQ     13  ILFSLLGIGSAMLIAYLSIVESGAEPSKENMMYEWILPGTLLAAGFAADYVRQFSFLTYV  72
BsuYbdK     16  AVSVLMSVIYDSMFKPMNHGMP-----PHRSFAYPAMLVVFLISLILIAFLFSKSIH---  67
CAC3516     16  IVFMVSIGLYLKFIFALYSPISGSLLNSSSIGLLFPIFAIACEIFVLIMYIY-FFIE--  72
CAC1517     14  IVVYGLSTVLAILIMNLTSIINRVYISGINILYAFLISAIFLIVFLMYDYYKNKKFYN--  71
CAC0372     17  SISFFLSSGIILFYFYVSKNIT--------DVVYPIFMVMSIYIIFIVTEWFKYYRFN--  66
CAC0225     14  ILLYVLLGAFVSAFTYLDEKNR---MLSSNIGYMIFVMFFILLLFPCVLYSIKN------  64
CPE0841     14  LIVNFIIFATIGVLLFIG--N----VGSGIIFLIGCFWFIPLFTYIILDPYKSKKFY---  64
EF0927      14  LIGWLFFLFITCFILWLAPNVR---LDWTVVGYIFLLQSVFLSIFLTIDYYLRKKWW---  67
Lsa HPK1    14  IVFFFGGMFVLDIVLWLDPHMR---LAKETIMYLDFILTIFFCAFLIGLYLHRKWF---  67
LMO1741     14  LLFFCSIMFFVGVLISEDPNSK---LTLGNFIYLYVFVLVFLLSYLVLGYFFKYSYW---  67
Sau MW0622  18  IFWIIFLNLIMLGISLLDYDFP----IDS--LFYVSLNLSLTMIFLLITYFKEVKLY---  69
SA2417      11  IAVVIVIIFALPGLMFYLYHLP---------LEAYLLALGVILLLLLIFIGIKYLSF--  57
SA0615      18  IFWILFLNLIMLGISLLDYDFP----IDS--LFYIVSINISLTMIFLLITYFKEVKLY---  69
Sau SaeS    16  IPLTSTILAIAYILMWFNGHMT--------IPLTLTTIITSCLTLLICSIFINILIQ---  64
SE2194      13  ISIIIIIILFFALIFYVFSLP---------FDAYVLAISILLLMCVRWTIKYLSF---  59
SE0428      18  ILWIIFLNEILLGVAYIDYEIS----VES--VFYIVILNVGLSIILFLLFTIVKEVRLS---  69
GBS0964     13  YILYIMMFVLFFISFYLYHLP--------MPYLFNSLGLNVIVLLGISIWQYSRYR---  60
GBS0430     14  SMLITVAGVFFGLNHMLIETRG--------VYYIILSVTIACIVGGIVNLFLLSSVF---  62
GBS0122     30  SLLLVAAIVFTFFQGVLTTHVL--------QVSALAVVFLSLVIASISMMYGSYHLT---  78
SmuMbrD     13  YLNYAIVSLAFLLTFYLYHLP--------LVYFINSLILSLTLDLITSLILYWRFH---  60
SP1632      14  STLLTILVVFWAVQKMLIAKGE--------IYFLLGMTIVASLVGAGESLFLLLPVF---  62
SP0084      18  LFIYELSLAFLVLLFQFLFAS---------LGIYFLYFFFICCFVTPLFPTWDILV---  64
BL1001      33  SALEVIATAIAFAMCWFLLKFG--------WSGWIAMPLTLVVALGITYFFSRG-IT---  80
SAV2971     28  GALVVISVLITTGLSMIAVHTK--------TELRFITVFSMIATLLITQFVAHS-LT---  75
SAV7391     52  RIFLLNAVGLTVATALLLGPVTVSTPVLPGEALVVLAGIAVMLVVNAVVLWIGLAPLQRL  111
SCO5282     35  GALVVTSVLITTGLSVIAVHTK--------TELRFITVFSMIATLLITQFVAHS-LT---  82
SCO6424     15  RISIFNSVVLIAATALILGPVTVSTPVLLTEAAILTAGLVVILIANILLRIGFGELROL  74
SCO5784     38  RIFSLNAAGEVVATALLLGPVTVSTPVLAGEALVAGLAALIAGNAVVLRIGLTPLHRL  97
SCO6163     37  SLAVVAAVAVLAMLAGTLAVAWAMFLSPHDLSVVPTIVVAMAAVVSIATALLLGRWVARS  96
ALR3155     13  VFGYLYTGPILLANHWFGR----------IATLLTTFIAVFLTIPNLGEPNNEVIR---  58
HaeArcB     14  WVIRLGRLRFSLLGVMILAVLA--------LCTQILFSLFIVHQISWVDIFRSVTFG---  62
RS03089     17  WLAMVAAFVCAGLYLRLTGHPP---PPSEPRWFFLIPVVSGAAVGLIVAEALAWYLA---  70
XneEnvZ     20  LAMLIGSLLISVLIAQLLTMIET-------LSFDSVFFYIFISWFAASSLVFAAFWR---  69
TM1258      14  EAIVILKGLEVEGANKPGEKLG---------FKKGKNLMSIFTCKEMDRFIR-------  56
```

FIG. 10 (cont.)

```
BA1956       75  -AMIWTIIEPIQK--IAKGDFS------VKIRNEEKYDGEIGVEVKSINDMTD-------  119
BC1801       70  KTLMKRLSQINKNVKEISEGNFEIHIPISKSDEIGELAANVNRMAKSLKESIE-------  122
BC1957       72  -AMIWTIIEPIQK--IAKGDFS------VKIRNEEKYDGEIGVEVKSINDMTD-------  116
BH3912       65  RKLEEWDK-------DLDVTNLAA----AESPFERIIEQTIVKQTGYLQEKAH-------  106
BH2700       68  -QLKKRHAG--------ESRELAP-----KTEEQRVMTELIETVTSDFRRDMS-------  107
BH0289       67  NIEEAAFQEFLLEPNEMNEERLCR----VSPKTIWSCIRDMGSSIRSYQAELN-------  115
BH0272       62  -THEKKEN--------LDQADFLIYR---PHAPIEKAYANQIKEFSSLLLKEQD------  104
BH1199       82  DQIEHGVLLYERGTFSHQIESEGEDELAELTDRLNRMAERVEEQVASLQRLSSERAKMQE  141
BliBacS      63  KLIETELKRVADG--NLRRRLLAK-----GGQPFNEIIFSTNELIEQLEKVQIN------  109
BsuYtsB      65  KSLKTWEN-------NLDVTAINE----PETPFEAMVERSIAGQTEHLKQTAA-------  106
BsuYvqE      81  DTLIESILTFENGNFAYRIPFLGDDEIGLAADQLNEMAKRVELQVASLQKLSNERAEVQA  140
BsuYvcQ      73  KKLAEQAS-SSND--IGQSLKARK----PRTGFQALWTKMINALGQQYESRLS-------  118
BsuYbdK      67  -SIEHKINLLNQT--IRHLASDQRVPDKIEVKRADEIGELIKSVNLLIERTTYR------  118
CAC3516      73  KPEGLLN----TR--LERINIVHP-----LPSLALRSNDEEGDIYNHFNNMEK-------  114
CAC1517      71  -QLDLILK-SEED--LDYMLNIER----GSTLEQEMFRKILLKIYRLSENKTV-------  116
CAC0372      66  ------AN--LTRG--IEREYYDLE----SVTPEQRMAQEAILKIHKNYAAKIS------  106
CAC0225      65  KHEKKLIANGETK--D-KTPILPE----PLEYKDEVYISIIEDLYKDYNERIV-------  110
CPE0841      65  DNESITLDKLDRK--YLLPEVIEE----PNFYHGKFLYEVIKETDKDMHEHVK-------  111
EF0927       68  LSLATEK----EP--PSLQEYLNT----AEKEEELLVQTYINGLLQEHQQTMQ-------  110
Lsa HPK1     68  RTIQIRLN--AKE--DALNWPLTG----ATSAEKQYFQKYVNSLLDYHQQSIE-------  112
LMO1741      68  REMKELVS-GEIE--ENTIELLPK----PRTREQAFFNQLMAKKHKEELRTIS-------  113
Sau MW0622   70  KHFDKDKE-------IEEIKHKDL----AETPFQRHTVDYLYRQISAHKEKVV-------  111
SA2417       58  VKTIS---------------------------QQQQIENLETALYQLKN-----------  79
SA0615       70  KHFDKDKE-------IEEIKHKDL----AETPFQRHTVDYLYRQISAHKEKVV-------  111
Sau SaeS     64  --KIKQFNIKTKP--FANGNYASNDKTFNSPKEIYELNQSFNKMASEITQQMN-------  113
SE2194       60  KKNEH------------------------------LKDKVAYLEHELAHVKN--------  81
SE0428       70  KHFYEDKE-------IEEIKHKDL----AETPFQQQVIDYLYRHIAAQKEKVV-------  111
GBS0964      60  -KKMLHLK-YFNS--SQDP---TF-----ELQPSDYAYFNIITQLEAREAQKVS------  102
GBS0430      62  -TSEKKLKQRMKD--ISQRCFDTK-AQICSPQEFKDLETAFNQVSSELESTFK-------  111
GBS0122      78  -KPILDISRIVSN--VADGDFEGHIYRNSNRRKSYEYYNELDELSESINQMIV-------  128
SmuMbrD      60  -QKIKNLH-HFIY--VKEPRNLTM----LTAPSDLVYKEILKKILQEQSDINL-------  105
SP1632       62  -TSEGKLKEHAKR--VAAKDFPSN-LEVQGPVEFQQLGQTFNEMSIHDLQVSFD------  111
SP0084       65  ETQVYRQE---------LLYGERE----AKSPLEIALAEKLEAREMELYQQRS-------  104
BL1001       80  -APIRQMRDVAEA--MADGDYT------VRVDIDQDRHDEVGKIARSFNEMAG-------  124
SAV2971      75  -APEDDMNTVARS--ISRGDYT------RRVREN--RWDELGDLAHTINLMAD-------  117
SAV7391     112  GRAMATADLLEPG---ARAVVTGFAEMADLTSTYNTMLDRLETERATSAAR---------  159
SCO5282      82  -APEDEMNAVARS--ISHGDYT------RRVREN--RRDELGDLAVTINRMAD-------  124
SCO6424      75  ARAMTTTDLLRPR--VRPKVDGDGEIAELITTFNIMLDRIFAERALSAAR----------  122
SCO5784      98  GRAMSTADLLVPG--TRPEVSGFAEAAQLIATYNTMLDRLQAERAAGAGR----------  145
SCO6163      97  RELAAAAR-SFG----DDGDYAAP--STPATAELDALSRELAATSARLAESRE-------  142
ALR3155      59  FPTVASR-------MIACMSLIVTG---ILSDRLRRSQEAIALTRAKLESQ---------  99
HaeArcB      62  -LITAPFVIYFFTLLVEKLEHSRLDLSSSVNRLENEVAERIAAQKKLSQALEK-------  114
RS03089      70  -KPIHHLSMALRH--AARARFDVR-----VLPLLGSRRDELVBLAREFDHMAA-------  115
XneEnvZ      69  -YIHLQKQSLR----AMQKAALEMGKGRTAASLPETGTLTIRALTGVFNQMSER------  118
TM1258       56  -LVQERK---------NFSLETNAYFFELHSKRFVSLRYLPKKSLLFVNDLT--------  98
```

FIG. 10 (cont.)

H-Box

```
BA1956      119 --ELNAMEKMRQEFVSNVSHEIQSPLTSIKGFARALQDTNLPE-EKRKHYLTIIETETTR 176
BC1801      122 --NEKKSQEMKNEMTSNISHDLRTPVTSLIGYADLLGNKLHSNGEECEQYVSILKRKSYE 180
BC1957      116 --ELNTMEKMRQEFVSNVSHEIQSPLTSIKGFARALQDDNLSE-EKRKHYLTIIETETTR 173
BH3912      106 --RHETALFQEKDDLLAWIHEIKTPLTAMHLIIDRLEDR--T-------IKGQLTYEWMR 155
BH2700      107 --QLHIQNKERLYLVSHWIHQLKTPVSVNELLMDQLLKEETNS-QS-VDLLKRMKRENRG 163
BH0289      115 --EQVMELADYENYIEGWVHEIKKPLSLMTLVLDNRRLE---------MSSLVRHRMLH 163
BH0272      104 --TYQNFLQEQQLLISHAVHQMKTPISVMQLLVQSNQTNDVKS-LG---EWQKVKAECDK 158
BH1199      142 TVKKAAVTEERQRLA--RDLHDAVSQQLFAISMMTAAIKQN--LH-----EATEEVQQQMD 193
BliBacS     109 ---AAKSEAARKRLLSNISHDIRTPLTSIIGYVDALKIGVASSEEEKQEYLNILSKKSNS 166
BsuYtsB     106 --RHRLALENEKDELMAWIHEVKTPLTAMHLIIDRMEEK--A-------LKSQESYEWLR 155
BsuYvqE     141 QMKKSVISEERQRLA--RDLHDAVSQQLFAISMMTSAVLEH--VK-----DADDKTVKRIR 192
BsuYvcQ     118 --QYINQQKQHYTFTNQWVHLMKTPVSVISLMIQEGKNG--TS-SSFPTFLEELEDENER 173
BsuYbdK     119 ELELRQQEELIKKELIQKLRHDINIPLTALRLQLFYLEDQCHG----QAVFESEYQQIEY 173
CAC3516     114 --RLQLAHKEQTDMIAAIAHDLKALTSINGFAELLAMQKGLSENEKQEYYEITQKKSKY 172
CAC1517     116 --KYEKRHKEYIYFVNQWVHQMKTPVSVINLTLQDEINE--DN-R---AVFESISEENEK 168
CAC0372     106 --EIDYKNSDIKYFTSQWIHNMKTPVSVIDLIVQREKEK--LS-G---DVIKNIEEENYK 158
CAC0225     110 --SLEKEFEDNNEFMTAWIHEIKTPIATAKLLLESGEID--S---------QLFMEEIEK 157
CPE0841     111 --KYILEQKEYREYIETWVHEIKTPIASTRLLILENNESE--SS------ENIKKEIKK 159
EF0927      110 --QAINNQQDQKDYIDSWVHEIKVPLAAITLLVQSVEDD--IP-E---KKYYLLENELGK 162
Lsa HPK1    112 --RLMHAQQDQKDFIDGWVHESKVPLAATQLLVESIEDQ--IP-E---EKFNQLIDELVQ 164
LMO1741     113 --KLQDKQQFYHDFILYWVHEVKTPVWASKMLINNPDLN--DT-E---TIFKQIDEELTT 165
Sau MW0622  111 --EQQLQLNMHEQTITEFVHDIKTPVTAMKLLIDQEKNQ--E-------RKQALLYEWSR 160
SA2417       79 --EQIEYKNDVESYFLTWVHQMKTPITAAQLLLERDEP---N-------VVNRVRQEVIQ 127
SA0615      111 --EQQLQLNMHEQTITEFVHDIKTPVTAMKLLIDQEKNQ--E-------RKQALLYEWSR 160
Sau SaeS    113 --QIKSEQQEKTELIQNLAHDLKTPLASIISYSEGERDG--II-TKDHEIKESYDTILKQ 168
SE2194       81 --QQIEYRNDVESYFLTWVHQMKTPITASQLLLERNED---N-------VVNRVRQEIVH 129
SE0428      111 --EQQLQIKNHEQTITEFVHDIKTPVTAMKLLIDQENDD--Q------RKRALLFEWSR 160
GBS0964     102 --ETIEQTNHVALMIKMWSHQMKVPLAAISLMAQTNHLD--PK-E-------VEQQLLK 149
GBS0430     111 --SLNESEREKTMMIAQLSHDIKTPITSIQSTVEGILDGIISE-EEVNYYLNTISRQTNR 168
GBS0122     128 --SLSHMDHMRKDFITNVSHELKTPIAAVANIVELLQDPELDE-ETQSELLGLVKTESLR 185
SmuMbrD     105 --QHKTQEEQLQQLIKLWSHQMKVPISALSLMAQTGHLD--KE-D-------VQRQLLR 152
SP1632      111 --SLEESEREKGLMIAQLSHDIKTEITSIQATVEGILDGIIKE-SEQAHYLATIGRQTER 168
SP0084      104 --KAERKLTDLLDYYTLWVHQIKTPIAASQLLVAEVVDR--Q-------LKQQLEQEIEK 153
BL1001      124 --ELEHADKMRRDMIANVSIELRTPVSALQAMVENMADG--VT-EPTPTNLESILTQTQR 179
SAV2971     117 --ELEAQDRQRKELVANVSIELRTPIAGLRAVLLQLRRVDG--IS-AADPETMRTALKQTER 172
SAV7391     159 --ALSAQERERHRVSQEL-HDEVGQTLAVLLQLRRVAD-----------RAPEGLRAEVR 206
SCO5282     124 --DLEAQDLQRKELVANVSIELRTPIAGLRAVLENIVDG--VT-EADPETMRTALGQTER 179
SCO6424     122 --TLSAQESERHRVAQEL-YDEVGQTLAAVLLDLKRVAD-----------QAPEEVREQLS 169
SCO5784     145 --ALQAQERERHRIAREL-HDEVGQTLAVLLQLKRVAD-----------RVPGELREDVT 192
SCO6163     142 --RERALEASRRELVAWISHDLRTPLAGIRAMSEALEDGVAADPD---RYLRQIRAEVER 197
ALR3155      99 ----EELVRLREDFASTLTHDLKTPLLGAIETLKAVQQEKFGAVS---SAQQPVLATIIR 152
HaeArcB     114 ---LEKNSRDKSTLLATISHEFRTPLNGIVGLSQILLDDELDDLQR--NYLKTINISAVS 169
RS03089     115 --LLQQAAAQHRQLFHDVSHELRSPLARIQAAVGLMQQSPQSG-P---VMAERIAREAER 169
XneEnvZ     118 ---LKLQENDQAVLMAGVSHDLRTPLTRIRIATEMMQGKD----N---FLAESIHRDIEE 168
TM1258       98 --EERTLSEAKLDFVTAVSHELFTPLSASKANVFLLKDIENDFEK--LEILGKVERSLDR 154
```

```
                                                       N-Box
                                             ─────────────────────
BA1956      220 AEKEIELDLD--LEK----VHITADQESMSQ-VWINLIHNSIKFTPSSGT---ISIKLKE 269
BC1801      224 -DANMSFYIK-SDEV----LHVEVDVALIVR-LFENVIGNSIMYGKDGKE---IAIETSN 274
BC1957      217 AEKEIELELD--LEK----VYYIADQESMSQ-VWINLIHNSIKFTSGGT---ITIQLKE 266
BH3912      199 IQKGIGFDIQLEVT-----D-VLTDAKWLSF-ILRQLLSNAVKYSEASD----IIIKSDV 247
BH2700      207 IYIHHILFVIEGMEG-----VRLITDEKWNEV-LLEQIISNAVKYSRGQGEMKKIYLSGQA 260
BH0289      211 ---ESGFQVQFIGEE----METPSDRKGLAF-IVEQILANSTKYAAANQDKPIIKFEAHY 263
BH0272      202 IEEEIPFRVT-IAEE----VILYSDRKWMKV-VVYQLLSNAIKYGEKHS---TVHIYYR- 251
BH1199      240 FKITKRIEPMD--------ELPKGVEDQLFR-MLQEAISNILRHAQAHH----VEVRFNQ 286
BliBacS     210 -KHDIDINVQIPEKK----CFVIADRLSLIR-VIENIVRNGIHYGKAGKVLG-IELTESE 263
BsuYtsB     199 IQKGIGFDIQLEAK-----E-VLSDAKWLAF-IIRQLLTNAVKYSEASE----IEIKSFQ 247
BsuYvqE     239 IDIEWDIQDT---------AISKGVEDHLFR-IVQEALSNVFRHSKASK----VTVILGI 284
BsuYvcQ     217 IKRRIFPTLHVPPNA----VQISSDQKWLSF-VVEQILENALKYSKQGVGD-FITIRIET 270
BsuYbdK     217 -MSGIEIHYKPADQD----VIWMSNTLWMER-LFDNIFQNILRHSKAKK----MSVIIEH 267
CAC3516     218 LDCEIVYKHLFTGN-----MMIMVNEIMIGR-VFGNIFSNVVRYGGKNE----IKWYMTG 267
CAC1517     212 IRHHIFPRIIEKEN-----VVVETDRKWIKF-VINQIVINAIKYSKEEKGDKHITFEIKE 265
CAC0372     202 TYGNAFPKVEFHVDK----ALVLTDKRWSTF-IIDQIISNSIKYSKKEEKG-YVYFNIVQ 255
CAC0225     201 IKKHITKLKLEIDER----FNVETDKKWFLF-IILNQIISNALKYTNDMGN---IIIKAFE 251
CPE0841     203 INKRIAIDLEDLD------YKVYSDEKWMEF-IINQVINNAIKYSAKNSR---VKIFANK 252
EF0927      206 IQRRIQFSIEGED------EAVLTDRKWVVIF-IPRQLLSNAVKYTFGGT---ITVLISK 255
Lsa HPK1    208 IQNRIQFRLIGEE------QTIVLTDAKWIVF-IILNQIVSNALKYTQNGQ---ETIDLAH 257
LMO1741     209 IGKKMKLDLQNVD------MDVRTDSKWIGF-ILDQILSNALKIYTKSGGE---VKTICDT 258
Sau MW0622  204 QVKGIGFDVDFKVD-----DYVYTDIKWCRM-IIRQILSNALKYSENFN----IEIGTEL 253
SA2417      171 IDQKTKIHYEPCH------HEVLTDVRWTSL-MIEQLINNALKYARGKD-----IWIEF 217
SA0615      204 QVKGIGFDVDFKVD-----DYVYTDTKWCRM-IIRQILSNALKYSENFN----IEIGTEL 253
Sau SaeS    217 KTATLEVNFCKRNSC----ILSISKRQLERI-LNKTYLMNALKFSNVGSR---IDINISE 268
SE2194      173 IEQKTQIHYEKSE------DTILTDAQWASI-MIEQLLNNALKYAKGKD------IWIDF 219
SE0428      204 QAKGIGFBIDFKDE-----QKVYTDVKWCRM-MIRQVLSNSLKYSDNST----INLSGYN 253
GBS0964     193 LSKSLSTIIE---GD----NIWKTDKKWLTF-ALSQVIDNAIKYSNPESK---IIISIGE 241
GBS0430     214 -KENRQVMIDVAPDV----SKLSSQYDKLSR-ILNLISNAVKYSDFGSF---LTIKAYS 265
GBS0122     229 QAKRINPQID--SKF----YTVYSNSDLIMQ-VWINLIDNAIKYSDDIVD---LRVRMEE 278
SmuMbrD     196 LQKDLSITID---GD----WEIKSDKKWLSF-VFSQIILDNAIKYNKKGGQ---ITIKIKE 244
SP1632      214 -QERRDVHLQVIPES----ARIEGDYAKLSR-IIVNLVDNAFKYSA-GTK---IEVVAKL 265
SP0084      197 IQKGLNVNLHDLD------KEIVTDKKWLLV-VIEQIISNSLKYTKEGG------LEIYM 243
BL1001      225 HAHDIRVTV---PAD----ITMEGDQDRLRQ-LFTNTIANALKHSADGTT---VLVDAHE 273
SAV2971     229 TRTDVHLHLDVSPPE----LTAHADPERIHQ-VVANLIDNAVKHSPPHGR---VIVKARR 280
SAV7391     253 SVRHHFDGELP--------QLSEETELVVYRMAQEGLTNTARHGADR---AELRLHRV 300
SCO5282     236 SRTDVHLALDVFPPE----LTAHADPERIHQ-VVANLIDNAVKHSPPHGR---VIVRARR 287
SCO6424     216 TVRHDIATGLP--------GLGDNADLVLYRMAQEGLTNAARHSGARL--VVLSLERAG 264
SCO5784     239 TVQHHIPGDLP--------PLAMEAELVLYRMAQEGLTNTARHADAAR--AALTLHPLP 287
SCO6163     241 RRHGVRLVGDAVAA-----VFMEVDGKEMSR-VLGNLLVNAIRRFPADG-----TVAVAA 289
ALR3155     200 ASRRVHISFNYGDSDWRRSLWNGDPLQLQR-VLYNLLVNAINHSRRGDR---VEVVLET 255
HaeArcB     213 -EKNLTFSLELEPNLP---NVLNLDRVRLSQ-ILMNLISNAVKFTDQGN----IILKIMR 264
RS03089     213 QARACAVILDAPGS-----FVAEVAGETLYR-AFENVVRNAVKYAPNTT---VEIHAQV 263
XneEnvZ     209 AEQHGEVNIEHCLSDHP--IFILAMPLSIKR-AIANMFTNAQRYGNWIR---ISSGTTE 262
TM1258      198 -SKKIKVNMFVDVET-----IETDRFVFHT-ILKNLVSNAVKYSYFDS-----VVEISI 245
```

FIG. 10 (cont.)

```
                                    D-Box           F-Box
BA1956      270  Y--ETL------VEVRIRDTGSGISEEQKQHIFERFYKAD----SSRNRAYGGSGLGLA  316
BC1801      275  KTMN-------VEVEIKNFGQCIPKEDLPYVFEKFYRSE----KSRSSHTGGKGMGLA  321
BC1957      267  H--ETV------VEVRIRDSGIGISEEQKQHIFERFYKAD----SSRNRAYGGSGLGLA  313
BH3912      248  VS-G-K------TVVEVIDFGRGIEKDLPRIFEKGFTST----KTDQTN-GATGMGLY  293
BH2700      261  DG--EA------WIETIRDEGVGIFYDLERVFEPPFTGE----NGAKVSGFLRDWFIY  307
BH0289      264  DKGKDQ------RIETIRDNGPGVSEELFIFDKGFTGR----RGAYTR-QATGMGLF  311
BH0272      251  ---N--------GQESIHNRGETIFKSEINRLFNLFYTGS----KGRKRS-EATGIGLY  294
BH1199      287  TE--RQ------VRLKILDDGVGF------------------DVQKETHGSYGLQ  315
BliBacS     264  HE----------YQELIWDQGPGIPEARLKTCLIECTAET----GREALMTGAAWGLF  307
BsuYtsB     248  KG-E-Q------TQLQVKDCGRGIDPKDVFRIFDKGFTST----TDHHDQ-ASTGMGLY  293
BsuYvqE     285  KN--SQ------LRLKVIDNGKGF-------------------KMDQVKASSYGLN  313
BsuYvcQ     271  QG-H-E------TRLSVADEGIGIPPQDLPRIEDAFFTGE----NGRTMK-EATGMGLY  316
BsuYbdK     268  G-----------DVFIRDDGIGFDRNE----------------SS---EGLGLK  291
CAC3516     268  YS-QGS------YAYFEIEDNGIGVPDKDISSLFLKFFTVD----KSRQIENGGIGLGLA  316
CAC1517     266  EA-S-R------STLKIADEGIGIPKEDITRVFNAFFIGK----NGRKTD-ESTGMGMY  311
CAC0372     256  SN-N-K------THEVIKDNGVGIPKYDLKRIFEPFFTGE----NGRNFE-NSTGIGLY  301
CAC0225     252  DD-N-E------KVVIIEDNGIGIKKFDLRIFSKSFTGY----NGRKENSKATGMGLY  298
CPE0841     253  SK-N-S------ITLKIKDSGVGIHNKDLQRVFEKGFTGE----NGRRFT-KSTGMGLY  298
EF0927      256  NK-Q-G------IYELSLKDSGIGIPTQDRRIFDKGFTGE----NGRKSEQHSTGIGLY  302
Lsa HPK1    258  DE-Q-G------VWLSVSDSGIGIPAEDIPRVFDKGFTGQ----NGRQSNQRSTGLGLY  304
LMO1741     259  EA-SGK------KVLHMKDNGRGIKEEDLPRVFEQGFTGN----IGRQEK-KATGMGLY  305
Sau MW0622  254  ND-Q-H------VSLYIKDYGRGISKKDMPRIFERGFTST----ANRNET-TSSGMGLY  299
SA2417      218  DE-Q-S------NQLHVKDNGIGISEADLPKIFDKGYSGY----NGQRQS-NSSGIGLF  263
SA0615      254  ND-Q-H------VSLYIKDYGRGISKKDMPRIFERGFTST----ANRNET-TSSGMGLY  299
Sau SaeS    269  NEDQDT------IDIAISDGCGIGIPELQERIFERTTRVE----NSRNTKTGGSGLGLY  317
SE2194      220  DV-A-N------QTEQIKDNGIGISKADIPKIFDKGYSGF----NGRLNE-QSTGIGLF  265
SE0428      254  IE-G-H------VVLKIKDYGRGISKRDLPRIFDRGFTST----TDRNDT-ASSGMGLY  299
GBS0964     242  E-----------SIRIQDYGIGILEEDIPRLFEDGFTGY----NGHEHQ-KATGMGLY  283
GBS0430     266  N--RQD------IVLDHIDQGVGIKDEDLASIFNRLYRVE----SSRNMKTGGHGLGLY  312
GBS0122     279  TN-NHY------LRVIISDKGRGISQYDVQHIFDRFYQAD----QSHNQQ--GNGLGLA  324
SmuMbrD     245  N-----------QTLLIRDTGIGILKEDIPRLFEEGFTGY----NGHEHQ-KATGLGLY  286
SP1632      266  E--KDQ------LSISVTDEGQGIAPEDLENIFKRLYRVE----TSRNMKTGGHGLGLA  312
SP0084      244  D----D------QELCIKDTGIGIKNSDVLRVFERGFSGY----NGRLTQ-QSSGLGLY  287
BL1001      274  DENQGT------IVTNVVNFGSQIAPSDRLDIFRRFVKG----KTGPGTESGGTGLGLS  322
SAV2971     281  GPAPES------LDLEVLDEGPGIPESEWHRVFERFNRGAVSAPHGPSD-GGTGLGLA  332
SAV7391     301  A--DG-------VELVRDNGTG-------------------AGRAPEGAGIR  325
SCO5282     288  GELPES------LPLEVLDEGPGIPRSEWRRVFERFNRGSVSRPHGPGSD-GGTGLGLA  339
SCO6424     264  --DA--------VRLRVRDDGRGF------------------DDSGGAVEGAGIR  291
SCO5784     288  GDAG--------VELVLRDDGTG-------------------LGTAAEGAGIR  313
SCO6163     290  ERSADG------VVVSVTDGCGGIPEEDIRVFDTGWRG----THARTPPAGAGLGLA  337
ALR3155     256  QAS---------YQVVKISDTGAGIQAEQFFHLFERFYQG------HSERQAKGSGLGLY  300
HaeArcB     265  NQ--D-------CYHFIVKDTGMGISPFFQKHIFEMYYQVK----ESRQQS-AGSGTGLA  310
RS03089     264  SAPATPQGGDVKWLEVSVCDRGFGVPAEFCETIFEPFFRRLEPHWHEGAAQAVPGTGLGLA  323
XneEnvZ     263  AFG---------WFQVEDDGSGMTKEFADVLFQPFTQK----RRFRHVRHNGAGLGLS  308
TM1258      246  TG----------ERLSVKDQGIGIKEEEKSRIFERFYRG----SEALKMAPGSGLGLS  289
```

FIG. 10 (cont.)

```
                        G-Box
                     ─────────────
BA1956      317  IVKKVLDLHQGEIKVESEEGNGTECIVCIPNYE---------------EK-------- 351
BC1801      322  ISKSIAQLHQGDITVRSN-DKEIVFTVKLPQYK---------------KVRKS----- 358
BC1957      314  IVKKVLDLHHGEIKVESEEGKGTEFIVRMPNHE---------------EK-------- 348
BH3912      294  LAKRVAEFLLIDLAVSSTVGECTTFTLTFPKEN---------------EFVRTLGM--- 334
BH2700      308  MKKNCQRTRAHDCNTVISGQRNRNIDSLPYEIVRYF------------------- 343
BH0289      312  LVSKMAYDIAIQVDAKSELGSCLTISLIFPRVN---------------EA-------- 346
BH0272      295  LVKRILVTLDHPFELTSH-HQEITFTIELSKS----------------ISTAAD---- 331
BH1199      316  TMHERINEIGGVLDIVSAPGKGTQLEAKIPIT----------------WRGE------ 351
BliBacS     308  SPNRSSKKTADAYGHRASRGKKRRIVFRCLNKT---------------ISNHLRIN--- 348
BsuYtsB     294  LAKKAAAPLLIHIDVESEFGACTVFTLTFPIRN---------------QFEHVISV--- 334
BsuYvqE     314  SMKERASEIGGVAEVISVEGKGTQIEVKVPIFP---------------EEKGENERDSSI 358
BsuYvcQ     317  LAKQVCSRLGHKLYAESKEGAGTVMTIVFSSDT---------------LVNVTAL---- 356
BsuYbdK     292  IIEDTCRLLAITYELFTN-DNGTGPLFSKE------------------------ 320
CAC3516     317  SCKSIIEYHGGEIYAYSSEYGCLGIKFSLPLAKH--------------------- 350
CAC1517     312  LSKKICDALGHQIFAETNEIKCASFSIVFYKG----------------KNIFKL---- 349
CAC0372     302  ICKKIADNLGHEISVESEINKGTIVKETYMAKV--------------------- 334
CAC0225     299  LSNKIAEKLGHNITIESKYNEGTKLYIHFPKWC---------------DYYDVTKM--- 339
CPE0841     299  LCKNLCDKLGLGLKITSEENEGTEVNIIFPIGD---------------AIIAN----- 336
EF0927      303  LAHSIAKKLGHDLTVESTEGQGTIMTLFFPSLS---------------YYNEVK---- 341
Lsa HPK1    305  LAKSLSNKLGHATLCQLN---ARKWCDFQITLY---------------LFKLL----- 339
LMO1741     306  LAKQMAKKLGHEICIQSESGVGTEVKIYFEQKD---------------DYLLIAKD--- 346
Sau MW0622  300  LVNSVKDQLGIHEQVTSTVGKGTIVRLIFPLQN---------------EIVERMSEVTN 343
SA2417      264  IVKQTSTHTNHPVSVVSKQNESTTFTIQFPDE------------------------ 295
SA0615      300  LVNSVKDQLGIHEQVTSTVGKGTIVRLIFPLQN---------------EIVERMSEVTN 343
Sau SaeS    318  LANELACQNNAKISVRSDIDVGIIVIVTLHKLD---------------ITS------- 353
SE2194      266  IVQHIANHLNIQVTVQSELNHGIVFFIHFTKEK---------------------- 298
SE0428      300  IVQSVKEQLGIEVKVDSIVGKGTTPFYFIFPQQN--------------EIIERMSKVTR 343
GBS0964     284  MTKPVLSSINLSISVDSKINYGIAVSTHK-------------------------- 312
GBS0430     313  LARQIAHQLNGDILVESQYQKGSKFSLVLKLQK--------------------- 345
GBS0122     325  IVKRIIVLCKGRISVSSQFEIGTEFCVELPLS--------------------- 356
SmuMbrD     287  MAKKVLNNLELDINIESQIDQGTQVYVTKRR----------------------- 317
SP1632      313  IARELAHQLGGEITVSSQYGLGSTFTLVLNLSG---------------SENKA---- 350
SP0084      288  LSKKISEELGHQIRIESEVGKGTTVRIQFAQVN---------------LVLE----- 324
BL1001      323  IARWAAQLHGGTVKWVDD-TRGADFEIILRKYH---------------IAER----- 358
SAV2971     333  IARWAVDLHGGRIGVAES-QRGCRIQVTLPGLP---------------SLPS----- 368
SAV7391     326  GMRERALLICAGLAVEPGPDRGTDIRLRITSTTSTTSTTSVMNATSTGDRSGPRTGTPPH 385
SCO5282     340  IARWAVDLHGGRIGVAES-ERGCRILITLPGLP---------------STSG----- 375
SCO6424     292  GMRERALLICADLVVGPARGGGTEVRLIVPV-------------GDRVPDRVA---- 331
SCO5784     314  GMRERALLICAEIHFEPAPGGGTDVRLRVPAPP-----------GDRCADRTGDSP- 358
SCO6163     338  IVRGIVEAHRGATVRNIPG-GCRFEVILPPAGA--------------------- 370
ALR3155     301  LSRQIIAAHNGIIWAENRVPTCAMFAFKLPFLPFQP------------SLSASDGF--- 344
HaeArcB     311  ISKNIAQLMGRGFNS---------------------------------------- 325
RS03089     324  LARRALALHGGSIRAVPREGGCLRVTARLPSAVMS-------------APSDHP---- 365
XneEnvZ     309  IIRRIIDSHEGYIEVRESEKGGLSIRACFPLNTK---------------------- 342
TM1258      290  IVKHLCDTIGYRLEVNSQWLVGSEFIVHFK----------------------- 319
```

FIG. 10 (cont.)

COMPOSITIONS AND METHODS FOR SCREENING ANTIBACTERIAL COMPOUNDS

RELATED APPLICATION

This application claims priority to and the benefit of U.S. Provisional Application 60/480,649, filed on Jun. 23, 2003.

GOVERNMENT SUPPORT

This invention was supported in part by NIH grant GM47446; the United States Government has certain rights to this invention.

FIELD OF THE INVENTION

The present invention pertains to compositions and methods for screening compounds putatively having antibacterial activity. Specifically, methods of the present invention are designed to ascertain if a specific putative antibiotic triggers a cell envelope stress response in bacterial organisms.

BACKGROUND OF THE INVENTION

The bacterial cell envelope is the first and major line of defense against threats from the environment. It is also the target of numerous antimicrobial substances, many of which function to inhibit the growth of competitors. Resistance against antibiotics is therefore crucial for bacteria to live in a complex biosphere, such as a soil ecosystem. Sensing the presence of harmful compounds and transmitting this information to allow a quick adaptational response is the first and most important step to ensure survival.

Antibiotics that act on the cell envelope, such as vancomycin, bacitracin, nisin, and ramoplanin, trigger global stress responses coordinated by Extracytoplasmic Function (ECF) σ factors ($\sigma^W$ and $\sigma^M$) and two-component regulatory systems. Some of the genes that are induced by antibiotic stress play a direct role in antibiotic resistance, a growing problem among Gram-positive pathogens.

The Extracytoplasmic Function (ECF) σ factors are small regulatory proteins that are quite divergent in sequence relative to most other σ factors and form a phylogenetic distinct group within the $\sigma^{70}$-family. They often recognize promoter elements with an "AAC" motif in the −35 region. In many cases the ECF σ factor is co-transcribed with a downstream gene, which encodes a transmembrane anti-σ factor. Most of the known systems control functions associated with some aspects of the cell surface or transport.

The genome of Bacillus subtilis contains seven ECF σ factors. The regulons of $\sigma^W$, $\sigma^M$ and $\sigma^X$ have been identified, linking their functions to antibiotic stress response, general cell envelope stress and maintenance of cell envelope net charge, respectively. Two antibiotic resistance determinants have also been described previously. The fosfomycin resistance gene fosB is controlled by $\sigma^W$, and the bacitracin resistance gene bcrC is under the dual control of $\sigma^M$ and $\sigma^X$.

The two-component regulatory systems also play a major role in bacterial responses to antibiotics. Each two-component system is located next to target genes that are strongly induced by putative antibiotics that interfere with the lipid II cycle in the cytoplasmic membrane (such as bacitracin, vancomysin, nisin and ramoplanin). When an antibiotic is applied to a bacterial organism, a biochemical cascade of events is triggered. These events can render bacterial resistance to antibiotics.

Currently there exists a need to understand systems that are induced by putative antibiotics in order to provide insights into the mechanism of action.

SUMMARY OF THE INVENTION

The present invention pertains to compositions and methods used to analyze antibiotics. Specifically, methods of the present invention are designed to ascertain if a specific putative antibiotic triggers a cell envelope stress response in bacterial organisms.

One embodiment of the present invention is directed to an antibiotic detection system, comprising: a lipid bilayer and at least one receptor protein. In this embodiment, the receptor protein is integral within the lipid bilayer. In one aspect, the receptor protein has kinase activity and has an affinity for one or more putative antibiotic compounds. This embodiment further comprises at least one substrate for the receptor protein and at least one reporter. In one aspect, the reporter can be induced by the substrate when the substrate is phosphorylated.

A reporter platform constructed based upon these systems provides a useful screening tool for undecaprenyl pyrophosphate (UPP) interacting antibiotics, showing a very sensitive, concentration dependent response to its identified inducers. This reporter platform can be used either as an initial screen or to help define the mode of action in previously identified compounds possessing antibacterial activity.

In another embodiment, the invention is directed to a detection system comprising at least one receptor protein selected from the group consisting of: LiaS, YvcQ, and BceS. In one aspect, the detection system also comprises at least one substrate selected from the group consisting of: LiaR, YvcP, and BceR and at least one reporter including a promoter region and a fusion gene, wherein the substrate acts on the promoter region, inducing the reporter. In one aspect, the promoter region is selected from the group consisting of: LiaIH, YvcRS, and BceAB.

Other features and advantages of the present invention will become apparent in the following detailed description of the embodiments of the invention, with reference to the accompanying drawings.

BRIEF DESCRIPTION OF THE DRAWINGS

FIG. 5 is a functional dissection of the liaI promoter (PliaI). FIG. 5(a) shows a primer extension mapping of the liaI transcriptional start site indicating transcription initiation with the A residue indicated in the sequence to the right (SEQ ID NO: 6). FIG. 5(b) is the intergenic sequence between yvqJ and liaI (SEQ ID NO. 5). FIG. 5(c) is a graphical representation of the intergenic region and outline of the fragments used for the promoter dissection. The features of the region are represented by black boxes and labeled as above. The arrow indicates the transcriptional start site. FIG. 5(d) shows a β-galactosidase assay for promoter dissection;

FIG. 6 shows organization and bacitracin-dependent expression of the liaIHGFSR locus of *Bacillus subtilis*. FIG. 6(*a*) is a graphic representation of the lia locus including liaS (histidine kinase) and liaR (response regulator). FIG. 6(*b*) shows Northern blots showing the bacitracin-dependent expression of liaH and liaG, with the fragments used as probes for liaH and liaG represented as thick black bars above the locus. FIG. 6(*c*) shows a secondary structure of the stem-loop directly downstream of liaH (SEQ ID NO:7);

FIG. 7(*b*) shows concentration-dependent killing of *B. subtilis* by the four antibiotics from the same culture as 7(*a*);

FIG. 9(*b*) shows the domain organization of the bacitracin-sensing histidine kinases and analogous systems as deduced from SMART analysis and TM: putative transmembrane helices, according to the DAS transmembrane prediction server;

FIG. 10 is "HK align.doc" Multiple sequence alignment of histidine kinases with a domain organization similar to BacS and LiaS of *B. subtilis* (SEQ ID NOS:82-126 respectively, in order of appearance.);

DETAILED DESCRIPTION OF PREFERRED EMBODIMENTS

Figure 1:
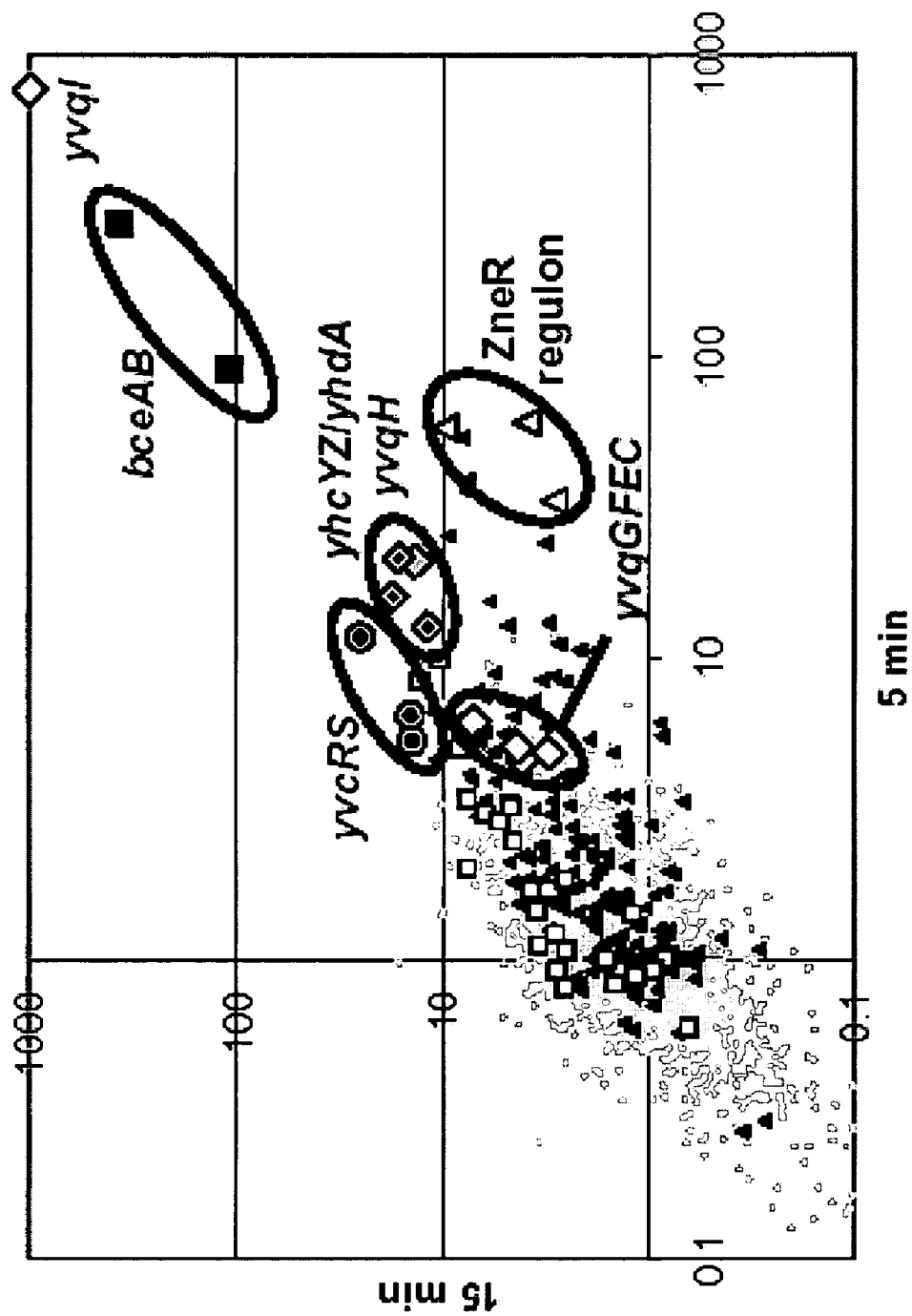
FIG. 1 is a graphical representation of the bacitracin stimulon.

The present invention pertains to compositions and methods used to analyze antibiotics. Specifically, methods of the present invention are designed to ascertain if a specific putative antibiotic triggers cell envelope stress response in bacterial organisms.

One embodiment of the present invention is directed to an antibiotic detection system, comprising: a lipid bilayer and at least one receptor protein. In this embodiment, the receptor protein is integral within the lipid bilayer. In one aspect, the receptor protein has kinase activity and has an affinity for one or more putative antibiotic compounds. This embodiment further comprises at least one substrate for the receptor protein and at least one reporter. In one aspect, the reporter can be induced by the substrate when the substrate is phosphorylated.

In one aspect of the invention, three two-component systems are described: LiaR & LiaS (formerly YvqCE); YvcP & YvcQ; and BceR & BceS (formerly YtsAB). These systems, for example, can be used to analyze antibiotics including but not limited to, vancomycin, bacitracin, nisin, and ramoplanin. Interestingly, some of these antibiotics appear to interfere with the lipid II cycle in the cytoplasmic membrane. (LiaRS was appropriately named "lipid II cycle interfering antibiotic response regulator and sensor" for its narrow spectrum of inducers.)

When an antibiotic is applied to a bacterial organism, it typically interacts with and activates the first component of each system (LiaS, YvcQ, or BceS), which, in turn, can phosphorylate a second component (LiaR, YvcP, or BceR). This second component can then act on a promoter region of a reporter gene, resulting in the elaboration of a signal. The signal of the reporter can be detected and measured to determine the effectiveness of the applied antibiotic in terms of its ability to trigger resistance mechanisms of the bacteria.

A reporter can comprise a fusion gene such as the β-galactosidase system. Other reporter constructs are well known by those skilled in the art and are included herein.

The bacterial cell envelope is the target of numerous antimicrobial substances, many of which are produced by soil microbes. *Bacillus subtilis* (genome accession # Z99120 AL009126) is one such ubiquitously distributed soil microorganism, and thus, provides an excellent model system to investigate the responses of bacteria to antimicrobial compounds made by other soil bacteria. It is estimated that more than ⅔ of all antibiotics currently in use are natural products of *Streptomycetes* and other actinomycetes that are abundant in the soil ecosystem (Bentley et al., 2002, *Nature*. 417: 141-147, the entire teaching of which is incorporated herein by reference).

In response to sub-lethal concentrations of antibiotics, bacteria often induce an adaptive response that can contribute to antibiotic resistance. Disclosed herein is the response of *Bacillus subtilis* to antibiotics such as bacitracin, vancomycin, nisin, ramoplanin, and alike inhibitors of cell wall biosynthesis. (It should be understood that other putative antibiotics could be subjected to the method of the present invention.)

Bacitracin is a potent narrow spectrum antibiotic directed primarily against Gram-positive cocci and bacilli. It is widely used in topical "triple antibiotic" ointments (along with neomycin and polymyxin B) for the treatment of minor cuts and burns (Berger et al., 2000, *Cutis*. 65: 401-404, the entire teaching of which is incorporated herein by reference). Its nephrotoxicity limits its systemic use and it is considered only as a last resort for the treatment of gastrointestinal infections (Arky, 1997, *Physicians' Desk Reference for Non-Prescription Drugs*, the entire teaching of which is incorporated herein by reference). However, it is widely used as an animal feed additive in the livestock industry (Huyghebaert and De Groote, 1997, *Poultry Science*. 76: 849-856, the entire teaching of which is incorporated herein by reference). Despite its widespread use, bacitracin resistance is still scarce (Ming and Epperson, 2002, *Journal of Inorganic Biochemistry*. 91: 46-58, the entire teaching of which is incorporated herein by reference).

Bacitracin is a branched cyclic dodecylpeptide antibiotic produced by *B. licheniformis* and some strains of *B. subtilis* (Azevedo et al., 1993, *Appl Biochem Biotechnol*. 42: 1-7; Ishihara et al., 2002, *Curr Microbiol*. 45: 18-23, the entire teaching of which is incorporated herein by reference). It is synthesized as a mixture of up to fifty different closely related congeners (Kang et al., 2001, *Electrophoresis*. 22: 1356-1362, the entire teaching of which is incorporated herein by reference) and needs a divalent metal ion (most efficiently $Cu^{2+}$, $Mn^{2+}$, or $Zn^{2+}$) for its biological activity (Adler and Snoke, 1962, *J Bacteriol*. 83: 1315-1317, the entire teaching of which is incorporated herein by reference). Bacitracin inhibits bacterial cell envelope biosynthesis by binding very tightly to the long-chain C55-isoprenol pyrophosphate (Stone and Strominger, 1971, *Proc Natl Acad Sci USA*. 68: 3223-3227; Storm and Strominger, 1973, *J.*

Biol. Chem. 248: 3940-3945, the entire teachings of which are incorporated herein by reference).

Undecaprenyl pyrophosphate (UPP) is the lipid carrier responsible for the translocation of cell envelope building blocks from the cytosol to the external side of the cytoplasmic membrane, where they are incorporated in the macromolecular network of the cell envelope (i.e., peptidoglycan, teichoic acids and polysaccharide capsule). Binding of bacitracin to UPP prevents its recycling by dephosphorylation to the monophosphate form that is normally reloaded on the inner face of the membrane.

The glycopeptide antibiotic vancomycin is produced by *Streptomyces toyocaensis* and other actinomycetes and binds tightly to D-Ala-D-Ala termini on the pentapeptide side chains of cell wall precursors, thereby inhibiting the formation of peptide cross-bridges by peptidyltransferase. While self-resistance of the producing-strain has been reported, no vancomycin resistance mechanism has so far been described for *B. subtilis*.

The bacitracin stimulon of *B. subtilis* was examined using global transcriptome analysis. Using DNA microarray technology, RNA was extracted from cultures of wild-type strain CU1065 and the liaH mutant HB0920 was grown in LB medium to mid-logarithmic growth phase ($OD_{600} \approx 0.45$) and either left untreated or induced with 100 μg/mL bacitracin for 5 or 15 min. Under most conditions tested, about 60-70 genes were induced greater than 5-fold. FIG. 1 shows the fold-changes of gene-expression levels of the data-set 5 min after bacitracin-addition (on the x axis) plotted against the fold-changes 15 min post-induction (on the y axis; values of both data-sets relative to the expression level in the un-induced control experiment). The scatter-plot represents the data sets obtained for strain HB0920 (yvqH was still detected as bacitracin-inducible due to the presence of a remaining region near the 5'-end of the gene). The most strongly induced gene signals are highlighted and circled. Members of the $\sigma^M$ (white open squares) and $\sigma^B$ (small black triangles) regulon are highlighted. All other gene signals are represented as small gray diamonds. Note that for the generation of this graphical display the data sets could not be filtered to remove low quality and non-reproducible signals, thus some of the background signals (small gray diamonds) that appear to represent highly regulated genes are not significant.

The liaH-deletion mutant was included in the analysis because the well-characterized LiaH-homologue in *E. coli*, PspA, functions as a repressor of transcription (Adams et al., 2003, *J Bacteriol.* 185: 1174-1180; Bordes et al., 2003, *Proc Natl Acad Sci USA.* 100: 2278-2283, the entire teachings of which are incorporated herein by reference). Since liaH is strongly induced by bacitracin, it might be possible to identify target genes for this putative transcriptional regulator. The results of bacitracin treatment for HB0920 are shown in FIG. 1 and summarized in Table 1. Similar results were obtained with CU1065.

TABLE 1

Genes induced by zinc-bacitracin in HB0920, that were not part of the $s^B$ regulon

| Gene(s) | Fold induction[1] 5 min | 15 min | Regulator | Bacitracin[2] MIC [mg/mL] | (put.) Functions |
|---|---|---|---|---|---|
| I. Genes that were induced (>= fivefold) after 5 min | | | | | |
| yvqIH | 772 | 1062 | YvqEC | 500 | unknown |
| bacAB (ytsCD) | 282 | 365 | BacRS (YtsAB) | 10 | ABC transporter |
| czcD | 61 | 3.8 | ZneR | N.D. | Zn-efflux |
| cadA (yvgW) | 58 | 9.8 | ZneR | N.D. | Zn-efflux |
| czcO (trkA) | 33 | 2.8 | ZneR | N.D. | K-uptake, Zn-resistance |
| yhcYZ-yhdA | 21 | 14 | YvqEC | 500 | two-component system |
| yvcRS | 12 | 25 | YvcPQ | 500 | ABC transporter |
| ydhK | 12 | 4.4 | | 500 | unknown |
| bcrC | 10 | 9.5 | $S^M/S^X$ | 25 | bacitracin resistance prot. |
| cotY | 9.4 | 5.9 | | N.D. | spore coat protein |
| ytrBCDEF | 9.1 | 9.7 | YtrA | 500 | acetoin utilization |
| gerAA/AB | 7.1 | 4.2 | | N.D. | spore germination |
| ycgRQ | 6.7 | 7.9 | | 500 | unknown |
| yvqGFEC | 6.1 | 7 | YvqEC | 500 | unknown, unknown, TCS |
| ykvS | 5.9 | 10 | | 500 | unknown |
| yybR | 5.4 | 3.7 | | N.D. | unknown |
| yjbIH | 5.2 | 7.1 | | N.D. | unknown |
| II. Genes that were induced (>= tenfold) after 15 min | | | | | |
| ygaCD | 2 | 12 | | 500 | unknown, ABC-ATP |
| ykuNOP | 1.4 | 12 | Fur | N.D. | flavodoxin homologue |
| ytzB | 2.8 | 11 | | 500 | unknown |
| yetG | 1.4 | 10 | | N.D. | unknown |

[1]highest foldchange of transcriptional units (usually the first gene)
[2]reference value for the wildtype strain CU1065: 500 mg/mL The most strongly induced genes were bceAB and yvcRS, coding for putative ABC transport systems and liaIH, coding for a putative transmembrane-protein and a phage-shock protein homolog, respectively. Two BceAB homologs (VraDE and VraFG) are up-regulated in vancomycin-resistant *S. aureus*, and the VraDE locus is inducible by vancomycin (Kuroda et al., 2003, *Mol Microbiol* 49:807-21, the entire teaching of which is incorporated herein by reference). Thus, there is evidence linking this family of ABC transporters to antibiotic resistance in several species.

Each of these systems, bceAB and yvcRS, is positively regulated by a linked two-component regulatory system, consistent with previous transcriptome analyses of strains engineered to overexpress the corresponding response regulators (Kobayashi et al., 2001, *J Bacteriol.* 183: 7365-7370, the entire teaching of which is incorporated herein by reference). To investigate the role of these regulators in the observed bacitracin induction, allelic replacement mutants were constructed of the four response regulators genes (bacR, yvcP, liaS and yxjL) by long-flanking homology (LFH)—PCR, resulting in strains HB0927, HB0931, HB0933 and HB0936 respectively.

Each mutant strain, as well as HB0031 (sigM::kan) and CU1065, was grown in LB medium to mid-logarithmic phase ($OD_{600} \approx 0.45$) and induced with 100 µg/mL bacitracin for 15 min. RNA was isolated from induced and un-induced control cultures and gene expression monitored by Northern blot hybridization.

Figure 2:
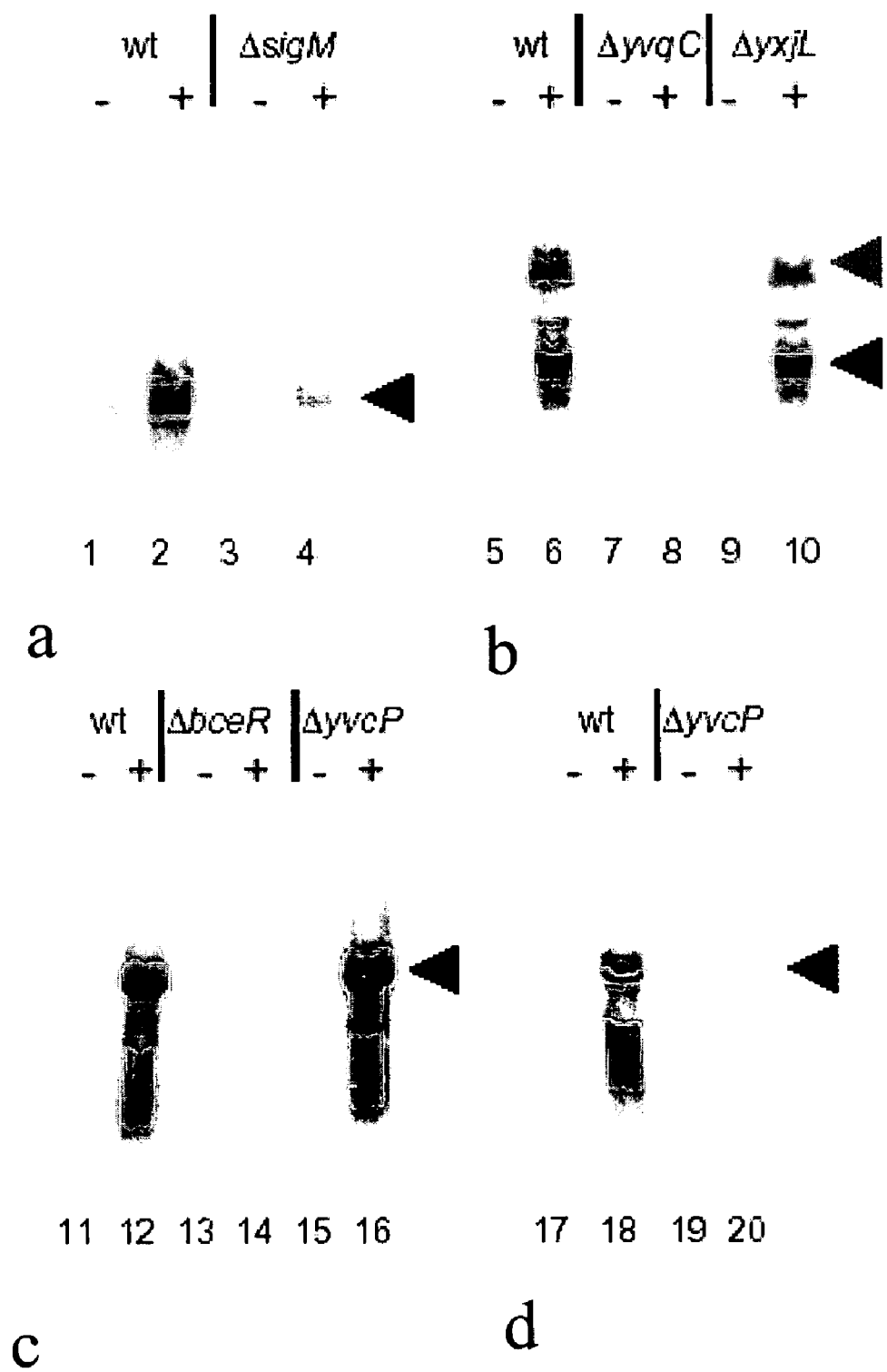
FIGS. 2(a)-(d) are a Northern blot analysis to identify the regulators of bacitracin-inducible genes.

FIG. 2 shows expression of bcrC (a), liaH (b), bceR (c) and yvcR (d) measured using 10 µg of total RNA from each sample separated on a 1% formaldehyde gel. RNA was transferred to a nylon membrane and hybridized with a radio-labeled DNA fragment containing ~500 nucleotides of the coding region of each gene. In this figure, "−" represents the un-induced control lane, "+" the RNA sample from cultures induced with bacitracin for 15 min (final concentration 100 µg/mL), and "wt" indicates the wild-type strain CU1065. The isogenic mutants bearing deletions in transcriptional regulators are indicated. Arrows indicate the major transcript(s) for each gene; their sizes correspond to transcripts covering (a) bcrC, (b) liaIH (black arrow) and liaIHGFEC (gray arrow), (c) bceAB and (d) yvcRS. For all four genes analyzed (bcrC, liaH, bceA and yvcR) the bacitracin-dependent induction of expression was verified in the wild-type strain. In the case of liaH and bceA (FIGS. 2b and 2c, respectively), no residual expression could be detected in the un-induced cultures, consistent with the fact that expression in the un-induced controls was below the detection limit in the DNA microarray experiment (data not shown).

It has been shown previously that the bcrC gene is under the dual control of two ECF σ factors, $\sigma^X$ and $\sigma^M$, but bacitracin induction was mediated by $\sigma^M$ only (Cao and Helmann, 2002, *J Bacteriol.* 184: 6123-6129; Cao et al., 2002, *J Bacteriol.* 183-2380-2383, the entire teachings of which are incorporated herein by reference). This finding is confirmed by the Northern analysis (FIG. 2). A single band corresponding to a transcript of ~0.6 kb size can be detected in all four lanes (FIG. 2a). This corresponds well to the size of the bcrC gene, which forms a monocistronic transcription unit. The bacitracin-dependent induction is lost in the sigM deletion mutant. While the $\sigma^X$ regulon is not part of the bacitracin stimulon, the residual bcrC expression is $\sigma^X$-dependent, as shown previously (Cao and Helmann, 2002, *J. Bacteriol.* 184: 6123-6129, the entire teaching of which is incorporated herein by reference).

Two major transcripts were detected with the liaH probe (FIG. 2b). The strongest signal corresponds to a ~1.1 kb band consistent with the hypothesis that the liaIH genes form an operon. A larger partially degraded transcript of about 4.2 kb likely represents the whole liaIH-yvqGFEC locus. Both transcripts were only present in bacitracin-induced cultures of CU1065 and the yxjL mutant HB0936. No signal was detected in the LiaR mutant strain indicating that expression of liaIH is completely dependent on LiaRS in the presence of bacitracin (FIG. 2b) or vancomycin (data not shown).

Similarly, the bacitracin-dependent induction of a ~2.7 kb transcript corresponding to the bceAB operon was completely dependent on BceR (FIG. 2c) and the bacitracin-inducible expression of the yvcRS operon depends on the activity of the linked response regulator, YvcP (FIG. 2d). Importantly the induction of the bceAB operon was unaffected in the yvcP mutant and induction of liaIH was unaffected in the yxjL mutant. These results contradict the overlapping regulation observed in a previous microarray analysis (Kobayashi et al., 2001, *J Bacteriol.* 183: 7365-7370, the entire teaching of which is incorporated herein by reference).

The liaIH locus shows the most dramatic response to vancomycin and bacitracin without conferring resistance to either antibiotic. Whereas LiaI is a small hydrophobic protein of unknown function, LiaH shows significant homology to *E. coli* PspA. Like PspA, LiaH might play a regulatory role: the yhcYZ-yhdA operon is induced by bacitracin only in a LiaH-deletion mutant, but not in the wild type strain (see FIG. 8). This induction was verified by β-galactosidase assays (data not shown). PspA is encoded by the first gene of the pspABCDE operon, which is strongly induced by filamentous phage infection (hence the name: Phage-Shock Protein A; Brissette et al., 1990, *Proc Natl Acad Sci USA.* 87: 862-866, the entire teaching of which is incorporated herein by reference) and a variety of other stresses (Kobayashi et al., 1998, *Microbiology.* 144 (Pt 2): 353-359; Weiner and Model, 1994, *Proc Natl Acad Sci USA.* 91: 2191-2195, the entire teachings of which are incorporated herein by reference). PspA acts as a repressor by inhibiting the transcriptional activator of psp expression, PspF, through protein-protein interaction (Adams et al., 2003, *J Bacteriol.* 185: 1174-1180; Bordes et al., 2003, *Proc Natl Acad Sci USA.* 100: 2278-2283, the entire teachings of which are incorporated herein by reference). PspA is localized peripherally, bound to the inner surface of the cytoplasmic membrane, and in the cytosol (Brissette et al., 1990, *Proc Natl Acad Sci USA.* 87: 862-866; Kleerebezem and Tommassen, 1993, *Mol Microbiol.* 7: 947-956, the entire teachings of which are incorporated herein by reference). It is thought that PspA may be involved in the maintenance of the proton-motif force and, more generally, in cell membrane integrity (Kleerebezem et al., 1996, *Embo J.* 15: 162-171, the entire teaching of which is incorporated herein by reference).

However, the overproduction of response regulator proteins may also lead to non-specific effects: a number of the putative target genes as judged from the response regulator overexpression studies (Kobayashi et al., 2001, *J Bacteriol.* 183: 7365-7370, the entire teaching of which is incorporated herein by reference) were not induced by bacitracin. In addition, there was not significant cross-regulation between these and other two-component systems as proposed by Kobayashi et al. (2001, *J Bacteriol.* 183: 7365-7370, the entire teaching of which is incorporated herein by reference). Of the bacitracin responsive two-component systems tested, only LiaSR seemed to slightly autoregulate its own expression and in each case the target genes studied were dependent only on a single two-component system.

In addition to these three two-component systems, bacitracin also induced the $\sigma^B$ and $\sigma^M$ regulons and the Zn(II)-inducible ZneR regulon. Induction of these regulons was also detected upon vancomycin treatment. The $\sigma^M$ regulon, which is known to be induced by diverse stresses (Horsburgh and Moir, 1999, *Mol Microbiol.* 32: 41-50; Thackray and Moir, 2003, *J Bacteriol.* 185: 3491-3498, the entire teachings of which are incorporated herein by reference), is regulated by the yhdLK gene products that function as anti-σ factors (Thackray and Moir, 2003, *J Bacteriol.* 185: 3491-3498, the entire teaching of which is incorporated herein by reference). These proteins are thought to be membrane-bound sensors that keep the σ factor in an inactive state through protein-protein interactions. An incoming signal results in the release of the corresponding σ factor, thereby activating the expression of its target genes (Helmann, 1999, *Curr Opin Microbiol.* 2: 135-141, the entire teaching of which is incorporated herein by reference). The $\sigma^M$ regulon includes bcrC, a previously characterized bacitracin-resistance determinant (Cao and Helmann, 2002, *J Bacteriol.* 184: 6123-6129, the entire teaching of which is incorporated herein by reference). The BceAB transport system defines a second, apparently independent bacitracin resistance pathway.

Three different bacterial bacitracin-resistance mechanisms have been described. The self-resistance of the producer *B. licheniformis* is mediated by an ABC-transport system, encoded by the bcrABC locus (Podlesek et al., 1995, *Mol Microbiol.* 16: 969-976, the entire teaching of which is incorporated herein by reference). Homologs of the bcrC gene, coding for the membrane-spanning domain of an ABC transporter have been described as resistance determinants in *B. subtilis* and *Escherichia coli* (Cao and Helmann, 2002, *J Bacteriol.* 184: 6123-6129; Harel et al., 1999, *J Bacteriol.* 181: 6176-6178; Ohki et al., 2003, *J. Bacteriol.* 185: 51-59, the entire teachings of which are incorporated herein by reference). A second mode of bacitracin resistance is through de novo synthesis of active undecaprenyl phosphate by an undecaprenol kinase. This mechanism has been found in *E. coli, Streptococcus pneumoniae* and *Staphylococcus aureus* (Cain et al., 1993, *J Bacteriol.* 175: 3784-3789; Chalker et al., 2000, *Microbiology.* 146: 1547-1553, the entire teachings of which are incorporated herein by reference). A role of exopolysaccharide production in bacitracin resistance has been reported for *Xanthomonas campestris, Sphingomonas* sp., *E. coli* and *Streptococcus mutans* (Pollock et al., 1994, *J Bacteriol.* 176: 6229-6237; Tsuda et al., 2002, *Antimicrob. Agents Chemother.* 46: 3756-3764, the entire teachings of which are incorporated herein by reference).

A third antibiotic-resistance mechanism comprises *B. subtilis* bcrC and bceAB genes encoding components of ABC transporters. Overall, this is functionally analogous to the bcrABC self-resistance mechanism described for the bacitracin-producing strain *B. licheniformis*. The self-resistance mechanism that was reported for *B. licheniformis* consists of an ABC transporter, BcrABC, that is thought to function as a bacitracin pump, consisting of a monomer of each membrane spanning domain (BcrBC) and a dimer of the nucleotide-binding domain BcrA (Podlesek et al., 1995, *Mol Microbiol.* 16: 969-976, the entire teaching of which is incorporated herein by reference). The expression of this transporter is induced by bacitracin and regulated by a two-component system BceRS (Neumuller et al., 2001, *Eur J Biochem.* 268: 3180-3189, the entire teaching of which is incorporated herein by reference). Only one resistance determinant has been reported for *B. subtilis* so far: BcrC, homologous to the eponymous protein of *B. licheniformis* (Cao and Helmann, 2002, *J Bacteriol.* 184: 6123-6129; Okhi et al., 2003, *J. Bacteriol.* 185: 51-59, the entire teachings of which are incorporated herein by reference).

Figure 3:
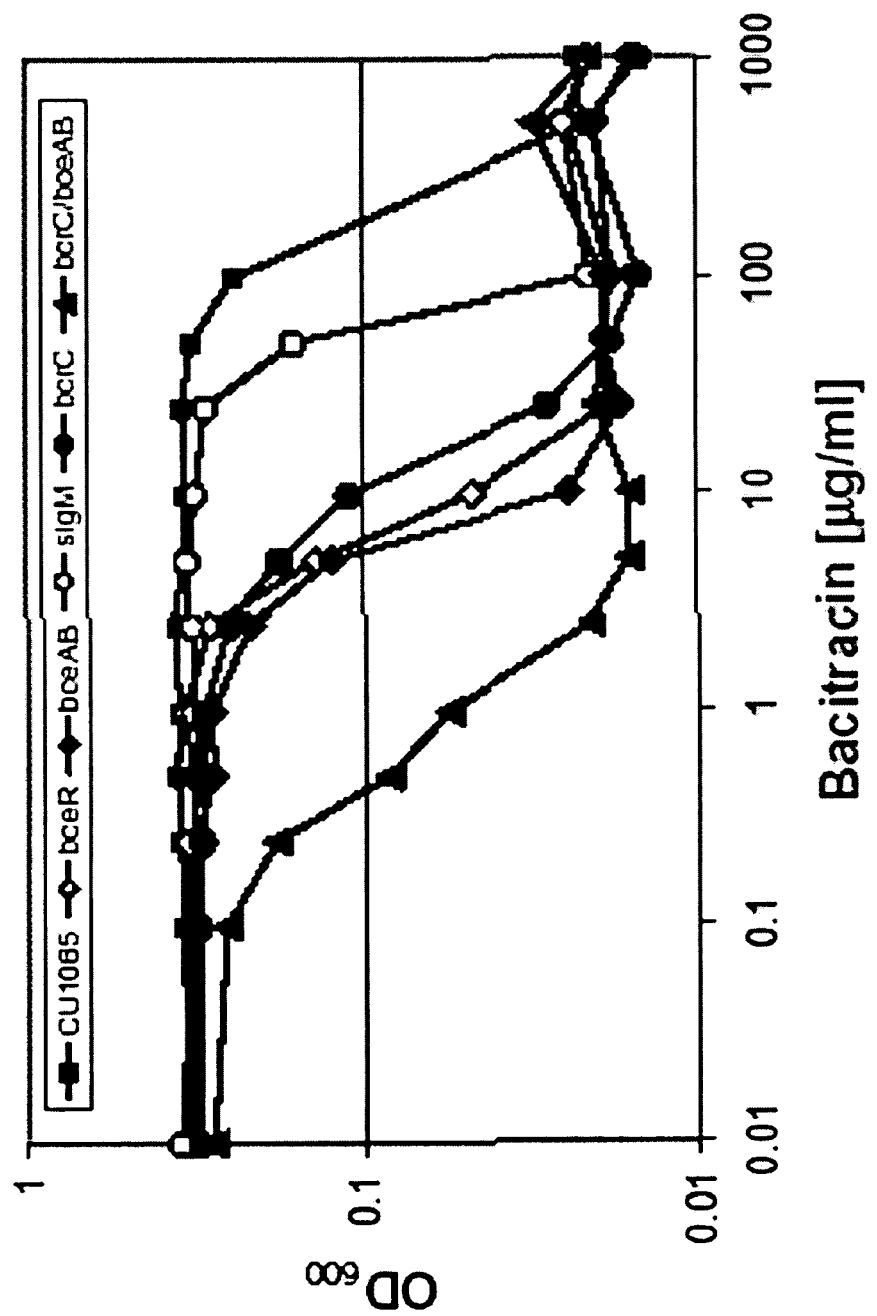
FIG. 3 shows the effect of bacitracin on growth of B. subtilis strains.

Since *B. subtilis* is closely related to the bacitracin-producing strains, it seemed likely that a similar system as described for *B. licheniformis* could exist in CU1065. The identification of two loci encoding ABC transporters that are under the bacitracin-inducible control of a two-component system supported this hypothesis. To identify additional bacitracin-resistance determinants, investigators engineered deletion mutants of strongly induced genes with homology to ABC transporters by using LFH-PCR. Measurements of the minimal inhibitory concentration (MIC) using a microtiter-plate based assay confirmed the bacitracin sensitivity of the sigM and bcrC mutants and additionally revealed a role for the bceR and bceAB genes, as shown in FIG. 3. All strains were grown in microtiter-plates for 4 hours after dilution into LB medium containing the indicated concentrations of bacitracin. The experiment was done in triplicate and a representative result is shown. Strains used were: CU1065 (black squares), 'bacR' (HB0927, open diamonds), 'bacAB' (HB0928, black diamonds), 'sigM' (HB0031, open circles), 'bcrC' HB0106 (closed circles), 'bcrC/bacAB' (HB0937, black triangle). Compare also with Table 1.

The bcrC mutant is more sensitive to bacitracin than the sigM mutant due to the residual $\sigma^X$-dependent expression of bcrC (Cao and Helmann 2002, *J Bacteriol.* 184: 6123-6129, the entire teaching of which is incorporated herein by reference; FIG. 2a). Both the bceR- and bceAB deletions led to a 50-fold reduction in MIC compared to CU1065. These resistance genes originally named ytsCD were therefore renamed bceA and bceB, and the genes coding for the corresponding regulators were renamed bceRS (formerly ytsAB).

The regulation of the *B. subtilis* bceAB and bcrC resistance genes by two separate regulatory systems suggests that they may function independently. The ability of these systems to function independently is supported by the observation that overexpression in *B. subtilis* of *B. licheniformis* bcrC and bcrAB alone results in an intermediate increase in resistance compared to the expression of the complete bcrABC locus. Expression of bcrB and bcrA alone did not result in an increased resistance, whereas expression of a bcrAC fusion locus increased the resistance almost to the level of the complete locus (Podlesek et al., 2000, *FEMS Microbiol Left.* 188: 103-106, the entire teaching of which is incorporated herein by reference). It appears that if bcrABC of *B. licheniformis*, and the bcrC bceAB genes of *B. subtilis*, do form a single ABC-transporter, the membrane-spanning domains can substitute for each other. Indeed, even bcrC alone is able to confer resistance (Podlesek et al., 2000, *FEMS Microbiol Left.* 188: 103-106, the entire teaching of which is incorporated herein by reference). Indeed, a bcrClbceAB double mutant is significantly more sensitive to bacitracin with a 200-fold decrease of bacitracin-resistance compared to the wild type strain (2.5 versus 500 µg/mL). Thus, bcrC and bacAB encode two independent bacitracin resistance pathways.

The role of ABC-transporters in mediating bacitracin resistance remains a fruitful subject for continued exploration. The bactericidal action of bacitracin is a result of interaction with undecaprenyl pyrophosphate (UPP). The inactive UPP is normally recycled to a monophosphate form by a specific, but so far unidentified, pyrophosphatase required to allow the reloading of the carrier lipid on the cytoplasmic side of the membrane. Bacitracin prevents recycling by titrating active lipid-carrier out of the cycle. It has been suggested that BcrABC functions according to the "hydrophobic vacuum cleaner" model (Podlesek et al., 1995, *Mol Microbiol.* 16: 969-976, the entire teaching of which is incorporated herein by reference), analogous to multidrug-efflux pumps of tumor cells (Higgins and Gottesman, 1992, *Trends Biochem Sci.* 17: 18-21, the entire teaching of which is incorporated herein by reference). In this model bacitracin is taken up by the transporter directly from the hydrophobic environment of the membrane.

B. licheniformis and B. subtilis are closely related organisms (Priest, 1993, the entire teaching of which is incorporated herein by reference) and bacitracin-producing strains can be found in both species (Azevedo et al., 1993, Appl Biochem Biotechnol. 42: 1-7; Ishihara et al., 2002, Curr Microbiol. 45: 18-23, the entire teachings of which are incorporated herein by reference). It is therefore surprising that the bceRSAB system of B. subtilis, while functionally analogous to B. licheniformis bceRS-bcrAB, shows no significant sequence similarity although the sensor kinases do share an unusual topology and appear to lack an extracytoplasmic sensing domain. One can speculate that these kinases may sense bacitracin-UPP complexes by binding with the transmembrane helices, although an indirect mechanism involving sensing perturbations of cell envelope structure cannot be ruled out. In the case of the B. licheniformis BacS sensor kinases, however, intramembrane-sensing and substrate binding could offer an explanation for a puzzling finding: due to the negative regulation mechanism, a bceRS-deletion mutant still expresses the BcrABC system, but it no longer confers bacitracin resistance (Neumuller et al., 2001, Eur J. Biochem. 268: 3180-3189, the entire teaching of which is incorporated herein by reference). If the histidine kinase BceS serves as the sensor for UPP-bound bacitracin, it could also deliver this substrate to the ABC transporter thereby facilitating removal.

The present investigators have identified a sub-family of sensor kinases that share the unusual domain organization noted for the bacitracin-inducible histidine kinases of B. subtilis. It is quite possible that these kinases may sense signals associated with the cell membrane and suggest the name of intramembrane-sensing histidine kinases for this group. Intriguingly, the set of two-component systems identified in the present analysis (based on the unusual topology of the histidine kinase sensor domain) corresponds closely to those shown previously to be genetically linked to ABC transporters, at least in low G+C Gram-positive bacteria (Joseph et al., 2002, J Mol Microbiol Biotechnol. 4: 503-513, the entire teaching of which is incorporated herein by reference). Without wishing to be bound by theory, investigators suggest that this genetic association may reflect a further functional link: in the case of bacitracin, the histidine kinases may function to deliver substrate complexes to the membrane-spanning domains of the corresponding ABC transporter.

Disclosed herein is the finding that treatment of B. subtilis with bacitracin leads to the transcriptional induction of numerous genes controlled by at least two alternative a factors and three two-component regulatory systems, including a second bacitracin resistance locus. Bacitracin is preferentially sensed by a sub-family of histidine kinases that appear to lack a significant extracytoplasmic sensing domain. Comparison of the bacitracin and vancomycin stimulons reveals extensive overlap, but also uniquely regulated systems.

Two-component signal transduction is a ubiquitously distributed regulatory principle in bacteria and lower eukaryotes. It is a versatile system that allows adaptational response to a huge variety of environmental stimuli, based on a simple modular system: a membrane-bound histidine kinase (HK) that acts as a sensor and a response regulator that mediates the cellular response, most often through regulating differential gene expression. The activity of as well as the communication between these two components is mediated by three phospho-transfer reactions: (1) the autophosphorylation of a conserved histidine in the sensor, (2) the phospho-transfer to a conserved aspartate in the response regulator, and (3) dephosphorylation to set back the system to the pre-stimulus state.

Three two-component systems ("TCS"), BceRS, YvcQP and LiaSR are induced by bacitracin, and one of them is also induced by vancomycin. The HK of all three TCS share an unusual overall domain organization that can be found in a sub-family of other HKs primarily from low G+C Gram-positive bacteria. Based on the organization of the input domain and the available information on their function, there is sufficient evidence that suggests they define a new sub-family of intramembrane-sensing histidine kinases.

In one aspect of the present invention, the liaIH operon can be induced by putative cell wall antibiotics. In a previous study, the response of B. subtilis to the glycoside antibiotic vancomycin, an inhibitor of bacterial cell wall biosynthesis was examined (Cao et al., 2002, Mol Microbiol. 45: 1267-1276, the entire teaching of which is incorporated herein by reference). Most induced genes were part of the regulons controlled by two ECF $\sigma$ factors, $\sigma^M$ and $\sigma^W$. However, the most strongly induced gene in these experiments was liaI, showing a more than 100-fold increase in expression level 10 min after vancomycin addition (Cao et al., 2002, Mol Microbiol. 45: 1267-1276, the entire teaching of which is incorporated herein by reference).

Figure 4:
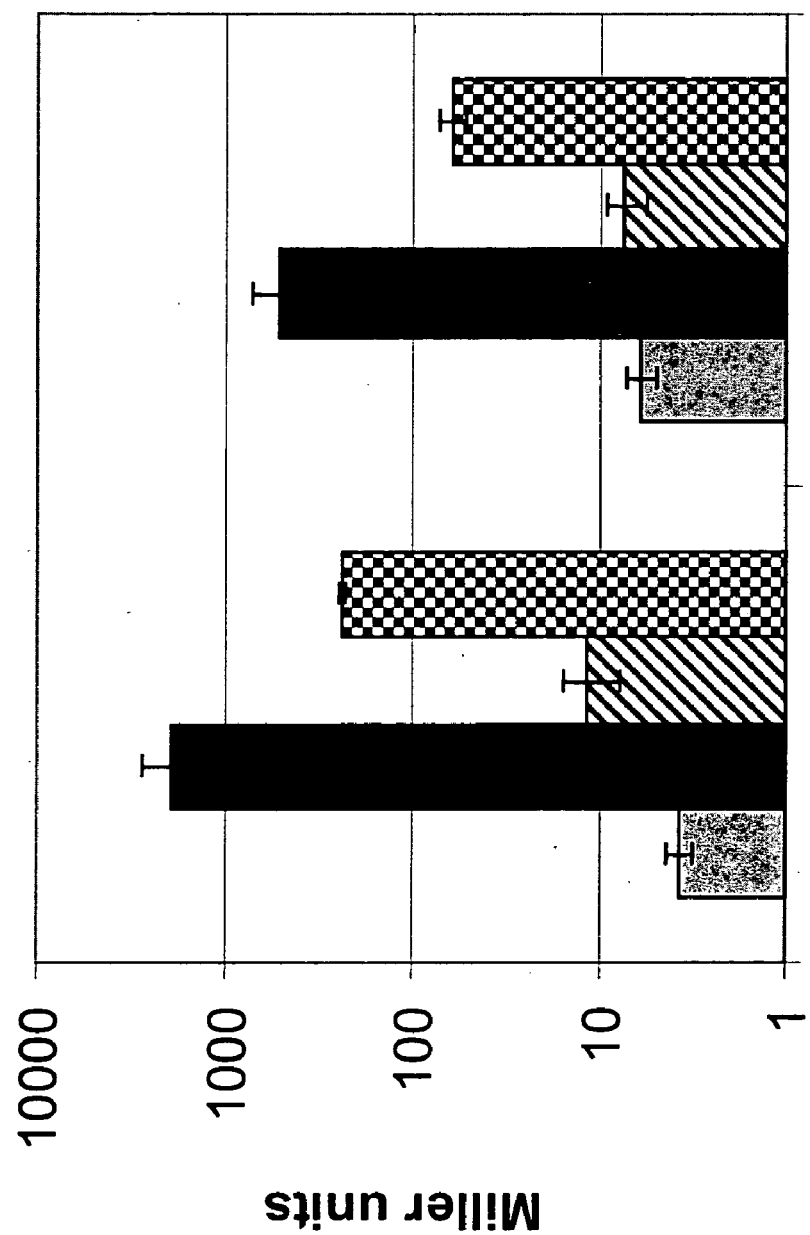
FIG. 4 shows the induction of liaIH expression by bacitracin, tunicamycin and vancomycin.

Disc-diffusion assays were used to determine the spectrum of stimuli that induce the expression of liaIH. The B. subtilis strains BFS2469 and BFS2470 (Table 2), harboring pMUTIN-insertions in liaH and liaI respectively, were plated on a medium containing the indicator dye X-gal and overlaid with filter disks impregnated with various antibiotics that interfere with cell wall biosynthesis. Specifically, cultures of B. subtilis strain BFS2469 (liaH::pMUTIN) and BFS2470 (liaI::pMUTIN) were grown in LB medium to midlog phase, 2 mL for the un-induced control sample were harvested, and the remaining culture was induced with the three antibiotics for 30 minutes, before the cells of the induced sample were harvested. All samples were taken in duplicate from two independent cultures and the standard deviation is indicated by error bars. FIG. 4 shows the results, with grey bars representing un-induced cultures; black bars representing bacitracin (100 μg/mL); hatched bars representing tunicamycin (50 μg/mL); and checkered bars representing vancomycin (2 μg/mL).

TABLE 2

Inducers of lial expression

| inducer | disk-diffusion assay[1] | conc.[2] [μg/ml] | fold induction (BFS2470)[3] | (HB0950)[3] |
|---|---|---|---|---|
| Cell wall antibiotics | | | | |
| Ampicillin | – | | | |
| Bacitracin | + | 10 μg/ml | 498 ± 92 | 192 ± 16 |
| Cephalosporine | – | | | |
| D-cycloserin | – | | | |
| Fosfomycin | (+) | 10 μg/ml | 1.7 ± 0.6 | |
| Moenomycin | – | | | |
| Nisin | + | 10 μg/ml | 423 ± 16 | 156 ± 8.3 |
| Penicillin G | – | | | |
| Polymyxin B | – | | | |
| Ramoplanin | + | 5 μg/ml | 422 ± 60 | 144 ± 12 |
| Tunicamycin | + | 50 μg/ml | 3.1 ± 1.1 | |

TABLE 2-continued

Inducers of liaI expression

| inducer | disk-diffusion assay[1] | conc.[2] [μg/ml] | fold induction (BFS2470)[3] | (HB0950)[3] |
|---|---|---|---|---|
| Vancomycin | + | 2 μg/ml | 63 ± 2.7 | 36 ± 0.2 |
| Other antibiotics[4] | | | | |
| Chloramphenicol | – | | | |
| kanamycin | – | | | |
| rifampicin | – | | | |
| spectinomycin | – | | | |
| streptomycin | – | | | |
| tetracycline | – | | | |
| Detergents | | | | |
| SDS | – | | | |
| Triton | – | | | |
| Organic solvents | | | | |
| Diphenyl ether | n.t. | 10 μl/ml | 10.8 ± 3.4 | |
| n-hexane | n.t. | 10 μl/ml | 7.8 ± 1.2 | |
| cyclo-octane | n.t. | 10 μl/ml | 11.6 ± 4.9 | |
| Surfactants[5] | | | | |
| BDMDDA-Br | – | | | |
| BDMHDA-Cl | + | 10 μg/ml | 8.2 ± 1.9 | |
| HDTMA-Br | – | | | |
| Uncouplers[5] | | | | |
| CCCP | – | | | |
| DNP | – | | | |
| Lysozyme | – | | | |

[1]Qualitative screen of β-Galactosidase activity by appearance of a blue ring around the edge of the zone of inhibition on LB plates supplemented with X-Gal, using strain BFS2470.
"–": no induction,
"+": induction of yvql expression, "n.t.": not tested.
[2]The concentration resulting in the highest level of induction was used.
[3]Quantitative β-Galactosidase assay in liquid, using the pMUTIN-derived (strain BFS2470) and pJPM122-derived minimal promoter system (strain HB0950). Cells were cultured in LB medium to mid-log phase and induced by addition of the drug to be tested to the final concentration given. Cells were harvested and the assay was performed as described-. Results are expressed as foldchanges relative to uninduced control. The background activity for the uninduced samples was about 3-5 and 0.5 Miller units, respectively. Strains according to Table 6.
[4]These findings are in agreement with a recent proteomic study on antibiotic-dependent induction in Bacillus subtilis (3).
[5]BDMDDA-Br, Benzyldimethyldodecylammonium bromide; BDMHDA-Cl, Benzyldimethylhexadecylammonium chloride; HDTMA-Br, Hexadecyltrimethylammonium The ~65-fold induction by vancomycin correlates well with the data previously obtained by microarray analysis (Cao et al., 2002, Mol Microbiol. 45: 1267-1276, the entire teaching of which is incorporated herein by reference). Tunicamycin only resulted in a three-fold induction for liaI expression under these conditions. Nisin and ramoplanin were both strong inducers (420 fold, results not shown), however, the strongest effect was obtained with bacitracin, leading to a >500-fold and 90-fold increase in liaI and liaH expression, respectively.

The pMUTIN-insertion results in a disruption of the targeted gene and generates a transcriptional fusion to lacZ thereby allowing detection of both antibiotic sensitivity (as defined by the zone of inhibition around the disk) and inducibility (by the formation of a blue ring at the edge of the zone of inhibition) (Cao et al., 2002, Mol Microbiol. 45: 1267-1276, the entire teaching of which is incorporated herein). The disruption of liaI and liaH had no effect on the sensitivity of the mutants to any of the antibiotics tested. However, vancomycin, bacitracin, nisin, ramoplanin, and, to a lesser extent, tunicamycin and fosfomycin induced the expression of the two genes (data not shown). Equivalent levels of induction were also observed with the $P_{liaI-74}$-cat-lacZ fragment (in HB0950), albeit with lower fold-changes (See, Table 2). While the mode of action is different for these antibiotics, all four interfere with the lipid II cycle, essential for the biosynthesis of cell envelope polymers (Lazar et al., 2002, Curr. Opin. Chem. Biol. 6: 786-93).

FIG. 5 is a functional dissection of $P_{liaI}$, including an extensional mapping of the liaI transcriptional start site (FIG. 5a) and the intergenetic sequence (FIG. 5b), and a graphical representation of the intergenetic sequence (FIG. 5c). All features are marked underneath the respective line of sequence and the end of yvqJ and the beginning of liaI are labeled. The putative yvqJ terminator is indicated by the black arrows and marked "term." The expression signals for liaI are labeled ('–35', '–10' for the promoter, and 'RBS' for the putative ribosome binding site). A direct repeat sequence is boxed. The 5'-ends of the fragments used for the promoter dissection are marked and labeled according to their position relative to the transcriptional start site. The minimal bacitracin-inducible promoter fragment, based on the promoter dissection is underlined.

FIG. 5d illustrates cultures of the $P_{liaI}$-reporter strains HB0940 (–29), HB0941 (–58), HB0942 (–74), HB0943 (–83), and HB0944 (–193) that were grown to mid-logarithmic phase ($OD_{600}$~0.45) and induced by the addition of bacitracin (final concentration 10 μg/ml). β-Galactosidase activity, plotted on a logarithmic scale for clarity, is expressed in Miller units. Dark gray bars represent the induced sample and light gray bars represent the un-induced control sample for each strain.

To analyze the specificity of the system further, several detergents and surfactants were tested. Detergents like sodium dodecylsulfate (SDS) and Triton X100 damage the cytoplasmic membrane by compromising its integrity. Surfactants serve as emulsifiers by adsorbing and altering the conditions at interfaces due to their amphiphatic nature. Detergents did not induce liaI expression. Of the three surfactants chosen for the analysis, only BDMHDA-Cl (Benzyldimethylhexadodecylammonium chloride) moderately induced liaI expression. Organic solvents are toxic because they nonspecifically accumulate in and disrupt the cytoplasmic membrane. Lysozyme, which breaks the glycosidic bonds between N-acetyl-muramine and N-acetylglucosmine in peptidoglycan, was also ineffective as an inducer.

The genetic organization indicates that liaI is part of a two-gene operon with liaH. The gene liaI codes for a hydrophobic, 126 amino acid protein that is likely localized to the cell membrane. The product of the liaH gene shows significant similarity to phage-shock proteins such as PspA of E. coli. PspA is thought to be involved in the maintenance of cell membrane integrity and proton-motive force, and is induced by uncouplers such as CCCP and DNP. Although these uncouplers were included in the screening, neither elevated liaIH expression. No obvious promoter structure was found upstream of liaH and no significant liaIH expression could be detected in un-induced cultures.

FIG. 6a shows the expression of the liaIHGFSR locus of B. subtilis. The pspA-homolog liaH is shown in black, genes coding for proteins with unknown function are shown in grey, and genes flanking the lia locus are white. The line corresponds to a size of 7.5 kb. In the course of this work, two errors were noted in the original genome sequence in the non-coding region between liaH and liaG. The corrected sequence resulted in an addition of 150 nucleotides at the 5'-end of liaG.

The Northern blots for liaH and liaG are shown in FIG. 6b. Expression of both genes was measured using 10 μg of total RNA from each sample separated on a 1% formaldehyde gel. RNA was transferred to a nylon membrane and hybridized with radio-labeled DNA fragments of the indicated genes. In the figure, "−" represents the un-induced control lane and "+" represents the RNA sample from cultures induced with bacitracin for 15 min (final concentration 10 μg/mL). The two transcripts are marked with black triangles and the approximate size corresponding to liaIH (1.1 kb) and the whole lia locus (~4 kb) is given. The thin band in between represents an artifact derived from quenching of the 4 kb transcript by the abundant 23S rRNA, which can saturate available binding sites on the hybridization membrane.

Figure 7:
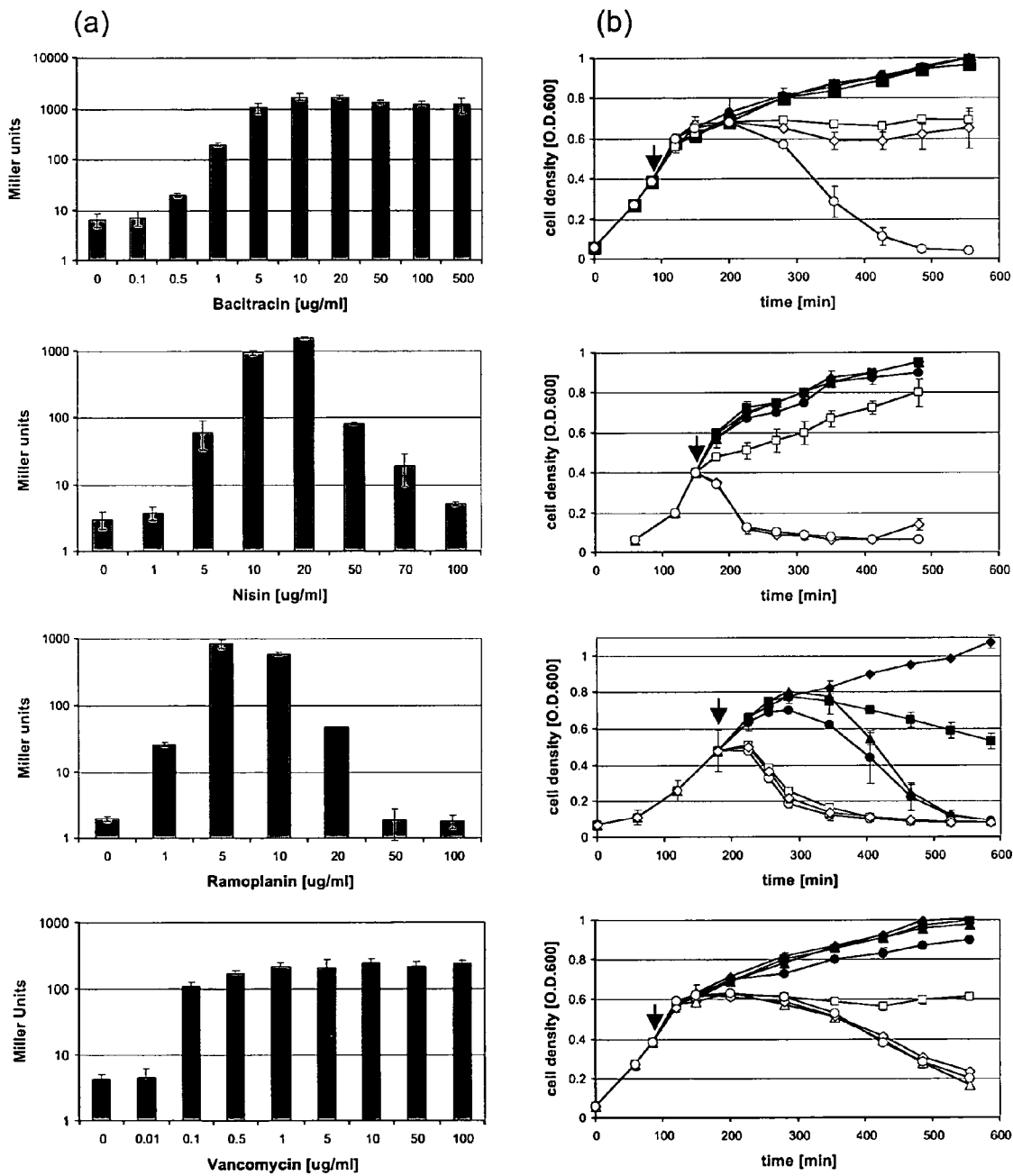
FIG. 7(*a*) shows concentration dependent induction of LiaI and optical density changes for *bacillus subtilis* cultures treated with bacitracin, nisin, ramoplanin and vancomycin in a β-galactosidase assay, using strain BFS2470. Miller units are plotted on a logarithmic scale for clarity.

Concentration-dependent induction/killing experiments were performed for bacitracin, nisin, ramoplanin and vancomycin as shown in FIG. 7. In all four cases the induction of liaI occurred in a concentration-dependent manner (FIG. 7a), reaching a maximum at an antibiotic concentration of about 10 μg/ml (1 μg/mL for vancomycin). The time of antibiotic addition is indicated by an arrow. The antibiotic concentrations affecting the induction of $P_{liaI}$ according to the β3-galactosidase assay are indicated by white symbols. The corresponding concentrations are: bacitracin (50, 100 and 500 μl/mL), nisin (50, 70 and 100 μg/ml), ramoplanin (20, 50 and 100 μg/mL) and vancomycin (5, 10, 50 and 100 μg/mL).

While lacZ-expression remained elevated at higher concentration of bacitracin and vancomycin, a strong decrease down to un-induced levels was observed for nisin and ramoplanin. This finding correlates well with the bactericidal effects of these antibiotics as inferred from the dramatic decrease of optical density: there is little effect of bacitracin and vancomycin on cell growth during the first 30-60 min after addition even at high concentrations (FIG. 7b). In contrast, high concentrations of nisin and ramoplanin led to rapid cell lysis, which likely interfered with the induction of β-galactosidase (FIG. 7b).

Some of the induced genes were targets of two alternative σ factors: (CF, an ECF σ factor, and $σ^B$, the regulator of the general stress response. The most strongly induced gene of the $σ^M$ regulon was bcrC, showing a ~10-fold increase in expression both at 5 and 15 min post induction. BcrC is homologous to membrane spanning proteins of ABC transporters and has been reported to be a bacitracin-resistance determinant in two independent studies (Cao and Helmann, 2002, *J. Bacteriol.* 184: 6123-6129; Ohki et al., 2003, *J Bacteriol.* 185: 51-59, the entire teachings of which are incorporated herein by reference).

Whereas the $σ^M$ regulon showed similar induction ratios 5 and 15 minutes after bacitracin-addition, the general stress response was more strongly induced at the early time point, with a significant decrease in expression by 15 min after addition of bacitracin. The same bias towards an early response was observed for the three genes of the ZneR regulon that code for zinc-efflux functions. This induction was likely due to the use of the zinc salt of bacitracin for this study, which is the biologically most active form of bacitracin (Adler and Snoke, 1962, *J Bacteriol.* 83: 1315-1317, the entire teaching of which is incorporated herein by reference). The final concentration of Zn-bacitracin (100 μg/mL) corresponds to 67.3 μM $Zn^{2+}$. The ZneR regulon has been shown to be induced above 10 μM $Zn^{2+}$.

In addition to liaIH, the genes most strongly induced by bacitracin were bceAB, formerly ytsCD (280-fold at 5 min/360-fold at 15 min) and yvcRS (12/24-fold), both coding for ABC transporters, and the yhcYZIyhdA locus (20/14-fold), encoding a two-component system and an azoreductase homologue, respectively. The four genes directly downstream of liaIH, yvqGFEC, were also significantly induced (6-/7-fold) by bacitracin.

A number of additional genes showed a delayed response to bacitracin addition, with significant induction only after 15 min (Table 1). The ygaCD genes encode proteins with homology to the membrane-spanning and nucleotide-binding domains of bacterial ABC transporters (Higgins, 2001, *Research in Microbiology.* 152: 205-210, the entire teaching of which is incorporated herein by reference). There are no defined homologs in the database for the products of ytzB and yetG. The ykuNOP locus is weakly induced, together with other members of the Fur regulon (Baichoo et al., 2002, *Mol Microbiol.* 45: 1613-1629, the entire teaching of which is incorporated herein by reference). This induction is likely an indirect effect due to elevated zinc levels.

Figure 8:
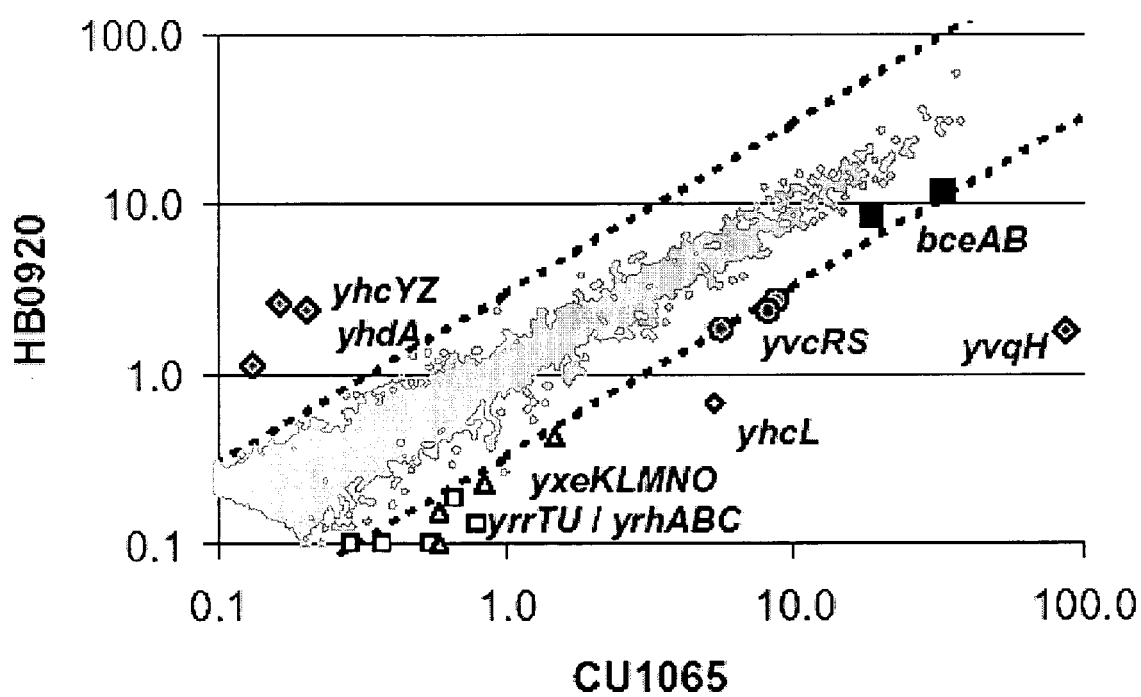
FIG. 8 illustrates gene expression in the liaH mutant HB0920 compared to gene expression in the isogenic wild-type strain CU1065 after bacitracin induction (5 min)

The bacitracin stimulon in the wild-type strain CU1065 was qualitatively similar to that of the liaH-deletion mutant HB0920 as judged by a comparison of the induction profile at 5 min, as illustrated in FIG. 8. This dataset was filtered prior to plotting in order to exclude non-expressed genes as well as non-reproducible signals and control spots. Relative hybridization intensities are plotted for genes as measured for CU1065 (x axis) and HB0920 (y axis). The dotted lines correspond to a +/− threefold difference in signal intensity. Signals showing significant variations are highlighted and labeled.

The most noteworthy difference was the yhcYZIyhdA locus, which was not induced by bacitracin in the wild type, but showed a 20-fold increase of expression in HB0920. This locus is therefore a candidate for negative regulation by LiaH. In addition, expression of the bacAB and yvcRS loci was threefold greater in CU1065 than in the liaH mutant when both were measured 5 min after bacitracin treatment. These minor differences (compared to the overall induction rate for these loci) may be due to slight variations between samples.

Figure 9:
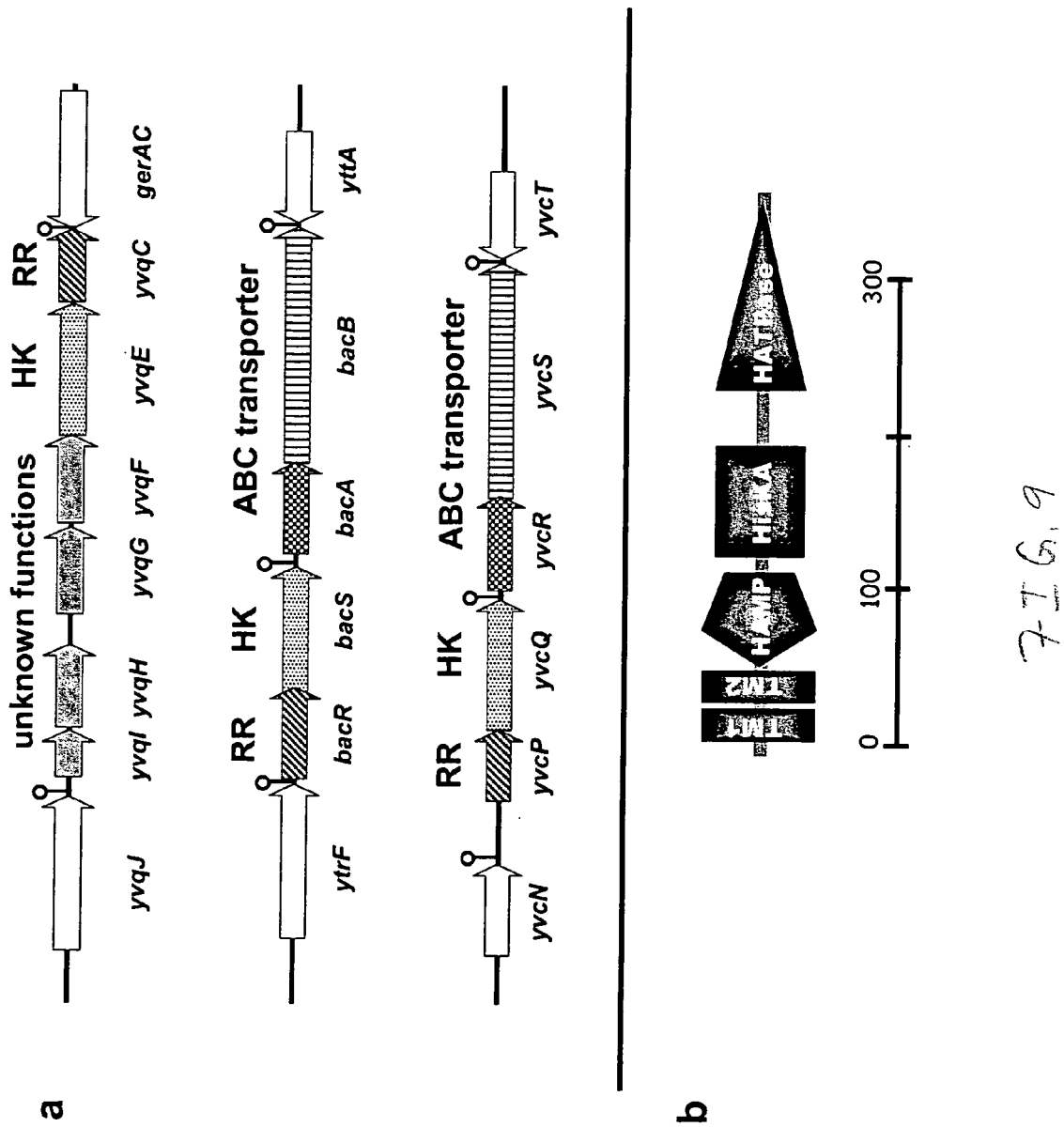
FIG. 9(*a*) is a graphic representation of the liaIHGFEC, bacRSAB, and yvcPQRS regions on the chromosome.

The regulatory network of the bacitracin stimulon includes three two-component systems. The microarray experiments demonstrated a very strong transcriptional response of the liaIH (GFEC), bceAB and yvcRS loci to bacitracin. Candidate regulators have been identified for these genes based on the observation that in each case adjacent genes encode a two-component regulatory system, as illustrated in FIG. 9a. Hatched arrows represent response regulators (RR), dotted arrows represent histidine kinases (HK), checkered arrows represent the nucleotide-binding domains of ABC transporters, and striped arrows represent the membrane-spanning domains of ABC transporters. Unknown genes are shown in gray and the genes flanking the region of interest are shown in white. Predicted rho-independent transcription terminators are indicated by stem-loops. The line corresponds to a size of 7.5 kb for all three regions.

Moreover, it has been shown previously that over-expression of these response regulators induces expression of the linked genes coding for the ABC-transporters (Joseph et al., 2002, *J Mol Microbiol Biotechnol.* 4: 503-513, the entire teaching of which is incorporated herein by reference). This finding was confirmed in DNA microarray studies which additionally suggested that YvcP might regulate the bceAB genes and that YxjL might contribute to induction of the liaIH(GFEC) locus (Kobayashi et al., 2001, *J Bacteriol.* 183: 7365-7370, the entire teaching of which is incorporated herein by reference).

The bacitracin-sensing histidine kinases (FIG. 9b) share an unusual N-terminal sensing domain and are linked to ABC transporters in Gram-positive bacteria with a low G+C content. Most histidine kinases are modular transmembrane proteins with an extracellular input domain and a cytoplasmic transmitter domain (Parkinson, 1993, Cell. 73: 857-871, the entire teaching of which is incorporated herein by reference). Due to the diversity of stimuli sensed, the N-terminal domains of histidine kinases show almost no sequence similarity in contrast to the highly conserved C-terminal transmitter domain that harbors the universal phosphorylation activity common to all members of this protein family. Analysis of the three bacitracin-sensing histidine kinases (BceS, LiaS and YvcQ) revealed an unusually short N-terminal domain (~60-70 amino acids) for all three proteins due to the almost complete lack of a linker region between the two deduced transmembrane helices (BceS, LiaS: <5 amino acids, YvcQ: ~15 amino acids).

Figure 10:
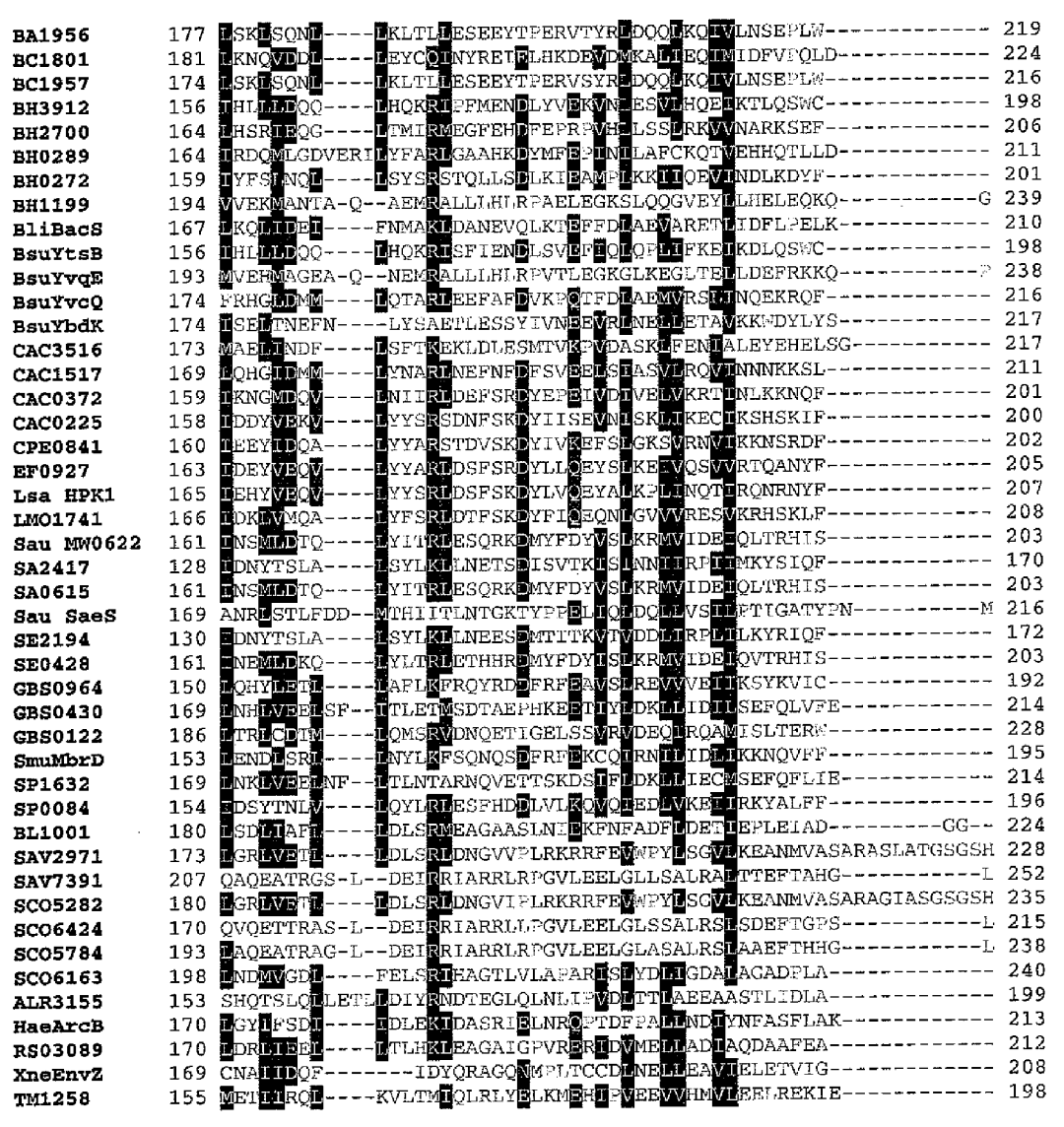

The apparent lack of an extracytoplasmic signal input domain in the bacitracin-sensing kinases results in an overall protein length of 360 amino acids or less, compared to about 450 amino acids for most EnvZ-like histidine kinases. To identify other sensor kinases with a similar domain structure a simple modular architecture research tool was employed (Schultz et al., 1998, Proc Natl Acad Sci USA. 95: 5857-5864, the entire teaching of which is incorporated herein by reference). The sequence of BacS and LiaS, which belong to two different sub-classes of histidine kinases (Grebe and Stock, 1999, Adv Microb Physiol. 41: 139-227, the entire teaching of which is incorporated herein by reference), were used as matrices to identify histidine kinases with a similar overall domain organization (FIG. 10). The alignment was generated using ClustalW from the Bioedit package (Hall, 1999, Nucl. Acids. Symp. Ser. 41: 95-98). Two partially overlapping groups of 1905 and 667 histidine kinases, respectively, were retrieved. The resulting pool of proteins was filtered to identify those of less than 400 amino acids total length with an N-terminal domain of not more than 100 amino acids, including 2 putative transmembrane helices with no more than 20 amino acids spacing. Only 45 sensor kinases fit these criteria (Table 3), including BacS and MbrD, two histidine kinases known to be linked to bacitracin resistance in B. licheniformis and Streptococcus mutans, respectively (Neumuller et al., 2001, Eur J Biochem. 268: 3180-3189; Tsuda et al., 2002, Antimicrob. Agents Chemother. 46: 3756-3764, the entire teachings of which are incorporated herein by reference). Based on their unusual topology, it appears that these 45 proteins define a unique sub-family of intramembrane-sensing histidine kinases. Remarkably, 90% of these histidine kinases (40/45) were found in Gram-positive bacteria (Table 4).

TABLE 3

Histidine Kinases with domain organization similar to Bacs and YvqE of *Bacillus subtilis*

| Organism | Histidine Kinase | ACC-Nr. | length [aa] | TM spacing (1) | ABC transporter (2) | function | Reference |
|---|---|---|---|---|---|---|---|
| *Bacillus* | | | | | | | |
| B. anthracis | BA1956 | AAP25850 | 351 | 8 | no | unknown | genome |
| B. cereus | BC1801 or VanS | AAP08775 | 358 | 12 | no | unknown | genome |
| | BC1957 | AAP08928 | 348 | 10 | yes | unknown | genome |
| B. halodurans | BH3912 | BAB07631 | 334 | 9 | yes | unknown | genome |
| | BH2700 | BAB06419 | 343 | 10 | yes | unknown | genome |
| | BH0289 | BAB04008 | 346 | 7 | yes | unknown | genome |
| | BH0272 | BAB03991 | 331 | 14 | yes | unknown | genome |
| | BH1199 | BAB04918 | 351 | 16 | no | unknown | genome |
| B. llcheniformis | BacS | AAD21212 | 348 | 7 | yes | ▓▓▓ | Neumueller et al. (2001) |
| B. subtillis | YvcQ | CAB15476 | 356 | 15 | yes | unknown | this study. Joseph et al. (2002) |
| | YbdK | CAB11995 | 320 | 19 | no | unknown | genome |
| | YtsB | CAB15017 | 334 | <5 | yes | ▓▓▓ | this study. Joseph et al. (2002) |
| | YvqE | CAB15299 | 360 | 6 | no | ▓▓▓ | this study |
| *Clostridum* | | | | | | | |
| C. acetobutylicum | CAC3516 | AAK81442 | 350 | 11 | yes | unknown | genome |
| | CAC1517 | AAK79484 | 349 | 9 | yes | unknown | genome |
| | CAC0372 | AAK78352 | 334 | 8 | yes | unknown | genome |
| | CAC0225 | AAK78206 | 339 | 15 | yes | unknown | genome |
| C. perfringens | CPE0841 | BAB80547 | 336 | <5 | no | unknown | genome |
| Enterococcus faecalis | EF0927 | AAO80735 | 341 | 8 | yes | unknown | genome |
| Lactobacillus sakei | HPK1 | AAD10259 | 339 | 14 | yes | unknown | genome |
| Listeria monocytogenes | LMO1741 | CAC99819 | 346 | 9 | yes | unknown | genome |
| *Staphylococcus* | | | | | | | |
| S. aureus | SA0615 or MW06 | BAB94487 | 346 | 9 | yes | unknown | genome |
| | SA2417 | BAB58786 | 295 | 6 | yes | unknown | genome |
| | SaeS | AAD48403 | 353 | 7 | no | exoprotein prod. | Glraudo et al. 1999/2003 |
| S. epidermidis | SE2194 | AAO05836 | 298 | <5 | yes | unknown | genome |
| | SE0428 | AAO04025 | 346 | 7 | yes | unknown | genome |

TABLE 3-continued

| | | | | | | | |
|---|---|---|---|---|---|---|---|
| *Streptococcus* | | | | | | | |
| *S. agalactiae* | GBS0964 | CAD46623 | 312 | 9 | yes | unknown | genome |
| | GBS0430 | CAD46074 | 345 | 10 | no | unknown | genome |
| | GBS0122 | CAD45767 | 356 | 6 | yes | unknown | genome |
| *S. mutans* | MbrD | BAB83946 | 317 | <5 | yes | | Tsuda et al. 2002 |
| *S. pneumoniae* | HK01 or SP1632 | CAB54567 | 324 | <5 | no | unknown | Lange et al. (1999) |
| | HK08 or SP0084 | CAB54579 | 350 | 10 | yes? | unknown | Lange et al. (1999) |
| *Bifidobacterium longum* | BL1001 | AAN24809 | 356 | 6 | no | unknown | genome |
| *Streptomyces* | | | | | | | |
| *S. avermitiris* | SAV2971 | BAC70682 | 368 | 10 | no | unknown | genome |
| | SAV7391 | BAC75102 | 388 | 5–15 | no | unknown | genome |
| *S. coalicolor* | SCO5282 | CAC04497 | 375 | 10 | no | unknown | genome |
| | SCO6424 | CAA18911 | 331 | 12 | no | unknown | genome |
| | SCO5784 | CAA18321 | 358 | 8 | no | unknown | genome |
| | SCO6163 | CAA22397 | 303 | <5 | no | unknown | genome |
| *Anabaena* sp. | ALR3155 | BAB74854 | 344 | 17 | yes | unknown | genome |
| *Haemophilus influenzae* | Arc8 | P44578 | 325 | 10 | no | aerobic respiration? | genome |
| *Ralstonia solanacearum* | RS03089 | CAD18605 | 365 | 16 | yes | unknown | genome |
| *Xhenorabdus nematophilius* | EnvZ | AAB36612 | 342 | 8 | no | osmo-sensing | Tabatabai and Forst (1995) |
| *Thermotoga maritima* | TM1258 | AAD38332 | 319 | 8 | yes | unknown | genome |

(1) Estimated number of amino acids between TM1 and TM2 (see FIG. 3b).
(2) Localization of the two-component system corresponding to the Histidine Kinase in direct vicinity to genes coding for ABC transporters.

TABLE 4

Histidine Kinases with domain organization similar to BacS (YtsB) and YvqE (as shown below) of *Bacillus subtilis*

| bacterial group | number of kinases[1] | ABC transporter[2] |
|---|---|---|
| Gram-positive, low G + C | 33 | 24 |
| Gram-positive, high G + C | 7 | 0 |
| Gram-negative | 4 | 2 |
| Archaea | 1 | 1 |

[1] parameters of all kinases: 400 amino acids (aa) maximum length, 100 aa N-terminal domain with two putative transmembrane domains with max. 20 aa spacing. The overall domain organization is exemplified for YvqE below (size in aa). Note that not all identified histidine kinases have a HAMP domain.
[2] Two-component systems corresponding to the identified histidine kinases with an ABC transporter homolog located directly up- or downstream on the chromosome.

Figure 11:
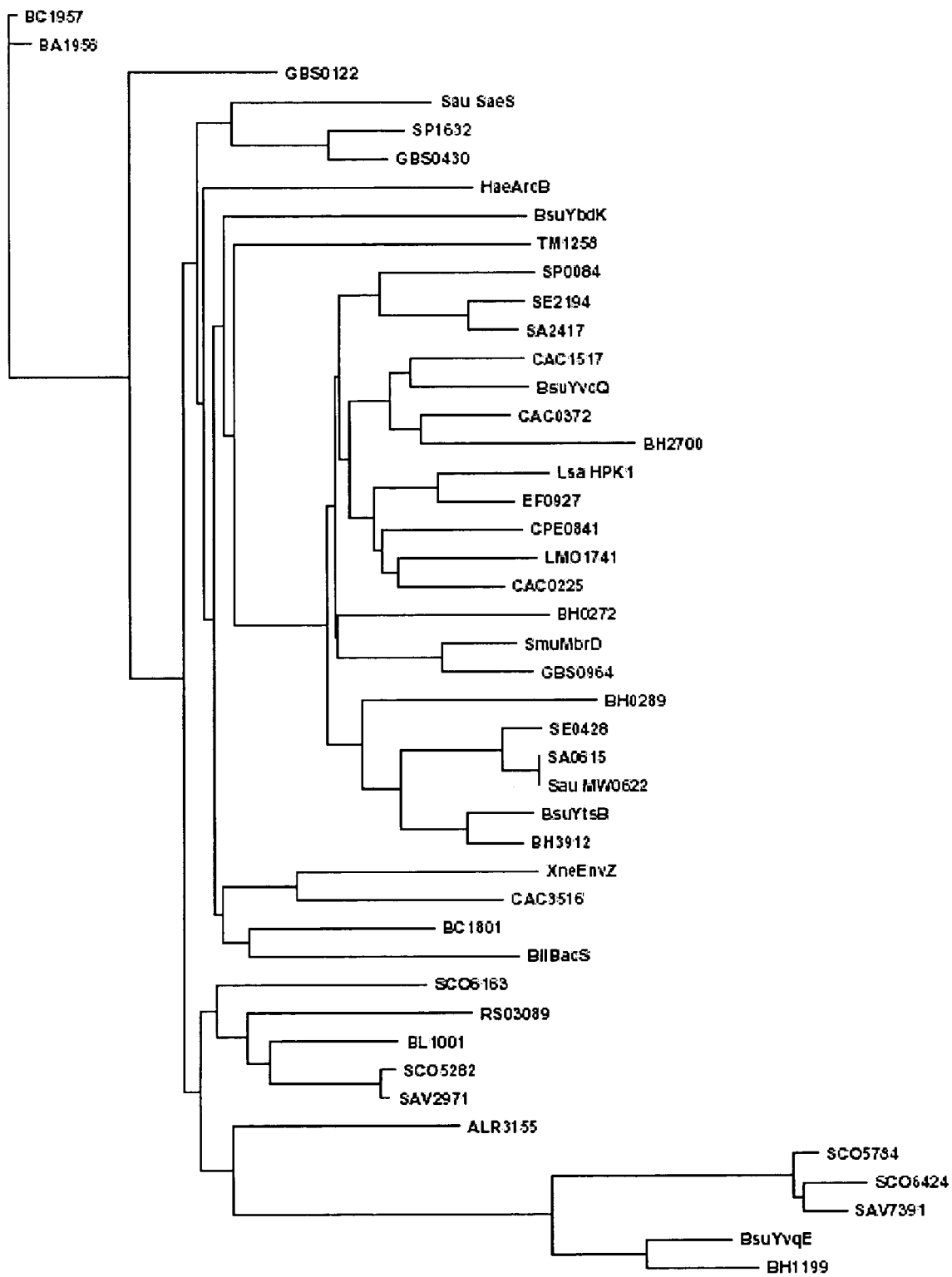
FIG. 11 is a phylogenetic tree derived from the alignment of FIG. 10.

It was observed that, like the *B. subtilis* BceRS-BceAB and YvcQP-YvcRS, the bacitracin-sensing two-component systems of *B. licheniformis* and *S. mutans* are genetically linked to an ABC-transporter. To determine if this genetic linkage is a common feature, the adjacent chromosomal regions for all 45 identified two-component systems was analyzed (Table 5). Consistent with a previous analysis (Joseph et al., 2002, *J Mol Microbiol Biotechnol.* 4: 503-513, the entire teaching of which is incorporated herein by reference), investigators found adjacent ABC transporter gene clusters in the *Bacillus/Clostridium* group (low G+C) of Gram-positive bacteria (24/33), but not in the high G+C group (0/7). Multiple sequence alignment and the resulting phylogenetic tree (FIG. 11) demonstrate a close evolutionary relationship among this subset of histidine kinases that are encoded adjacent to ABC transporters. However, the three histidine kinases involved in bacitracin-resistance in *B. licheniformis, S. mutans* and *B. subtilis* are not tightly clustered within this group (FIGS. 10 and 11; Neumuller et al., 2001, *Eur J Biochem.* 268: 3180-3189; Tsuda et al., 2002, *Antimicrob. Agents Chemother.* 46: 3756-3764, the entire teaching of which is incorporated herein by reference).

TABLE 5

Strains used in this study (SEQ ID NOS: 8-67 respectively, in order of appearance)

| strain | genotype* | reference, source, or primers used for construction |
|---|---|---|
| HB0031 | sigM::kan | Cao et al. (2002a) |
| HB0106 | bcrC::pMUTIN | Cao et al. (2002b) |
| BFS2469 | yvqH::pMUTIN | Zoltan Pragai (Harwood lab) |

TABLE 5-continued

Strains used in this study (SEQ ID NOS: 8-67 respectively, in order of appearance)

| strain | genotype* | reference, source, or primers used for construction |
|---|---|---|
| BFS2470 | yvqI::pMUTIN | Zoltan Pragai (Harwood lab) |
| HB0920 | yvqH::kan | up: CCTTTGGTGCCGCAGTCAGTGC, *CCTATCACCTCAAATGGTTCGCTG*GTCCTTCATGAACTGACGC<br>do: *CGAGCGCCTACGAGGAATTTGTATCG*CAGACCAGACAAAAGCGG, CGCTAGATCCCCGCTGTCC |
| HB0922 | ycgRQ::kan | up: GACAGGCAAGGGAACTCCGATCC, *CCTATCACCTCAAATGGTTCGCTG*GATTCCGGAAAGTATGACGCC<br>do: *CGAGCGCCTACGAGGAATTTGTATCG*CCATTCAAGTCAACTCTCC, GTACGAGACCTCCTTCCATGTCG |
| HB0923 | ydhK::tet | up: CGAAAGTGGAATGTGACCAGG, *CCACGCTTACTACGTTGATAAGC*ATAACATCAGAATTCCCAGTGC<br>do: *GGGATCAACTTTGGGAGAGAGTTC*AATGGGTCACAGAAGATGAGC, GCAACACTGATGGTATCTAGGG |
| HB0924 | ygaCD::cat | up: CCAAGGCTGACATGATCCGC, *CTTGATAATAAGGGTAACTATTGCC*CTCCTTCCTTGGGATAGCCC<br>do: *GGGTAACTAGCCTCGCCGGTCCACG*ACTCATGGACTATGAGAGCC, GCTGTGATTGCCACAGTGTTCG |
| HB0925 | ykvS::kan | up: GTCTCTTCTATGCTTAGACGGC, *CCTATCACCTCAAATGGTTCGCTG*CTGAGAGTCCAGAAAGAGC<br>do: *CGAGCGCCTACGAGGAATTTGTATCG*GATCATGGATAACTATCGG, CACATGCTACTTGATAGCAGGG |
| HB0926 | ytrBCDEF::cat | up: ACGTAACGTGCCAATGCTGATTGC, *TTGATAATAAGGGTAACTATTGCC*GGCCGTCAATCGCTTTTGACA<br>do: *GGGTAACTAGCCTCGCCGGTCCAC*AAGCTACCAAAACCAACGTGC, GCTTGGATTTTCGCGATCAGCACA |
| HB0927 | bacR(ytsA)::cat | up: GGGAAGAGTCGCAAAGTCGG, *GGGTAACTAGCCTCGCCGGTCCACG*GCAAAACGCCAGCATGCGC<br>do: *CTTGATAATAAGGGTAACTATTGCC*GACCGTCAATGTCAATCGCC, GACGCTTGATCATGGTGATCCG |
| HB0928 | bacAB(ytsCD)::kan | up: GAGAACAATCTCGATGTGACAGCC, *CCTATCACCTCAAATGGTTCGCTG*CGATGCCCTTCAGCACTTCC<br>do: *CGAGCGCCTACGAGGAATTTGTATCG*ATATACTGCGCTCTACTCC, CTCCGTACGAATCCAGTTATCATAGC |
| HB0929 | ytzB::kan | up: GAACGAATTCCCTCATTCCGC, *CCTATCACCTCAAATGGTTCGCTG*GCACCTCCTGGTTGATCGTAC<br>do: *GAGCGCCTACGAGGAATTTGTATCG*GTCATTGATACAATCGCCTC, GATATCCAAGGAACTGGCGC |
| HB0931 | yvcP::tet | up: ATGGCTGTCTGCGGAAAACGGCG, *GGGATCAACTTTGGGAGAGAGTTC*CAAGCAGCACAAGATCAGGC<br>do: *CCACGCTTACTACGTTGATAAGC*CAATCGGAAGGATGAAGCGG, GCCTCTTTATGGTTCGTCCG |
| HB0932 | yvcRS::cat | up: GCTTGCAGAACAAGCCTCTTCTTCG, *CTTGATAATAAGGGTAACTATTGCC*GGCGCTGAGCGCTTGGTATG<br>do: *GGGTAACTAGCCTCGCCGGTCCACG*GCGTGCTGTTCTTCAGCG, CCGATTCCTGAAGAGATTGAAGC |
| HB0933 | yvqC::kan | up: GCTGTCATCAAGCTGGTTCGG, *CCTATCACCTCAAATGGTTCGCTG*CGATGCTTCGCCGATGACTTC<br>do: *CGAGCGCCTACGAGGAATTTGTATCGG*CACACCGAAATCATCTCG, CTCTTCATCTGATCCGACACAGC |
| HB0934 | yvqGFEC::kan | up: TTAGGAGGAATCAGGTATGG, *CCTATCACCTCAAATGGTTCGCTG*CCGGACATCCTTGCTATCCG<br>do: *CGAGCGCCTACGAGGAATTTGTATCGG*CACACCGAAATCATCTCG, CTCTTCATCTGATCCGACACAGC |
| HB0935 | yvqlH::tet | up: GAATCTCAATCAGAGTCTGCGG, *GGGATCAACTTTGGGAGAGAGTTC*TGCGTATGTCATCAAGCTCCC<br>do: *CCACGCTTACTACGTTGATAAGC*ATCAGACCAGACAAAAGCGGC, CGCTAGATCCCCGCTGTCC |
| HB0936 | yxjL::tet | up: CATCCCTATGTGGCATCCACTGC, *CCACGCTTACTACGTTGATAAGC*ATCATCGGCAAGCGCTACGCG<br>do: *GGGATCAACTTTGGGAGAGAGTTCA*AGACCGGACACAGGCAGTCG, AGTCTCTGATAATGTAGTGGAGC |
| HB0937 | bcrC::pMUTIN,<br>bacAB::kan | this study |

*all strains are derivatives of *B. subtilis* strain CU1065 (W168 trpC2 auSPβ)

Figure 12:
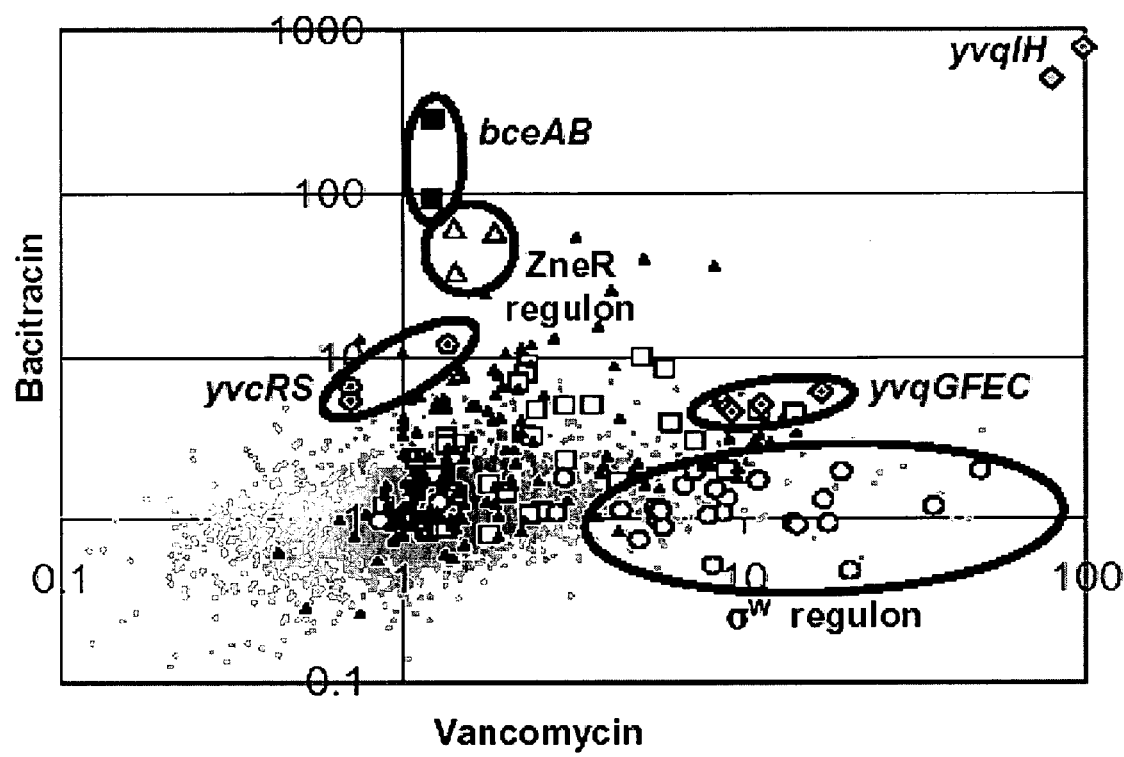
FIG. 12 is a graphical comparison of the vancomycin (x axis) and bacitracin (y axis) stimulon of CU1065.

Comparison between the bacitracin and vancomycin stimulons was made. In a previous study the vancomycin stimulon was examined (Cao et al., 2002, *Mol Microbiol.* 45: 1267-1276, the entire teaching of which is incorporated herein by reference). To gain an understanding of the spectrum and specificity of the cell wall stress responses of *B. subtilis*, investigators compared the vancomycin and bacitracin stimulons in a scatter plot (FIG. 12). Both antibiotics induce the $\sigma^M$ and the $\sigma^B$ regulons and, in both cases, liaIH was most strongly induced locus. In contrast, the $\sigma^W$ regulon is induced by vancomycin alone, whereas bceAB, yvcRS and the ZneR-regulon specifically respond to bacitracin.

The comparison between the vancomycin and the bacitracin response is a vital step to differentiate between specific and general cell wall stress responses in *B. subtilis*. In FIG. 12, the most strongly induced gene signals are circled. Members of the $\sigma^M$ (white open squares), $\sigma^W$ (white open circles) and $\sigma^B$ (small black triangles) regulon are highlighted. All other gene signals are represented as small gray diamonds. Note that for the generation of this graphical comparison the data sets could not be filtered to remove low-quality and non-reproducible signals, thus some of the background signals (small gray diamonds) that appear to represent highly regulated genes are not significant.

Figure 13:
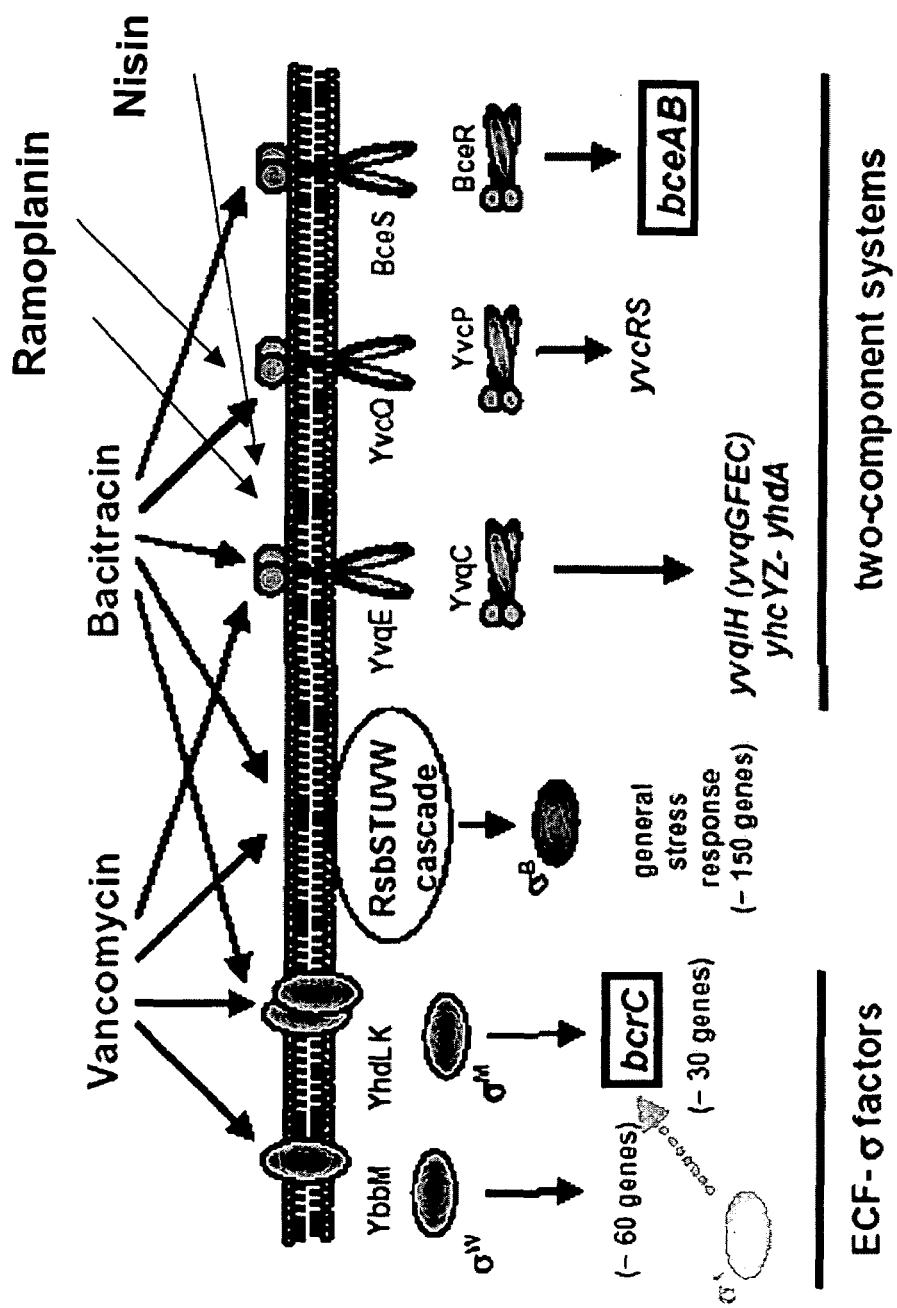
FIG. 13 is a graphical overview of the regulatory network of the cell wall stress response of *Bacillus subtilis*.
Figure 14:
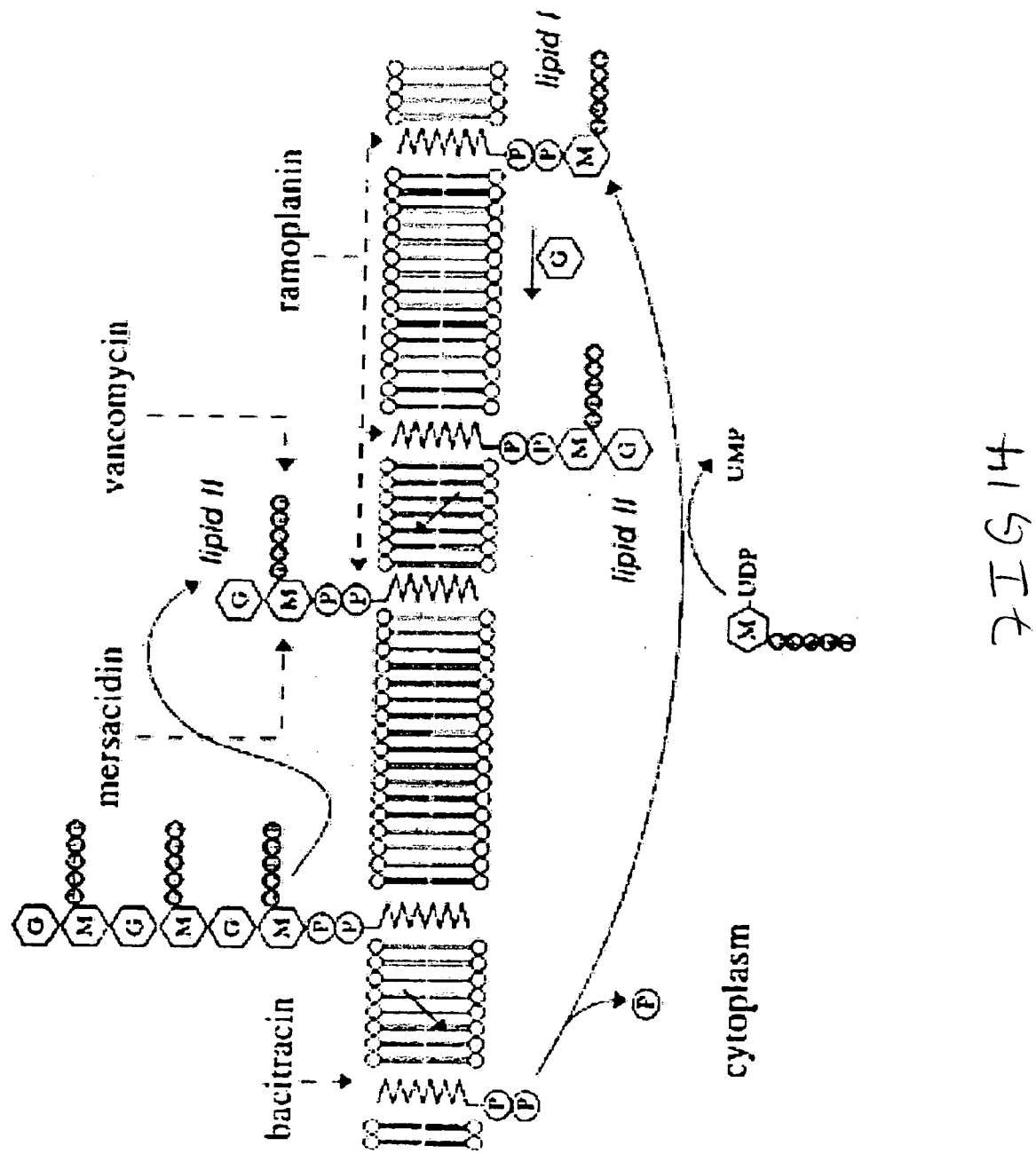
FIG. 14 is a schematic for ramoplanin.

The present inventors determined that the stimulons, further including nisin and ramoplanin, share at least four regulons: the $\sigma^B$-dependent general stress response, the $\sigma^M$-regulon, the LiaR-target genes liaIH(GFEC), and the YvcQ-target genes. FIG. 13 shows the regulatory pathways of the instant invention, indicated by arrows. Identified bacitracin resistance-determinants are boxed. When an antibiotic is applied to a bacterial organism, the first component of each system (LiaS, YvcP, or BceR) is activated and phosphoralates the second component (LiaR, YvcQ, or BceS), which then acts on the promoter region, causing the reporter to be induced (See, FIG. 13).

The general stress response is a strong but transient response to cell wall antibiotic stress, consistent with the known transient nature of σ$^B$ activation in response to other stresses (Hecker and Volker, 2001, *Adv Microb Physiol.* 44: 35-91; Petersohn et al., 2001, *J. Bacteriol.* 183: 5617-5631; Price et al., 2001, *Mol Microbiol.* 41: 757-774, the entire teaching of which is incorporated herein by reference). In contrast, the σ$^M$-regulon shows a constant level of induction under all conditions tested. σ$^M$ is one of seven ECF σ factors in *B. subtilis* (Helmann, 2002, *Adv Microb Physiol.* 46: 47-110, the entire teaching of which is incorporated herein by reference) and its regulon is induced by salt, heat shock, acid, and ethanol stress (Horsburgh and Moir, 1999, *Mol Microbiol.* 32: 41-50; Thackray and Moir, 2003, *J Bacteriol.* 185: 3491-3498, the entire teaching of which is incorporated herein by reference). Several other regulons appear to respond to antibiotic-specific signals. For example, the σ$^W$ regulon is induced by vancomycin, but not by bacitracin. Conversely, the bacAB resistance determinant is selectively induced by bacitracin.

EXAMPLES

Example 1

Bacterial strains and growth conditions: *B. subtilis* was routinely grown in LB medium at 37° C. with aeration. All strains used in this study are derivatives of the laboratory wild type strain CU1065 (W168 trpC2 attSPβ). All strains are listed in Table 5.

Determination of the minimal inhibitory concentration (MIC): MIC-assays were performed in microtiter plates using a 'Tecan Spectra Rainbow' microtiter plate reader. Pre-cultures were inoculated from fresh overnight LB-plates and incubated at 37° C. with aeration until they reached an O.D.$_{600}$≈0.45. Tenfold dilution of these cultures were inoculated in a total volume of 200 μl/well with increasing quantities of bacitracin, ranging from 0.01 to 1000 μg/mL (final concentration). The plates were incubated at 37° C. and the O.D.$_{600}$ was read after 4 hours, when cultures had reached their final cell density. All experiments were performed in triplicate.

Allelic replacement mutagenesis using Long Flanking Homology (LFH)PCR: The LFH-PCR was adapted to generate chromosomal deletions of the genes listed in Table 5. The protocol is modified from the published procedure (Wach, 1996, *Yeast.* 12: 259-265, the entire teaching of which incorporated herein by reference). In brief: resistance cassettes were amplified from a suitable vector as template (Guerout-Fleury et al., 1995, *Gene.* 167: 335-336; Youngman, 1990, the entire teaching of which is incorporated herein by reference). Two primer pairs were designed to amplify ~1000 bp DNA-fragments flanking the gene(s) to be deleted at their 5'- and 3'-end. The resulting fragments are here called 'up' and 'do' fragment. The 3'-end of the up-fragment as well as the 5'-end of the do-fragment extended into the gene(s) to be deleted in a way that all expression signals of genes up and downstream the targeted genes remained intact. Extensions of ~25 nucleotides were added to the 5'-end of the 'up-reverse' and the 'do-forward' primers that were complementary (opposite strand and inverted sequence) to the 5'- and 3'-end of the amplified resistance cassette. All obtained fragments were purified using the PCR-purification kit from Qiagen. Approximately 150-200 ng of the up-fragments and do-fragments and 250-300 ng of the resistance cassette were used together with the specific up-forward and do-reverse primers at the normal concentration in a second PCR-reaction. In this reaction the three fragments were joined by the 25 nucleotide overlapping complementary ends and simultaneously amplified by normal primer annealing. The PCR-products were PCR-purified and directly used to transform *B. subtilis*. Transformants were checked by direct colony-PCR, using the up-forward primer with a reverse primer annealing inside the resistance cassette.

All PCR-reactions were done in a total volume of 50 μl using the HotStar DNA-Polymerase Mastermix from Qiagen. The primers used to amplify the flanking regions for this study are listed in Table 5. As of May 27, 2004, a detailed protocol for the LFH-PCR A, a list of the templates and primers used to amplify the resistance cassettes, and the internal primers used to verify the correct insertions of the cassette in the constructed mutants could be found under "supplemental materials" at in the supplementary material at http://www.micro.cornell.edu/faculty.JHelmann.html. Links: "LFH-PCR.xls"; and "LFH-PCR.doc".

Measurement of induction by β-galactosidase assays: Cells were inoculated from fresh overnight LB-plates and grown in LB-medium at 37° C. with aeration until they reached an O.D.$_{600}$=0.45. 2 mL of cultures were harvested (un-induced control) and the cell pellets were shock frozen and kept at −70° C. The cultures were induced by addition of antibiotics to a final concentration of: bacitracin (100 μg/mL), tunicamycin (50 μg/mL) or vancomycin (2 μg/mL) and incubated for additional 30 min at 37° C. 2 mL of the cultures were harvested as described above (induced sample). The pellets were re-suspended in 1 mL of working buffer and assayed for β-galactosidase activity as described with normalization to cell density (Miller, 1972, the entire teaching of which is incorporated herein by reference).

Preparation of total RNA for Northern blot and microarray analysis: For Northern analysis, total RNA was extracted from 5 mL of *B. subtilis* culture, with and without bacitracin. Bacitracin was added to the culture at O.D.$_{600}$=0.45 (midlog phase) and the cultures were incubated for 15 min at 37° C. with aeration before the cells were harvested and shock-frozen. RNA-preparation was performed using the RNeasy kit (Qiagen) according to protocol.

For microarray analysis 100 mL of LB medium were inoculated from a fresh overnight LB-plate and incubated at 37° C. with aeration until the culture reached an O.D.$_{600}$≈0.45, when the culture was split: 30 mL served as an un-induced control. To the remaining culture bacitracin was added to a final concentration of 100 μg/mL and 30 mL samples were taken 5 and 15 min after addition. The cells were harvested by centrifugation at room temperature and cell pellets were shock frozen and stored at −70° C. for at least 30 min. RNA was extracted using the 'hot phenol method' as described previously (de Saizieu et al., 1998, *Nat Biotechnol.* 16: 45-48, the entire teaching of which is incorporated herein by reference). After extraction the RNA was purified using the RNA clean-up protocol of the RNeasy kit (Qiagen) with on-column DNase treatment in order to remove abundant small RNA molecules (tRNAs and 5S rRNA) and residual genomic DNA.

Probe preparation and Northern blot analysis: Internal fragments of 500-750 nucleotide lengths were amplified by PCR using the following primer pairs: bcrC,

```
SEQ ID NO. 1,
(CCAAGCTTCAGAATCCCCCCAGAAAAAGAATTCGAAGAAAACAA
GAGAT); yvcR, SEQ ID NO. 2, (TATCATACCAAGCGCTC
AGCGCTTGCTGCTGTGGCATCATGCG); bacA,
SEQ ID NO. 3,
```

(CAGGAAGTGCTGAAGGGCATCGCGT-TGCGTTTTTGATTGAGCTGGCTCAGC); liaH, SEQ ID NO. 4, (GGAGGAATCAGGTATGGCTTGACCG-CAAATCCTTCC). The PCR-fragments were purified using the Qiagen PCR-Purification kit and 100 ng of each fragment were labeled with [α-$^{32}$P]dATP (New England Nuclear; 3000 Ci/mmol, 10 mCi/µl) by random oligonucleotide-primed synthesis using the Klenow-fragment of DNA-polymerase (3'→5' exo⁻, New England Biolabs) according to protocol (Current protocols, 3.5.9-10, based on Feinberg and Vogelstein 1983, the entire teaching of which is incorporated herein by reference). Unincorporated [α-$^{32}$P]dATP was removed by NucAway spin columns (Ambion).

Northern analysis was carried out using the NorthernMax formaldehyde-based system (Ambion) according to the instruction manual. In brief: 10 µg total RNA were denatured and loaded on a 1% formaldehyde agarose gel. After electrophoresis, the RNA was transferred to Zeta-Probe blotting membrane (Bio-Rad) in a downward transfer setup. The RNA was cross linked by exposing the damp membrane to UV-light (1 min at λ=302 nm). The blot was pre-hybridized at 42° C. for 30 min and the labeled probe (preheated to 95° C. for 10 min) was added to the hybridization tube. Hybridization was performed overnight at 42° C. On the next day the membrane was washed twice with low stringency buffer (2×SSC) at room temperature for 5 min followed by two high-stringency washes (0.1×SSC at 42° C. for 15 min). The blot was wrapped in plastic wrap, exposed to a phosphor screen (Molecular Dynamics) and analyzed using a Phosphor Imager (Molecular Dynamics).

Microarray analysis: DNA microarrays contained 4,020 B. subtilis genes and consisted of PCR products printed in duplicate onto glass slides (Amersham Pharmacia Biotech, Piscataway, N.J.) as previously described (Ye et al., 2000, J. Bacteriol. 182: 4458-4465, the entire teaching of which is incorporated herein by reference). Each slide contains 9220 features corresponding to duplicate copies of each open reading frame, additional PCR products for some ORFs, rRNA genes, and other controls. RNA preparations were used to synthesize Cy3- and Cy5-labeled cDNA and hybridization was performed as described (Ye et al., 2000, J Bacteriol. 182: 4458-4465; Ye et al., 2001, J Microbiol Methods. 47: 257-272, the entire teaching of which are incorporated herein by reference). All comparisons were performed twice (once each with Cy3 and Cy5) to control for possible differences in labeling efficiency between fluorophores. Fluorescent signal intensity data was quantified using ArrayVision software (Molecular Dynamics) and normalized to the total detectable mRNA. Mean fluorescence intensity is set to 1.0 with a value of 0.1 corresponding to background. Each expression ratio is represented by at least four separate measurements (duplicate spots on each of two slides).

For analysis and plotting of the microarray data (FIG. 8) the datasets were filtered to remove those genes that were not expressed at levels significantly above background in either condition (sum of mean fluorescence intensity <0.30; this typically reduces the size of the data files from 4610 lines to ~2800 lines). In addition, the mean and standard deviation of the fluorescence intensity were computed for each gene (based on two signals on each of two slides) and those where the standard deviation was greater than the mean intensity were removed (this removes another ~30 to ~80 genes; typically those with a strong signal for only one or two of the four spots). Finally, control spots corresponding to rRNA genes were removed. The remaining fluorescence values (FIG. 10) were used for data display.

Example 2

Media and growth conditions: B. subtilis and E. coli were routinely grown in LB medium at 37 YC with aeration. Ampicillin (100 µg/ml) was used for selection of pJPM122 and its derivatives in E. coli. Kanamycin (100 µg/ml), neomycin (10 µg/ml) chloramphenicol (1 µg/ml), and erythromycin (1 µg/ml) plus lincomycin (25 µg/ml) for MLS resistance, were used for the selection of the B. subtilis mutants used in this study.

Bacterial strains and plasmids: The strains of E. coli, B. subtilis, as well as the plasmids used are listed in Table 6. SPβ phages are derivatives of SPβc2Δ2 and were constructed by integration of a promoter region-cat-lacZ fusion constructed in pJPM122 into B. subtilis strain ZB307A as described previously (Neu, T. R., 1996, Microbiol Rev 60:151-66). SPβ lysates were prepared by heat induction from the lysogenic strains as described (Slack, F. J., et al., 1993, J Bacteriol 175:4605-14).

TABLE 6

Strains, plasmids and oligonucleotides (SEQ ID NOS: 68-81 respectively, in order of appearance) used in this study

| Name | genotype, features, sequence | reference |
| --- | --- | --- |
| E. coli | | |
| DH5α | φ80lacZΔm15 recA1 endA1 gyrA96 thi-1 hsdR17 (r$_K^-$, m$_K^+$) supE44 relA1 deoR Δ(lacZYA-argF)U169 | laboratory stock |
| B. subtilis | | |
| CU1065 | W168 attSPβ trpC2 | laboratory stock |
| ZB307A | W168 SPβc2Δ2::Tn917::pSK10Δ6 | Zuber, P. et. al. |
| BSF2469 | CU1065 liaH::pMUTIN | Zoltan Pragai |
| BSF2470 | CU1065 liaI::pMUTIN | Zoltan Pragai |
| HB0933 | CU1065 liaR::kan | Mascher, T. et. al. |
| HB0940 | W168 SPβc2Δ2::Tn917::Φ(P$_{liaI-29}$-cat-lacZ) | this work |
| HB0941 | W168 SPβc2Δ2::Tn917::Φ(P$_{liaI-58}$-cat-lacZ) | this work |
| HB0942 | W168 SPβc2Δ2::Tn917::Φ(P$_{liaI-74}$-cat-lacZ) | this work |
| HB0943 | W168 SPβc2Δ2::Tn917::Φ(P$_{liaI-83}$-cat-lacZ) | this work |
| HB0944 | W168 SPβc2Δ2::Tn917::Φ(P$_{liaI-193}$-cat-lacZ) | this work |
| HB0949 | CU1065 SPβc2Δ2::Tn917::Φ(P$_{liaI-58}$-cat-lacZ) | this work |
| HB0950 | CU1065 SPβc2Δ2::Tn917::Φ(P$_{liaI-74}$-cat-lacZ) | this work |
| HB0952 | CU1065 SPβc2Δ2::Tn917::Φ(P$_{liaI-58}$-cat-lacZ),liaR::kan | this work |
| HB0953 | CU1065 SPβ2cΔ2::Tn917::Φ(P$_{liaI-74}$-cat-lacZ),liaR::kan | this work |

TABLE 6-continued

Strains, plasmids and oligonucleotides (SEQ ID NOS: 68-81 respectively, in order of appearance) used in this study

| Name | genotype, features, sequence | reference |
|---|---|---|
| Plasmids | | |
| pJPM122 | cat-lacZ operon fusion vector for SPβ | Slack, F. J., et al. |
| pSLZ29 | pJPM122 with $P_{liaI-29}$ | this work |
| pSLZ58 | pJPM122 with $P_{liaI-58}$ | this work |
| pSLZ74 | pJPM122 with $P_{liaI-74}$ | this work |
| pSLZ83 | pJPM122 with $P_{liaI-83}$ | this work |
| pSLZ193 | pJPM122 with $P_{liaI-193}$ | this work |
| Oligo-nucleotides[1] | | |
| #1312 | yvqH fwd: GGAGGAATCAGGTATGG | |
| #1314 | yvqH rev: CTTGACCGCAAATCCTTCC | |
| #1779 | yvqG fwd: CAACTCTTATCGTCAGGCTTCCG | |
| #1311 | yvqH-do rev: CGCTAGATCCCCGCTGTCC | |
| #1503 | PyvqI-559: GGAT*CTGCAG*GGTTTGTGCTGGCGAAAGTCAAGG | |
| #1628 | yvqI-PE: TTAATAAGAATCCGCCTATTG | |
| #1310 | yvqH-do fwd: GCAGACCAGACAAAAGCGGC | |
| #1629 | yvqG-PE: TCCGCTATAATCCGGACATCC | |
| #1506 | PyvqI-193: CCAT*CTGCAG*GCCAAAGCAGAAAGGTCCGACC | |
| #1507 | PyvqI-83: CCAT*CTGCAG*CCGGTGCGAGATACGACTCC | |
| #1508 | PyvqI-74: GGAT*CTGCAG*GATACGACTCCGGTCTTATATAAAAATC | |
| #1509 | PyvqI-58: GGAT*CTGCAG*TATATAAAAATCAATCTCTGATTCG | |
| #1510 | PyvqI-29: GGAT*CTGCAG*GCATATCTTCCAACTTG | |
| #1511 | PyvqI+93: CGAT*GGATCC*TCCTCCAAAAAAGACGGAGATCCC | |

[1]numbers and names of the oligonucleotides according to the Helmann lab oligo collection DNA manipulations and sequencing: Preparation of chromosomal DNA, transformation and SPβ transduction were performed according to standard procedures. *E. coli* plasmid DNA and restriction enzyme fragments were isolated using the QIAprep spin miniprep and PCR purification kits, respectively (Qiagen Inc., Chatsworth, Calif.). Restriction endonucleases, DNA ligase, (New England Biolabs, Beverly, Mass.), Pfu DNA polymerase (Stratagene, La Jolla, Calif.), HotStar DNA polymerase (Qiagen Inc., Chatsworth, Calif.) were used according to manufacturers' instructions. DNA sequencing was performed with AmpliTaq-FS DNA polymerase and dye terminator chemistry by the DNA services facility of the Cornell New York State Center for Advanced Technology-Biotechnology.

Northern analysis of liaH and liaG: Total RNA was extracted from 5 ml of CU1065 culture with and without bacitracin (10 μg/ml final concentration). Bacitracin was added to the culture at $OD_{600}$ of 0.45 (mid-log phase) and the cultures were incubated for 15 min at 37 YC with aeration before the cells were harvested and rapidly frozen at −80° C. RNA was prepared using the RNeasy kit (Qiagen) according to the manufacturer's protocol. Internal fragments of liaH and liaG (500-750 nucleotide length) were amplified by PCR using the primer pairs: 5' #1312-3' #1314 and 5' #1779-3' #1311 (Table 6). The PCR-fragments were purified using the Qiagen PCR-Purification kit and 100 ng of each fragment were labeled with [α-$^{32}$P]dATP (New England Nuclear; 3000 Ci/mmol, 10 mCi/μl) by random oligonucleotide-primed synthesis using the Klenow-fragment of DNA-polymerase (3'♦5' exo⁻, New England Biolabs) according to published procedure ((1), 3.5.9-10). Unincorporated [α-$^{32}$P]dATP was removed by NucAway spin columns (Ambion).

Northern analysis was carried out using the NorthernMax formaldehyde-based system (Ambion) according to the manufacturer's instruction; using 10 μg total RNA and Zeta-Probe blotting membrane (Bio-Rad) in a downward transfer setup. After hybridization and washing of the membranes, the blots were wrapped in plastic wrap, exposed for 12 hours to a phosphor screen (Molecular Dynamics) and analyzed using a Phosphor Imager (Molecular Dynamics).

Primer extension mapping of the liaI promoter site: For mapping of the liaI promoter, CU1065 cells were grown in LB and total RNA was isolated from un-induced and bacitracin-induced (final concentration 10 μg/ml) mid-logarithmic cultures as described above. Primer extension reactions for liaI were set up as follows: 30 μg of heat-denatured RNA was hybridized at 65° C. to ~2 pmol of end-labeled primer #1628 in buffer containing 60 mM NaCl, 50 mM Tris-HCl (pH 7.9), 10 mM DTT, and 40 U of RNasin (Promega) in a total volume of 30 μl. Following hybridization, 50 μl extension buffer (72 mM NaCl, 50 mM Tris-HCl [pH 7.9], 10 mM DTT, 20 mM $MgCl_2$), dNTPs (10 mM), and 2 μl Superscript II reverse transcriptase (Invitrogen, Carlsbad, Calif.) was added to the mixture and incubation continued at 37° C. for 30 min. The primer extension products were precipitated with ethanol, re-suspended in sequence loading buffer, and loaded onto a 6% polyacrylamide sequencing gel. A PCR cycle sequencing kit (Epicentre, Madison, Wis.) was used to generate sequencing ladders corresponding to the liaI promoter region.

Construction of cat-lacZ reporter fusions for $P_{liaI}$ dissection: For the $P_{liaI}$-cat-lacZ fusions, promoter fragments of increasing lengths were generated by PCR using the 5' primers #1506-#1510 with the 3' primer #1511 (Table 6). The PCR was performed in a total volume of 50 μl using Pfu DNA polymerase (Stratagene, La Jolla, Calif.) according to the manufacturer's instruction. The reactions were initially denatured for 2 minutes at 94° C., followed by 30 cycles of 20 seconds at 94° C., 30 seconds at 50° C., 30 seconds at 72° C., and a final extension of 5 minutes at 72° C. The resulting PCR products were cloned into pJPM122 (Slack, F. J., et al., 1993, *J Bacteriol* 175:4605-14) as a PstI to BamHI fragment (restriction sites are underlined in the primer sequences in Table 6) resulting in promoter-cat-/acZ fusions in plasmids pSLZ29 (as a negative control, lacking the −35 region of $P_{liaI}$), pSLZ58 (core promoter), pSLZ74 (single TCCGGT sequence included), pSLZ83 (complete TCCGGT repeat) and pSLZ193 (positive control) (FIGS. 5b and 5c). The inserts were verified by DNA-sequencing at the Cornell BioResource Center. The plasmids were linearized and used to transform ZB307A with neomycin selection to generate strains HB0940-0944. Phages generated from strains HB0941-0942 (SPb0941-0942) were used to transduce the $P_{liaI}$-cat-lacZ fusions into CU1065 and HB0933, resulting in strains HB0949/0950 and HB0952/0953, respectively (Table 6).

$P_{liaI}$ induction assays: Screening for liaI induction was done by disk diffusion assay essentially as described (Cai, S. J., and M. Inouye, 2002, *J Biol Chem* 277:24155-61). *B. subtilis* strains were inoculated from a fresh overnight LB agar plate and grown to mid-log phase ($OD_{600}$ ~0.45) at 37 YC with shaking. 20 μl of the culture was mixed with 3 ml of 0.7% soft LB agar (containing 40 μg of X-Gal per plate) and poured onto the bottom agar. After cooling and drying of the plates (20 min at 37 YC), filter paper disks (6 mm diameter) carrying 5 μl of stock solution (antibiotics normally 100 mg/ml; lysozyme 10 mg/ml; tunicamycin, surfactants, uncouplers 5 mg/ml each; inhibitors of protein biosynthesis as given in the media and growth conditions section) were placed on top of the agar. The plates were incubated at 37 YC overnight. After 12-24 h incubation, the plates were scored for the appearance of a blue ring at or near the edge of the zone of growth inhibition produced by the diffusion of the antibiotics from the filter disk.

For quantitative measurements of β-galactosidase activity, cells were inoculated from fresh overnight LB-plates and grown in LB medium at 37 YC with aeration until they reached an $OD_{600}$ of 0.45. 2 ml of the culture was harvested (un-induced control) and the cell pellets were frozen and kept at −80 YC. The cultures were induced by addition of the compound to be tested to the final concentration as described in the individual figure legends and incubated for an additional 30 min at 37 YC. 2 ml of the cultures were harvested as described above. The pellets were re-suspended in 1 ml of working buffer (60 mM $Na_2HPO_4$, 40 mMNa$H_2PO_4$, 10 mM KCl, 1 mM $MgSO_4$, 4 mM DTT) and assayed for β-galactosidase activity as described with normalization to cell density Kobayashi, K., et al., 2001, J Bacteriol 183: 7365-7370). For concentration-dependent induction/killing experiments, cultures of strain BFS2470 were grown in LB medium to mid-logarithmic growth phase ($OD_{600}$ of 0.4 to 0.45) and the antibiotics were added to a final concentration ranging from 0.01 to 100 μg/ml. An un-induced culture was used as a negative control. The cultures were incubated with aeration at 37° C. A sample was taken after 30 min for β-galactosidase assay and the turbidity of the remaining culture was measured for at least 5 hours to monitor the concentration-dependent effects of the antibiotics on cell growth.

All patents and publications mentioned in the specification are indicative of the level of those skilled in the art to which the invention pertains. All patents and publications are herein incorporated by reference to the same extent as if each individual publication was specifically and individually indicated to be incorporated by reference.

The present invention is illustrated by the previous examples. However, it should be understood that the invention is not limited to the specific details of these examples. It will now be apparent to those skilled in the art that other embodiments, improvements, details, and uses can be made that are consistent with the letter and spirit of the foregoing disclosure and within the scope of this patent and the appended claims.

What is claimed is:

1. A system for determining whether a putative antibiotic will trigger events leading to antibiotic resistance, comprising:
    a lipid bilayer;
    the receptor protein, lipid II interacting antibiotics sensor (LiaS), wherein said receptor protein is integral within said lipid bilayer, has kinase activity and has an affinity for one or more putative antibiotic compounds;
    the substrate for said receptor protein, lipid II interacting antibiotics response regulator (LiaR); and
    at least one reporter, wherein said reporter is induced by said substrate when said substrate is phosphorylated.

2. The system of claim 1, wherein said substrate is phosphorylated in response to said putative antibiotic interacting with said receptor.

3. The system of claim 1, wherein said at least one reporter is a fusion protein.

4. The system of claim 3, wherein the phosphorylated substrate acts on a promoter region in order to induce expression of said reporter.

5. The system of claim 3, wherein said promoter region is lipid II interacting antibiotics promoter (LialH).

6. The system of claim 3, wherein said fusion protein comprises β-galactosidase or cat-lacZ.

7. The system of claim 1, wherein said antibiotic being detected interacts with undecaprenyl pyrophosphate.

* * * * *

UNITED STATES PATENT AND TRADEMARK OFFICE
CERTIFICATE OF CORRECTION

PATENT NO. : 7,309,484 B2
APPLICATION NO. : 10/875100
DATED : December 18, 2007
INVENTOR(S) : John D. Helmann et al.

It is certified that error appears in the above-identified patent and that said Letters Patent is hereby corrected as shown below:

On the Title page, under (56) References Cited, please add the following:

-- U.S. PATENT DOCUMENTS
  6,635,475    10/2003  Helmann ........................435/320.1 --

On the Title page, under (56) References Cited, and further under OTHER PUBLICATIONS, please add the following:

-- Mascher, T. et al. "Cell wall stress response in Bacillus subtilis: the regulatory network of the bacitracin stimulon."Mol. Microb. (2003) 50(5), 1591-1604.

Ohki, R. et al. "The BceRS two-component regulatory system induces expression of the bacitracin transporter, BceAB, in Bacillus subtilis." Mol. Microb. (2003) 49(4), 1135-1144.

Fischer, H.P. et al. "Identification of Antibiotic Stress-Inducible Promoters: A Systematic Approach to Novel Pathway-Specific Reporter Assays for Antibacterial Drug Discovery." Genome Research 14:90-98, 2004.

Kuroda, M. et al. "Two-component system VraSR positively modulates the regulation of cell-wall biosynthesis pathway in Staphylococcus aureus." Mol. Microb. (2003) 49 (3), 807-821. --

Signed and Sealed this

Twentieth Day of May, 2008

JON W. DUDAS
*Director of the United States Patent and Trademark Office*

SEQUENCE LISTING

<160> NUMBER OF SEQ ID NOS: 126

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ccaagcttca gaatcccccc agaaaaagaa ttcgaagaaa acaagagat          49

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tatcatacca agcgctcagc gcttgctgct gtggcatcat gcg              43

<210> SEQ ID NO 3

```
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggaagtgc tgaagggcat cgcgttgcgt ttttgattga gctggctcag c         51

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaggaatca ggtatggctt gaccgcaaat ccttcc                          36

<210> SEQ ID NO 5
<211> LENGTH: 200
<212> TYPE: DNA
<213> ORGANISM: Bacillus subtilis

<400> SEQUENCE: 5
aattaaagaa agggaagcaa gtgttcatct gtaaagggtt ttaaaacgcc atgcctcgtg    60
catggcgttt ttttgtgcca atgggtccgg tgcgagatac gactccggtc ttatataaaa   120
atcaatctct gattcgtttt gcatatcttc caacttgtat aagatgaaga caaggaaaac   180
gaaaggagga tctgcatgaa                                              200

<210> SEQ ID NO 6
<211> LENGTH: 17
<212> TYPE: DNA
<213> ORGANISM: Bacillus subtilis

<400> SEQUENCE: 6
gtataagatg aagacaa                                                17

<210> SEQ ID NO 7
<211> LENGTH: 36
<212> TYPE: RNA
<213> ORGANISM: Bacillus subtilis

<400> SEQUENCE: 7
aacggggaag gauuugcggu caaguccuuc ccuucc                          36

<210> SEQ ID NO 8
<211> LENGTH: 22
<212> TYPE: DNA
<213> ORGANISM: Bacillus subtilis

<400> SEQUENCE: 8
cctttggtgc cgcagtcagt gc                                         22

<210> SEQ ID NO 9
<211> LENGTH: 43
<212> TYPE: DNA
<213> ORGANISM: Bacillus subtilis

<400> SEQUENCE: 9
cctatcacct caaatggttc gctggtcctt catgaactga cgc                  43
```

<210> SEQ ID NO 10
<211> LENGTH: 45
<212> TYPE: DNA
<213> ORGANISM: Bacillus subtilis

<400> SEQUENCE: 10
cgagcgccta cgaggaattt gtatcgcaga ccagacaaaa gcggc                45

<210> SEQ ID NO 11
<211> LENGTH: 19
<212> TYPE: DNA
<213> ORGANISM: Bacillus subtilis

<400> SEQUENCE: 11
cgctagatcc ccgctgtcc                                             19

<210> SEQ ID NO 12
<211> LENGTH: 23
<212> TYPE: DNA
<213> ORGANISM: Bacillus subtilis

<400> SEQUENCE: 12
gacaggcaag ggaactccga tcc                                        23

<210> SEQ ID NO 13
<211> LENGTH: 45
<212> TYPE: DNA
<213> ORGANISM: Bacillus subtilis

<400> SEQUENCE: 13
cctatcacct caaatggttc gctggattcc ggaaagtatg acgcc                45

<210> SEQ ID NO 14
<211> LENGTH: 45
<212> TYPE: DNA
<213> ORGANISM: Bacillus subtilis

<400> SEQUENCE: 14
cgagcgccta cgaggaattt gtatcgccat tcaagtcaac tctcc                45

<210> SEQ ID NO 15
<211> LENGTH: 23
<212> TYPE: DNA
<213> ORGANISM: Bacillus subtilis

<400> SEQUENCE: 15
gtacgagacc tccttccatg tcg                                        23

<210> SEQ ID NO 16
<211> LENGTH: 21
<212> TYPE: DNA
<213> ORGANISM: Bacillus subtilis

<400> SEQUENCE: 16
cgaaagtgga atgtgaccag g                                          21

<210> SEQ ID NO 17
<211> LENGTH: 45
<212> TYPE: DNA
<213> ORGANISM: Bacillus subtilis

<400> SEQUENCE: 17
ccacgcttac tacgttgata agcataacat cagaattccc agtgc           45

<210> SEQ ID NO 18
<211> LENGTH: 45
<212> TYPE: DNA
<213> ORGANISM: Bacillus subtilis

<400> SEQUENCE: 18
gggatcaact ttgggagaga gttcaatggg tcacagaaga tgagc           45

<210> SEQ ID NO 19
<211> LENGTH: 22
<212> TYPE: DNA
<213> ORGANISM: Bacillus subtilis

<400> SEQUENCE: 19
gcaacactga tggtatctag gg                                    22

<210> SEQ ID NO 20
<211> LENGTH: 20
<212> TYPE: DNA
<213> ORGANISM: Bacillus subtilis

<400> SEQUENCE: 20
ccaaggctga catgatccgc                                       20

<210> SEQ ID NO 21
<211> LENGTH: 45
<212> TYPE: DNA
<213> ORGANISM: Bacillus subtilis

<400> SEQUENCE: 21
cttgataata agggtaacta ttgccctcct tccttgggat agccc           45

<210> SEQ ID NO 22
<211> LENGTH: 45
<212> TYPE: DNA
<213> ORGANISM: Bacillus subtilis

<400> SEQUENCE: 22
gggtaactag cctcgccggt ccacgactca tggactatga gagcc           45

<210> SEQ ID NO 23
<211> LENGTH: 22
<212> TYPE: DNA
<213> ORGANISM: Bacillus subtilis

<400> SEQUENCE: 23
gctgtgattg ccacagtgtt cg                                    22

<210> SEQ ID NO 24
<211> LENGTH: 22
<212> TYPE: DNA
<213> ORGANISM: Bacillus subtilis

<400> SEQUENCE: 24
gtctcttcta tgcttagacg gc                                    22

<210> SEQ ID NO 25
<211> LENGTH: 43
<212> TYPE: DNA
<213> ORGANISM: Bacillus subtilis

<400> SEQUENCE: 25

```
cctatcacct caaatggttc gctgctgaga gtccagaaag agc            43

<210> SEQ ID NO 26
<211> LENGTH: 45
<212> TYPE: DNA
<213> ORGANISM: Bacillus subtilis

<400> SEQUENCE: 26
cgagcgccta cgaggaattt gtatcggatc atggataact atcgg          45

<210> SEQ ID NO 27
<211> LENGTH: 22
<212> TYPE: DNA
<213> ORGANISM: Bacillus subtilis

<400> SEQUENCE: 27
cacatgctac ttgatagcag gg                                   22

<210> SEQ ID NO 28
<211> LENGTH: 24
<212> TYPE: DNA
<213> ORGANISM: Bacillus subtilis

<400> SEQUENCE: 28
acgtaacgtg ccaatgctga ttgc                                 24

<210> SEQ ID NO 29
<211> LENGTH: 45
<212> TYPE: DNA
<213> ORGANISM: Bacillus subtilis

<400> SEQUENCE: 29
ttgataataa gggtaactat tgccggccgt caatcgcttt tgaca          45

<210> SEQ ID NO 30
<211> LENGTH: 45
<212> TYPE: DNA
<213> ORGANISM: Bacillus subtilis

<400> SEQUENCE: 30
gggtaactag cctcgccggt ccacaagcta ccaaaaccaa cgtgc          45

<210> SEQ ID NO 31
<211> LENGTH: 24
<212> TYPE: DNA
<213> ORGANISM: Bacillus subtilis

<400> SEQUENCE: 31
gcttggattt tcgcgatcag caca                                 24

<210> SEQ ID NO 32
<211> LENGTH: 20
<212> TYPE: DNA
<213> ORGANISM: Bacillus subtilis

<400> SEQUENCE: 32
gggaagagtc gcaaagtcgg                                      20

<210> SEQ ID NO 33
<211> LENGTH: 44
<212> TYPE: DNA
<213> ORGANISM: Bacillus subtilis
```

<400> SEQUENCE: 33
gggtaactag cctcgccggt ccacggcaaa acgccagcat gcgc         44

<210> SEQ ID NO 34
<211> LENGTH: 45
<212> TYPE: DNA
<213> ORGANISM: Bacillus subtilis

<400> SEQUENCE: 34
cttgataata agggtaacta ttgccgaccg tcaatgtcaa tcgcc        45

<210> SEQ ID NO 35
<211> LENGTH: 22
<212> TYPE: DNA
<213> ORGANISM: Bacillus subtilis

<400> SEQUENCE: 35
gacgcttgat catggtgatc cg                                 22

<210> SEQ ID NO 36
<211> LENGTH: 24
<212> TYPE: DNA
<213> ORGANISM: Bacillus subtilis

<400> SEQUENCE: 36
gagaacaatc tcgatgtgac agcc                               24

<210> SEQ ID NO 37
<211> LENGTH: 44
<212> TYPE: DNA
<213> ORGANISM: Bacillus subtilis

<400> SEQUENCE: 37
cctatcacct caaatggttc gctgcgatgc ccttcagcac ttcc         44

<210> SEQ ID NO 38
<211> LENGTH: 45
<212> TYPE: DNA
<213> ORGANISM: Bacillus subtilis

<400> SEQUENCE: 38
cgagcgccta cgaggaattt gtatcgatat actgcgctct actcc        45

<210> SEQ ID NO 39
<211> LENGTH: 26
<212> TYPE: DNA
<213> ORGANISM: Bacillus subtilis

<400> SEQUENCE: 39
ctccgtacga atccagttat catagc                             26

<210> SEQ ID NO 40
<211> LENGTH: 21
<212> TYPE: DNA
<213> ORGANISM: Bacillus subtilis

<400> SEQUENCE: 40
gaacgaattc cctcattccg c                                  21

<210> SEQ ID NO 41
<211> LENGTH: 45
<212> TYPE: DNA
<213> ORGANISM: Bacillus subtilis

```
<400> SEQUENCE: 41
cctatcacct caaatggttc gctggcacct cctggttgat cgtac            45

<210> SEQ ID NO 42
<211> LENGTH: 45
<212> TYPE: DNA
<213> ORGANISM: Bacillus subtilis

<400> SEQUENCE: 42
gagcgcctac gaggaatttg tatcggtcat tgatacaatc gcctc            45

<210> SEQ ID NO 43
<211> LENGTH: 20
<212> TYPE: DNA
<213> ORGANISM: Bacillus subtilis

<400> SEQUENCE: 43
gatatccaag gaactggcgc                                        20

<210> SEQ ID NO 44
<211> LENGTH: 23
<212> TYPE: DNA
<213> ORGANISM: Bacillus subtilis

<400> SEQUENCE: 44
atggctgtct gcggaaaacg gcg                                    23

<210> SEQ ID NO 45
<211> LENGTH: 44
<212> TYPE: DNA
<213> ORGANISM: Bacillus subtilis

<400> SEQUENCE: 45
gggatcaact ttgggagaga gttccaagca gcacaagatc aggc             44

<210> SEQ ID NO 46
<211> LENGTH: 43
<212> TYPE: DNA
<213> ORGANISM: Bacillus subtilis

<400> SEQUENCE: 46
ccacgcttac tacgttgata agccaatcgg aaggatgaag cgg              43

<210> SEQ ID NO 47
<211> LENGTH: 21
<212> TYPE: DNA
<213> ORGANISM: Bacillus subtilis

<400> SEQUENCE: 47
gcctctttca tggttcgtcc g                                      21

<210> SEQ ID NO 48
<211> LENGTH: 25
<212> TYPE: DNA
<213> ORGANISM: Bacillus subtilis

<400> SEQUENCE: 48
gcttgcagaa caagcctctt cttcg                                  25

<210> SEQ ID NO 49
<211> LENGTH: 45
<212> TYPE: DNA
```

```
<213> ORGANISM: Bacillus subtilis

<400> SEQUENCE: 49
cttgataata agggtaacta ttgccggcgc tgagcgcttg gtatg         45

<210> SEQ ID NO 50
<211> LENGTH: 43
<212> TYPE: DNA
<213> ORGANISM: Bacillus subtilis

<400> SEQUENCE: 50
gggtaactag cctcgccggt ccacggcgtg ctgttcttca gcg           43

<210> SEQ ID NO 51
<211> LENGTH: 23
<212> TYPE: DNA
<213> ORGANISM: Bacillus subtilis

<400> SEQUENCE: 51
ccgattcctg aagagattga agc                                 23

<210> SEQ ID NO 52
<211> LENGTH: 21
<212> TYPE: DNA
<213> ORGANISM: Bacillus subtilis

<400> SEQUENCE: 52
gctgtcatca agctggttcg g                                   21

<210> SEQ ID NO 53
<211> LENGTH: 45
<212> TYPE: DNA
<213> ORGANISM: Bacillus subtilis

<400> SEQUENCE: 53
cctatcacct caaatggttc gctgcgatgc ttcgccgatg acttc         45

<210> SEQ ID NO 54
<211> LENGTH: 45
<212> TYPE: DNA
<213> ORGANISM: Bacillus subtilis

<400> SEQUENCE: 54
cgagcgccta cgaggaattt gtatcggcac accgaaatca tctcg         45

<210> SEQ ID NO 55
<211> LENGTH: 23
<212> TYPE: DNA
<213> ORGANISM: Bacillus subtilis

<400> SEQUENCE: 55
ctcttcatct gatccgacac agc                                 23

<210> SEQ ID NO 56
<211> LENGTH: 20
<212> TYPE: DNA
<213> ORGANISM: Bacillus subtilis

<400> SEQUENCE: 56
ttaggaggaa tcaggtatgg                                     20

<210> SEQ ID NO 57
<211> LENGTH: 44
```

```
<212> TYPE: DNA
<213> ORGANISM: Bacillus subtilis

<400> SEQUENCE: 57
cctatcacct caaatggttc gctgccggac atccttgcta tccg                    44

<210> SEQ ID NO 58
<211> LENGTH: 45
<212> TYPE: DNA
<213> ORGANISM: Bacillus subtilis

<400> SEQUENCE: 58
cgagcgccta cgaggaattt gtatcggcac accgaaatca tctcg                   45

<210> SEQ ID NO 59
<211> LENGTH: 23
<212> TYPE: DNA
<213> ORGANISM: Bacillus subtilis

<400> SEQUENCE: 59
ctcttcatct gatccgacac agc                                           23

<210> SEQ ID NO 60
<211> LENGTH: 22
<212> TYPE: DNA
<213> ORGANISM: Bacillus subtilis

<400> SEQUENCE: 60
gaatctcaat cagagtctgc gg                                            22

<210> SEQ ID NO 61
<211> LENGTH: 45
<212> TYPE: DNA
<213> ORGANISM: Bacillus subtilis

<400> SEQUENCE: 61
gggatcaact ttgggagaga gttctgcgta tgtcatcaag ctccc                   45

<210> SEQ ID NO 62
<211> LENGTH: 44
<212> TYPE: DNA
<213> ORGANISM: Bacillus subtilis

<400> SEQUENCE: 62
ccacgcttac tacgttgata agcatcagac cagacaaaag cggc                    44

<210> SEQ ID NO 63
<211> LENGTH: 19
<212> TYPE: DNA
<213> ORGANISM: Bacillus subtilis

<400> SEQUENCE: 63
cgctagatcc ccgctgtcc                                                19

<210> SEQ ID NO 64
<211> LENGTH: 24
<212> TYPE: DNA
<213> ORGANISM: Bacillus subtilis

<400> SEQUENCE: 64
cattccctat gtggcatcca ctgc                                          24

<210> SEQ ID NO 65
```

```
<211> LENGTH: 44
<212> TYPE: DNA
<213> ORGANISM: Bacillus subtilis

<400> SEQUENCE: 65
ccacgcttac tacgttgata agcatcatcg gcaagcgcta cgcg                    44

<210> SEQ ID NO 66
<211> LENGTH: 45
<212> TYPE: DNA
<213> ORGANISM: Bacillus subtilis

<400> SEQUENCE: 66
gggatcaact ttgggagaga gttcaagacc ggacacaggc agtcg                   45

<210> SEQ ID NO 67
<211> LENGTH: 23
<212> TYPE: DNA
<213> ORGANISM: Bacillus subtilis

<400> SEQUENCE: 67
agtctctgat aatgtagtgg agc                                           23

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaggaatca ggtatgg                                                  17

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cttgaccgca aatccttcc                                                19

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
caactcttat cgtcaggctt ccg                                           23

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cgctagatcc ccgctgtcc                                                19
```

```
<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggatctgcag ggtttgtgct ggcgaaagtc aagg                              34

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttaataagaa tccgcctatt g                                            21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcagaccaga caaaagcggc                                              20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tccgctataa tccggacatc c                                            21

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ccatctgcag gccaaagcag aaaggtccga cc                                32

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ccatctgcag ccggtgcgag atacgactcc                                   30
```

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 78
ggatctgcag gatacgactc cggtcttata taaaaatc                            38

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 79
ggatctgcag tatataaaaa tcaatctctg attcg                              35

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 80
ggatctgcag gcatatcttc caacttg                                       27

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 81
cgatggatcc tcctccaaaa aagacggaga tccc                               34

<210> SEQ ID NO 82
<211> LENGTH: 351
<212> TYPE: PRT
<213> ORGANISM: Bacillus anthracis

<400> SEQUENCE: 82

Met Ser Lys Phe Lys Met Leu Lys Val Thr Gly Ala Ile Ile Ala Leu
 1               5                  10                  15

Phe Ser Phe Leu Thr Ile Ile Trp Ser Thr Ala Phe Tyr Val Ser Ser
                20                  25                  30

Ser Ile Leu Asp Ala Leu Ala Ile His Leu Ser Pro Phe Val Thr Tyr
            35                  40                  45

Leu Ile Ser Asp Ile Leu Ser Phe Ile Phe Met Ile Leu Val Trp Ile
        50                  55                  60

Leu Ile Ala Val Leu Met Arg Pro Lys Arg Glu Ala Met Ile Trp Thr
    65                  70                  75                  80

Ile Ile Glu Pro Ile Gln Lys Ile Ala Lys Gly Asp Phe Ser Val Lys
                85                  90                  95

Ile Arg Asn Glu Glu Lys Tyr Asp Gly Glu Ile Gly Val Leu Val Lys

-continued

```
            100                 105                 110

Ser Ile Asn Asp Met Thr Asp Glu Leu Asn Ala Met Glu Lys Met Arg
        115                 120                 125

Gln Glu Phe Val Ser Asn Val Ser His Glu Ile Gln Ser Pro Leu Thr
    130                 135                 140

Ser Ile Lys Gly Phe Ala Arg Ala Leu Gln Asp Thr Asn Leu Pro Glu
145                 150                 155                 160

Glu Lys Arg Lys His Tyr Leu Thr Ile Ile Glu Thr Glu Thr Thr Arg
                165                 170                 175

Leu Ser Lys Leu Ser Gln Asn Leu Leu Lys Leu Thr Leu Leu Glu Ser
            180                 185                 190

Glu Glu Tyr Thr Pro Glu Arg Val Thr Tyr Arg Leu Asp Gln Gln Leu
        195                 200                 205

Lys Gln Ile Val Leu Asn Ser Glu Pro Leu Trp Ala Glu Lys Glu Ile
    210                 215                 220

Glu Leu Asp Leu Asp Leu Glu Lys Val His Ile Thr Ala Asp Gln Glu
225                 230                 235                 240

Ser Met Ser Gln Val Trp Ile Asn Leu Ile His Asn Ser Ile Lys Phe
                245                 250                 255

Thr Pro Ser Ser Gly Thr Ile Ser Ile Lys Leu Lys Glu Tyr Glu Thr
            260                 265                 270

Leu Val Glu Val Arg Ile Arg Asp Thr Gly Ser Gly Ile Ser Glu Glu
        275                 280                 285

Gln Lys Gln His Ile Phe Glu Arg Phe Tyr Lys Ala Asp Ser Ser Arg
    290                 295                 300

Asn Arg Ala Tyr Gly Gly Ser Gly Leu Gly Leu Ala Ile Val Lys Lys
305                 310                 315                 320

Val Leu Asp Leu His Gln Gly Glu Ile Lys Val Glu Ser Glu Glu Gly
                325                 330                 335

Asn Gly Thr Glu Cys Ile Val Cys Ile Pro Asn Tyr Glu Glu Lys
            340                 345                 350

<210> SEQ ID NO 83
<211> LENGTH: 358
<212> TYPE: PRT
<213> ORGANISM: Bacillus cereus

<400> SEQUENCE: 83

Met Lys Ile Lys Ser Leu Gln Gly Ile Arg Ala Lys Phe Phe Ile Ala
  1               5                  10                  15

Phe Ile Cys Ser Ile Phe Leu Ala Ile Val Ser Ile Ile Val Phe Gln
            20                  25                  30

Ile Leu Ile Gly Asn Ile Tyr Ser His Val Thr Ala Leu Glu Glu Lys
        35                  40                  45

Tyr Ser Phe Leu Tyr Phe Ile Val Phe Leu Ile Phe Thr Thr Thr Tyr
     50                  55                  60

Phe Ala Phe Met Thr Lys Thr Leu Met Lys Arg Leu Ser Gln Ile Asn
 65                  70                  75                  80

Lys Asn Val Lys Glu Ile Ser Glu Gly Asn Phe Glu Ile His Ile Pro
                 85                  90                  95

Ile Ser Lys Ser Asp Glu Ile Gly Glu Leu Ala Ala Asn Val Asn Arg
            100                 105                 110

Met Ala Lys Ser Leu Lys Glu Ser Ile Glu Asn Glu Lys Lys Ser Gln
        115                 120                 125
```

-continued

```
Glu Met Lys Asn Glu Met Ile Ser Asn Ile Ser His Asp Leu Arg Thr
    130                 135                 140

Pro Val Thr Ser Leu Ile Gly Tyr Ala Asp Leu Leu Gly Asn Lys Leu
145                 150                 155                 160

His Ser Asn Gly Glu Glu Cys Glu Gln Tyr Val Ser Ile Leu Lys Arg
                165                 170                 175

Lys Ser Tyr Glu Leu Lys Asn Gln Val Asp Asp Leu Leu Glu Tyr Cys
            180                 185                 190

Gln Ile Asn Tyr Arg Glu Ile Glu Leu His Lys Asp Glu Val Asp Met
        195                 200                 205

Lys Ala Leu Ile Glu Gln Ile Met Ile Asp Phe Val Pro Gln Leu Asp
    210                 215                 220

Asp Ala Asn Met Ser Phe Tyr Ile Lys Ser Asp Glu Val Leu His Val
225                 230                 235                 240

Glu Val Asp Val Ala Leu Ile Val Arg Leu Phe Glu Asn Val Ile Gly
                245                 250                 255

Asn Ser Ile Met Tyr Gly Lys Asp Gly Lys Glu Ile Ala Ile Glu Ile
            260                 265                 270

Ser Asn Lys Thr Met Asn Val Glu Val Glu Ile Lys Asn Phe Gly Gln
        275                 280                 285

Cys Ile Pro Lys Glu Asp Leu Pro Tyr Val Phe Glu Lys Phe Tyr Arg
    290                 295                 300

Ser Glu Lys Ser Arg Ser Ser His Thr Gly Gly Lys Gly Met Gly Leu
305                 310                 315                 320

Ala Ile Ser Lys Ser Ile Ala Gln Leu His Gln Gly Asp Ile Thr Val
                325                 330                 335

Arg Ser Asn Asp Lys Glu Thr Val Phe Thr Val Lys Leu Pro Gln Tyr
            340                 345                 350

Lys Lys Val Arg Lys Ser
        355

<210> SEQ ID NO 84
<211> LENGTH: 348
<212> TYPE: PRT
<213> ORGANISM: Bacillus cereus
<400> SEQUENCE: 84

Met Lys Met Leu Lys Val Phe Gly Ala Val Leu Ala Leu Phe Ser Ile
  1               5                  10                  15

Leu Thr Ile Ile Trp Ser Ile Ala Phe Tyr Val Ala Thr Ser Leu Leu
             20                  25                  30

Asn Ala Phe Asp Val Asn Val Ser Pro Phe Val Ala Phe Leu Ile Ser
         35                  40                  45

Asp Met Val Gly Phe Val Phe Ile Ile Leu Ile Trp Thr Leu Ile Gly
     50                  55                  60

Ile Leu Met Arg Pro Lys Arg Glu Ala Met Ile Trp Thr Ile Ile Glu
 65                  70                  75                  80

Pro Ile Gln Lys Ile Ala Lys Gly Asp Phe Ser Val Lys Ile Arg Asn
                 85                  90                  95

Glu Glu Lys Tyr Asp Gly Glu Ile Gly Val Leu Val Lys Ser Ile Asn
            100                 105                 110

Asp Met Thr Asp Glu Leu Asn Thr Met Glu Lys Met Arg Gln Glu Phe
        115                 120                 125

Val Ser Asn Val Ser His Glu Ile Gln Ser Pro Leu Thr Ser Ile Lys
    130                 135                 140
```

```
Gly Phe Ala Arg Ala Leu Gln Asp Asp Asn Leu Ser Glu Glu Lys Arg
145                 150                 155                 160

Lys His Tyr Leu Thr Ile Ile Glu Thr Glu Thr Arg Leu Ser Lys
            165                 170                 175

Leu Ser Gln Asn Leu Leu Lys Leu Thr Leu Leu Glu Ser Glu Glu Tyr
                180                 185                 190

Thr Pro Glu Arg Val Ser Tyr Arg Leu Asp Gln Gln Leu Lys Gln Ile
            195                 200                 205

Val Leu Asn Ser Glu Pro Leu Trp Ala Glu Lys Glu Ile Glu Leu Glu
    210                 215                 220

Leu Asp Leu Glu Lys Val Tyr Val Ile Ala Asp Gln Glu Ser Met Ser
225                 230                 235                 240

Gln Val Trp Ile Asn Leu Ile His Asn Ser Ile Lys Phe Thr Pro Ser
                245                 250                 255

Gly Gly Thr Ile Thr Ile Gln Leu Lys Glu His Glu Thr Val Val Glu
            260                 265                 270

Val Arg Ile Arg Asp Ser Gly Ile Gly Ile Ser Glu Glu Gln Lys Gln
    275                 280                 285

His Ile Phe Glu Arg Phe Tyr Lys Ala Asp Ser Ser Arg Asn Arg Ala
    290                 295                 300

Tyr Gly Ser Gly Leu Gly Leu Ala Ile Val Lys Lys Val Leu Asp
305                 310                 315                 320

Leu His His Gly Glu Ile Lys Val Glu Ser Glu Gly Lys Gly Thr
                325                 330                 335

Glu Phe Ile Val Arg Met Pro Asn His Glu Glu Lys
                340                 345

<210> SEQ ID NO 85
<211> LENGTH: 334
<212> TYPE: PRT
<213> ORGANISM: Bacillus halodurans

<400> SEQUENCE: 85

Met Ile Lys Thr Phe Ile Lys Glu Arg Gly Ser Trp Ile Leu Ile Ile
1               5                   10                  15

Ile Phe Leu Gln Cys Phe Thr Val Phe Ile Ala Tyr Leu Asp Ser Ala
                20                  25                  30

Ile Pro Leu Ala Pro Val Phe Tyr Ser Val Phe Leu Ser Ser Met Ile
            35                  40                  45

Phe Leu Phe Phe Leu Ala Val Arg Tyr Lys Lys Glu Thr Thr Phe Tyr
    50                  55                  60

Arg Lys Leu Glu Glu Trp Asp Lys Asp Leu Asp Val Thr Asn Leu Ala
65                  70                  75                  80

Ala Ala Glu Ser Pro Phe Glu Arg Ile Ile Glu Gln Thr Ile Val Lys
                85                  90                  95

Gln Thr Gly Tyr Leu Gln Glu Lys Ala His Arg His Glu Thr Ala Leu
            100                 105                 110

Glu Gln Glu Lys Asp Asp Leu Leu Ala Trp Ile His Glu Ile Lys Thr
        115                 120                 125

Pro Leu Thr Ala Met His Leu Ile Ile Asp Arg Leu Glu Asp Arg Thr
    130                 135                 140

Ile Lys Gly Gln Leu Thr Tyr Glu Trp Met Arg Ile His Leu Leu Leu
145                 150                 155                 160

Asp Gln Gln Leu His Gln Lys Arg Ile Pro Phe Met Glu Asn Asp Leu
```

```
                165                 170                 175
Tyr Val Glu Lys Val Asn Leu Glu Ser Val Leu His Gln Glu Ile Lys
            180                 185                 190

Thr Leu Gln Ser Trp Cys Ile Gln Lys Gly Ile Gly Phe Asp Leu Gln
        195                 200                 205

Leu Glu Val Thr Asp Val Leu Thr Asp Ala Lys Trp Leu Ser Phe Ile
    210                 215                 220

Leu Arg Gln Leu Leu Ser Asn Ala Val Lys Tyr Ser Glu Ala Ser Asp
225                 230                 235                 240

Ile Ile Ile Lys Ser Asp Val Val Ser Gly Lys Thr Val Val Glu Val
                245                 250                 255

Thr Asp Phe Gly Arg Gly Ile Glu Pro Lys Asp Leu Pro Arg Ile Phe
            260                 265                 270

Glu Lys Gly Phe Thr Ser Thr Lys Thr Asp Gln Thr Asn Gly Ala Thr
        275                 280                 285

Gly Met Gly Leu Tyr Leu Ala Lys Arg Val Ala Glu Pro Leu Leu Ile
    290                 295                 300

Asp Leu Ala Val Ser Ser Thr Val Gly Glu Gly Thr Thr Phe Thr Leu
305                 310                 315                 320

Thr Phe Pro Lys Glu Asn Glu Phe Val Arg Thr Leu Gly Met
                325                 330
```

<210> SEQ ID NO 86
<211> LENGTH: 343
<212> TYPE: PRT
<213> ORGANISM: Bacillus halodurans

<400> SEQUENCE: 86

```
Met Phe Arg Thr Val Phe Ile Ala Phe Ile Lys Asp Arg Ser Leu Phe
1               5                   10                  15

Ser Leu Phe Tyr Phe Leu Gly Val Gly Ser Val Leu Leu Phe Phe Tyr
            20                  25                  30

Ile Ser His Pro Ala Gln Ser Glu Ile Met Tyr Pro Thr Leu Ile Ala
        35                  40                  45

Cys Phe Leu Tyr Ile Leu Tyr Leu Leu Ile Glu Trp Ser Lys Tyr Gly
    50                  55                  60

His Phe His Arg Gln Leu Lys Lys Arg His Ala Gly Glu Ser Arg Glu
65                  70                  75                  80

Leu Ala Pro Lys Thr Glu Glu Gln Arg Val Met Thr Glu Leu Ile Glu
            85                  90                  95

Thr Val Thr Ser Asp Phe Arg Arg Asp Met Ser Gln Leu His Ile Gln
        100                 105                 110

Asn Lys Glu Arg Leu Tyr Leu Val Ser His Trp Ile His Gln Leu Lys
    115                 120                 125

Thr Pro Val Ser Val Asn Glu Leu Leu Met Asp Gln Leu Leu Lys Glu
130                 135                 140

Glu Thr Asn Ser Gln Ser Val Asp Leu Leu Lys Arg Met Lys Arg Glu
145                 150                 155                 160

Asn Arg Gly Leu His Ser Arg Ile Glu Gln Gly Leu Thr Met Ile Arg
                165                 170                 175

Met Glu Gly Phe Glu His Asp Phe Glu Pro Arg Pro Val His Leu Leu
            180                 185                 190

Ser Ser Leu Arg Lys Val Val Asn Ala Arg Lys Ser Glu Phe Ile Tyr
        195                 200                 205
```

-continued

His His Ile Leu Pro Val Ile Glu Gly Met Glu Gly Val Arg Ile Ile
210                 215                 220

Thr Asp Glu Lys Trp Asn Glu Val Leu Leu Glu Gln Ile Ile Ser Asn
225                 230                 235                 240

Ala Val Lys Tyr Ser Arg Gly Gln Gly Glu Met Lys Lys Ile Tyr Leu
            245                 250                 255

Ser Gly Gln Ala Asp Gly Glu Ala Trp Ile Leu Thr Ile Arg Asp Glu
            260                 265                 270

Gly Val Gly Ile Pro Pro Tyr Asp Leu Glu Arg Val Phe Glu Pro Phe
            275                 280                 285

Phe Thr Gly Glu Asn Gly Ala Lys Val Ser Gly Phe Leu Arg Asp Trp
290                 295                 300

Phe Ile Tyr Met Trp Lys Asn Cys Gln Arg Thr Arg Ala His Asp Cys
305                 310                 315                 320

Asn Thr Val Thr Ser Gly Gln Arg Asn Arg Asn Ile Asp Ser Leu Pro
            325                 330                 335

Tyr Glu Ile Val Arg Tyr Phe
            340

<210> SEQ ID NO 87
<211> LENGTH: 346
<212> TYPE: PRT
<213> ORGANISM: Bacillus halodurans

<400> SEQUENCE: 87

Met Arg Gly Ile Lys Gln Ile Tyr Asp Cys Leu Tyr Ala Tyr Lys Leu
1               5                   10                  15

Gly Phe Leu Leu Leu Ile Ile Thr Asn Leu Leu Phe Ile Phe Phe Ala
                20                  25                  30

Trp Leu Ala Tyr Pro Glu Thr Phe Lys Val Leu Val Gly Leu Met Ile
            35                  40                  45

Val Phe Thr Leu Ala Thr Leu Ser Leu Ser Ile Phe Ile Ile Val Arg
        50                  55                  60

Lys Gln Asn Ile Ile Glu Ala Ala Phe Gln Glu Phe Leu Leu Glu Pro
65                  70                  75                  80

Asn Glu Met Asn Glu Glu Arg Leu Cys Arg Val Ser Pro Lys Thr His
                85                  90                  95

Trp Ser Cys Ile Arg Asp Met Gly Ser Ser Ile Arg Ser Tyr Gln Ala
            100                 105                 110

Glu Leu Asn Glu Gln Val Met Glu Leu Ala Asp Tyr Glu Asn Tyr Ile
        115                 120                 125

Glu Gly Trp Val His Glu Ile Lys Lys Pro Leu Ser Leu Met Thr Leu
    130                 135                 140

Val Leu Asp Asn Arg Arg Asp Glu Met Ser Ser Leu Val Arg His Arg
145                 150                 155                 160

Met Leu His Ile Arg Asp Gln Met Leu Gly Asp Val Glu Arg Ile Leu
                165                 170                 175

Tyr Phe Ala Arg Leu Gly Ala Ala His Lys Asp Tyr Met Phe Glu Pro
            180                 185                 190

Ile Asn Ile Leu Ala Phe Cys Lys Gln Thr Val Glu His His Gln Thr
        195                 200                 205

Leu Leu Asp Glu Ser Gly Phe Gln Val Gln Phe Ile Gly Glu Glu Met
    210                 215                 220

Glu Ile Phe Ser Asp Arg Lys Gly Leu Ala Phe Ile Val Glu Gln Ile
225                 230                 235                 240

```
Leu Ala Asn Ser Thr Lys Tyr Ala Ala Asn Gln Asp Lys Pro Ile
            245                 250                 255

Ile Lys Phe Glu Ala His Tyr Asp Lys Gly Lys Asp Gln Arg Ile Leu
                260                 265                 270

Thr Ile Arg Asp Asn Gly Pro Gly Val Ser Glu Asp Leu Pro Phe
            275                 280                 285

Ile Phe Asp Lys Gly Phe Thr Gly Arg Gly Ala Tyr Thr Arg Gln
    290                 295                 300

Ala Thr Gly Met Gly Leu Phe Leu Val Ser Lys Met Ala Tyr Asp Leu
305                 310                 315                 320

Ala Ile Gln Val Asp Ala Lys Ser Glu Leu Gly Ser Gly Leu Thr Ile
                325                 330                 335

Ser Leu Ile Phe Pro Arg Val Asn Glu Ala
            340                 345

<210> SEQ ID NO 88
<211> LENGTH: 331
<212> TYPE: PRT
<213> ORGANISM: Bacillus halodurans

<400> SEQUENCE: 88

Met Lys Leu Phe Ile Lys Asp His Leu Ser Phe Ile Leu Leu Tyr Leu
1               5                   10                  15

Ile Thr Phe Ile Cys Leu Pro Phe Ile Glu Gln Leu Asp Gly Phe
                20                  25                  30

Glu Asn His Tyr Asp Tyr Phe Ser Phe Leu Ala Ile Thr Leu Leu Met
            35                  40                  45

Ser Leu Leu Val Ile Arg Tyr Leu Arg Arg Lys Met Tyr Thr His
    50                  55                  60

Leu Lys Lys Glu Asn Leu Asp Gln Ala Asp Phe Leu Ile Tyr Arg Pro
65                  70                  75                  80

His Ala Pro Ile Glu Lys Ala Tyr Ala Asn Gln Leu Lys Glu Phe Ser
                85                  90                  95

Ser Leu Leu Lys Glu Gln Asp Thr Tyr Gln Asn Phe Leu Gln Glu
            100                 105                 110

Gln Gln Leu Leu Ile Ser His Ala Val His Gln Met Lys Thr Pro Ile
            115                 120                 125

Ser Val Met Gln Leu Leu Val Gln Ser Asn Gln Thr Asn Asp Val Lys
130                 135                 140

Ser Leu Gly Glu Trp Gln Lys Val Lys Ala Glu Cys Asp Lys Ile Tyr
145                 150                 155                 160

Phe Ser Leu Asn Gln Leu Leu Ser Tyr Ser Arg Ser Thr Gln Leu Leu
                165                 170                 175

Ser Asp Leu Lys Ile Glu Ala Met Pro Leu Lys Lys Ile Ile Gln Glu
            180                 185                 190

Val Ile Asn Asp Leu Lys Asp Tyr Phe Ile Glu Glu Leu Phe Pro
            195                 200                 205

Lys Val Thr Ile Ala Glu Glu Val Ile Leu Tyr Ser Asp Arg Lys Trp
    210                 215                 220

Met Lys Val Val Tyr Gln Leu Leu Ser Asn Ala Ile Lys Tyr Gly
225                 230                 235                 240

Glu Lys His Ser Thr Val His Ile Tyr Tyr Arg Asn Gly Gln Leu Ser
                245                 250                 255

Ile His Asn Arg Gly Glu Thr Ile Pro Lys Ser Glu Ile Asn Arg Leu
```

-continued

```
                260                 265                 270
Phe Asn Leu Phe Tyr Thr Gly Ser Lys Gly Arg Lys Arg Ser Glu Ala
                275                 280                 285

Thr Gly Ile Gly Leu Tyr Leu Val Lys Arg Ile Leu Val Thr Leu Asp
                290                 295                 300

His Pro Phe Glu Leu Thr Ser His His Gln Glu Thr Thr Phe Thr Ile
305                 310                 315                 320

Glu Leu Ser Lys Ser Ile Ser Thr Ala Ala Asp
                325                 330

<210> SEQ ID NO 89
<211> LENGTH: 351
<212> TYPE: PRT
<213> ORGANISM: Bacillus halodurans

<400> SEQUENCE: 89

Met Lys Lys Arg Arg Arg Leu Ala Gln Leu Gln Trp Gln Phe Ile Arg
1               5                   10                  15

Asn Ser Leu Ile Val Ser Phe Ala Val Leu Phe Thr Val Val Ile
                20                  25                  30

Met Thr Tyr Asp Asp Ile Ala Gly Leu Thr Met Leu Phe Asp Lys Gln
                35                  40                  45

Ile Val Arg Leu Pro Ile Leu Val Pro Ile Leu Ser Met Ile Ala
            50                  55                  60

Ile Gly Leu Ile Ala Gly Met Met Gln Ser Leu Pro Ile Lys Arg Lys
65                  70                  75                  80

Leu Asp Gln Ile Leu His Gly Val Leu Leu Tyr Glu Arg Gly Thr Phe
                85                  90                  95

Ser His Gln Ile Glu Ser Glu Gly Glu Asp Leu Ala Glu Leu Thr
                100                 105                 110

Asp Arg Leu Asn Arg Met Ala Glu Arg Val Glu Glu Gln Val Ala Ser
                115                 120                 125

Leu Gln Arg Leu Ser Ser Glu Arg Ala Lys Met Gln Glu Thr Val Lys
            130                 135                 140

Lys Ala Ala Val Thr Glu Glu Arg Gln Arg Leu Ala Arg Asp Leu His
145                 150                 155                 160

Asp Ala Val Ser Gln Gln Leu Phe Ala Ile Ser Met Met Thr Ala Ala
                165                 170                 175

Ile Lys Gln Asn Leu His Glu Ala Thr Glu Glu Val Gln Gln Gln Met
                180                 185                 190

Asp Val Val Glu Lys Met Ala Asn Thr Ala Gln Ala Glu Met Arg Ala
            195                 200                 205

Leu Leu Leu His Leu Arg Pro Ala Glu Leu Glu Gly Lys Ser Leu Gln
            210                 215                 220

Gln Gly Val Glu Tyr Leu Leu His Glu Leu Glu Gln Lys Gln Gly Phe
225                 230                 235                 240

Lys Ile Thr Lys Arg Leu Glu Pro Met Asp Glu Leu Pro Lys Gly Val
                245                 250                 255

Glu Asp Gln Leu Phe Arg Met Leu Gln Glu Ala Ile Ser Asn Ile Leu
                260                 265                 270

Arg His Ala Gln Ala His His Val Glu Val Arg Phe Trp Gln Thr Glu
                275                 280                 285

Arg Gln Val Arg Leu Lys Leu Ile Asp Asp Gly Val Gly Phe Asp Val
            290                 295                 300
```

```
Gln Lys Glu Thr His Gly Ser Tyr Gly Leu Gln Thr Met His Glu Arg
305                 310                 315                 320

Ile Asn Glu Ile Gly Gly Val Leu Asp Ile Val Ser Ala Pro Gly Lys
            325                 330                 335

Gly Thr Gln Leu Glu Ala Lys Ile Pro Ile Thr Trp Arg Gly Glu
        340                 345                 350

<210> SEQ ID NO 90
<211> LENGTH: 348
<212> TYPE: PRT
<213> ORGANISM: Bacillus licheniformis

<400> SEQUENCE: 90

Met Arg Lys Met Leu Thr Asp Lys Lys Leu Leu Leu Ile Leu Gln
1               5                   10                  15

Cys Ala Ala Ile Ala Ala Leu Leu Phe Ile Tyr Met Lys Thr Ala Ser
                20                  25                  30

Leu Gly Val Phe Ser Thr Met Leu Phe Ile Phe Leu Phe Ala Val Thr
            35                  40                  45

Ala Leu Leu Phe Thr Met Arg Leu Arg Phe Ile Asp Arg Leu Lys Leu
    50                  55                  60

Ile Glu Thr Glu Leu Lys Arg Val Ala Asp Gly Asn Leu Arg Arg Arg
65                  70                  75                  80

Leu Leu Ala Lys Gly Gly Gln Pro Phe Asn Glu Ile Ile Phe Ser Ile
                85                  90                  95

Asn Glu Leu Ile Glu Gln Leu Glu Lys Val Gln Ile Asn Ala Ala Lys
            100                 105                 110

Ser Glu Ala Ala Arg Lys Arg Leu Leu Ser Asn Ile Ser His Asp Ile
        115                 120                 125

Arg Thr Pro Leu Thr Ser Ile Ile Gly Tyr Val Asp Ala Leu Lys Asp
130                 135                 140

Gly Val Ala Ser Ser Glu Glu Lys Gln Glu Tyr Leu Asn Ile Leu
145                 150                 155                 160

Ser Lys Lys Ser Asn Ser Leu Lys Gln Leu Ile Asp Glu Ile Phe Asn
                165                 170                 175

Met Ala Lys Leu Asp Ala Asn Glu Val Gln Leu Lys Thr Glu Phe Phe
            180                 185                 190

Asp Leu Ala Glu Val Ala Arg Glu Thr Leu Ile Asp Phe Leu Pro Glu
        195                 200                 205

Leu Lys Lys His Asp Ile Asp Leu Asn Val Gln Ile Pro Glu Lys Lys
    210                 215                 220

Cys Phe Val Ile Ala Asp Arg Leu Ser Leu Ile Arg Val Ile Glu Asn
225                 230                 235                 240

Ile Val Arg Asn Gly Ile His Tyr Gly Lys Ala Gly Lys Val Leu Gly
                245                 250                 255

Ile Glu Leu Thr Glu Ser Glu His Glu Tyr Gln Leu Leu Ile Trp Asp
            260                 265                 270

Gln Gly Pro Gly Ile Pro Glu Ala Arg Leu Lys Thr Cys Leu Ile Glu
        275                 280                 285

Cys Thr Ala Glu Thr Gly Arg Glu Ala Leu Met Thr Gly Ala Ala Trp
    290                 295                 300

Gly Leu Pro Ser Pro Asn Arg Ser Ser Lys Thr Ala Asp Ala Tyr
305                 310                 315                 320

Gly His Arg Ala Ser Arg Gly Lys Lys Arg Leu Val Phe Arg Cys
                325                 330                 335
```

```
Leu Asn Lys Thr Ile Ser Asn His Leu Arg Ile Asn
            340                 345

<210> SEQ ID NO 91
<211> LENGTH: 334
<212> TYPE: PRT
<213> ORGANISM: Bacillus subtilis

<400> SEQUENCE: 91

Met Ile Lys Ala Phe Leu Ile Glu Arg Arg Ser Trp Ile Ala Ala Phe
 1               5                  10                  15

Leu Phe Gln Gln Ala Leu Met Leu Phe Ile Ala Phe Val Asp Pro Ser
                20                  25                  30

Ile Ser Phe Gly Asn Val Leu Tyr Met Val Tyr Leu Cys Ile Leu Phe
            35                  40                  45

Phe Ile Ile Phe Leu Trp Phe Arg Tyr Arg Lys Glu Thr Ala Phe Tyr
        50                  55                  60

Lys Ser Leu Lys Thr Trp Glu Asn Asn Leu Asp Val Thr Ala Ile Asn
 65                  70                  75                  80

Glu Pro Glu Thr Pro Phe Glu Ala Met Val Glu Arg Ser Ile Ala Gly
                85                  90                  95

Gln Thr Glu His Leu Lys Gln Thr Ala Ala Arg His Arg Leu Ala Leu
            100                 105                 110

Glu Asn Glu Lys Asp Glu Leu Met Ala Trp Ile His Glu Val Lys Thr
        115                 120                 125

Pro Leu Thr Ala Met His Leu Ile Ile Asp Arg Met Glu Glu Lys Ala
    130                 135                 140

Leu Lys Ser Gln Leu Ser Tyr Glu Trp Leu Arg Ile His Leu Leu Leu
145                 150                 155                 160

Asp Gln Gln Leu His Gln Lys Arg Ile Ser Phe Ile Glu Asn Asp Leu
                165                 170                 175

Ser Val Glu Phe Ile Gln Leu Gln Pro Leu Ile Phe Lys Glu Ile Lys
            180                 185                 190

Asp Leu Gln Ser Trp Cys Ile Gln Lys Gly Ile Gly Phe Asp Ile Gln
        195                 200                 205

Leu Glu Ala Lys Glu Val Leu Ser Asp Ala Lys Trp Leu Ala Phe Ile
    210                 215                 220

Ile Arg Gln Leu Leu Thr Asn Ala Val Lys Tyr Ser Glu Ala Ser Glu
225                 230                 235                 240

Ile Glu Ile Lys Ser Phe Gln Lys Gly Glu Gln Thr Gln Leu Gln Val
                245                 250                 255

Lys Asp Cys Gly Arg Gly Ile Asp Pro Lys Asp Val Pro Arg Ile Phe
            260                 265                 270

Asp Lys Gly Phe Thr Ser Thr Thr Asp His His Asp Gln Ala Ser Thr
        275                 280                 285

Gly Met Gly Leu Tyr Leu Ala Lys Lys Ala Ala Pro Leu Leu Ile
    290                 295                 300

His Ile Asp Val Glu Ser Glu Phe Gly Ala Gly Thr Val Phe Thr Leu
305                 310                 315                 320

Thr Phe Pro Ile Arg Asn Gln Phe Glu His Val Ile Ser Val
                325                 330

<210> SEQ ID NO 92
<211> LENGTH: 358
<212> TYPE: PRT
```

<213> ORGANISM: Bacillus subtilis

<400> SEQUENCE: 92

Met Arg Lys Lys Met Leu Ala Ser Leu Gln Trp Arg Ala Ile Arg Met
1               5                   10                  15

Thr Thr Gly Ile Ser Leu Leu Leu Phe Val Cys Leu Ile Ser Phe Met
            20                  25                  30

Met Phe Tyr Tyr Arg Leu Asp Pro Leu Val Leu Leu Ser Ser Ser Trp
        35                  40                  45

Phe Gly Ile Pro Phe Ile Leu Ile Leu Leu Leu Ile Ser Val Thr Val
    50                  55                  60

Gly Phe Ala Ser Gly Tyr Met Tyr Gly Asn Arg Leu Lys Thr Arg Ile
65                  70                  75                  80

Asp Thr Leu Ile Glu Ser Ile Leu Thr Phe Glu Asn Gly Asn Phe Ala
                85                  90                  95

Tyr Arg Ile Pro Pro Leu Gly Asp Asp Glu Ile Gly Leu Ala Ala Asp
            100                 105                 110

Gln Leu Asn Glu Met Ala Lys Arg Val Glu Leu Gln Val Ala Ser Leu
        115                 120                 125

Gln Lys Leu Ser Asn Glu Arg Ala Glu Trp Gln Ala Gln Met Lys Lys
130                 135                 140

Ser Val Ile Ser Glu Glu Arg Gln Arg Leu Ala Arg Asp Leu His Asp
145                 150                 155                 160

Ala Val Ser Gln Gln Leu Phe Ala Ile Ser Met Met Thr Ser Ala Val
                165                 170                 175

Leu Glu His Val Lys Asp Ala Asp Lys Thr Val Lys Arg Ile Arg
            180                 185                 190

Met Val Glu His Met Ala Gly Glu Ala Gln Asn Glu Met Arg Ala Leu
            195                 200                 205

Leu Leu His Leu Arg Pro Val Thr Leu Glu Gly Lys Gly Leu Lys Glu
        210                 215                 220

Gly Leu Thr Glu Leu Leu Asp Glu Phe Arg Lys Lys Gln Pro Ile Asp
225                 230                 235                 240

Ile Glu Trp Asp Ile Gln Asp Thr Ala Ile Ser Lys Gly Val Glu Asp
                245                 250                 255

His Leu Phe Arg Ile Val Gln Glu Ala Leu Ser Asn Val Phe Arg His
            260                 265                 270

Ser Lys Ala Ser Lys Val Thr Val Ile Leu Gly Ile Lys Asn Ser Gln
        275                 280                 285

Leu Arg Leu Lys Val Ile Asp Asn Gly Lys Gly Phe Lys Met Asp Gln
290                 295                 300

Val Lys Ala Ser Ser Tyr Gly Leu Asn Ser Met Lys Glu Arg Ala Ser
305                 310                 315                 320

Glu Ile Gly Gly Val Ala Glu Val Ile Ser Val Glu Gly Lys Gly Thr
                325                 330                 335

Gln Ile Glu Val Lys Val Pro Ile Phe Pro Glu Glu Lys Gly Glu Asn
            340                 345                 350

Glu Arg Asp Ser Ser Ile
            355

<210> SEQ ID NO 93
<211> LENGTH: 356
<212> TYPE: PRT
<213> ORGANISM: Bacillus subtilis

<400> SEQUENCE: 93

Met Leu Lys Thr Tyr Leu Ile Asp Arg Leu Ala Ile Ile Leu Phe Ser
1               5                   10                  15

Leu Leu Gly Ile Gly Ser Ala Met Leu Ile Ala Tyr Leu Ser Ile Val
            20                  25                  30

Glu Ser Gly Ala Glu Pro Ser Lys Glu Asn Met Met Tyr Ile Trp Ile
        35                  40                  45

Leu Pro Gly Thr Leu Leu Ala Ala Gly Phe Ala Ala Asp Tyr Val Arg
    50                  55                  60

Gln Phe Ser Phe Leu Thr Tyr Val Lys Lys Leu Ala Glu Gln Ala Ser
65                  70                  75                  80

Ser Ser Asn Asp Ile Gly Gln Ser Leu Lys Ala Arg Lys Pro Arg Thr
                85                  90                  95

Gly Glu Gln Ala Leu Trp Thr Lys Met Ile Asn Ala Leu Gly Gln Gln
            100                 105                 110

Tyr Glu Ser Arg Leu Ser Gln Tyr Ile Asn Gln Lys Gln His Tyr
        115                 120                 125

Thr Phe Thr Asn Gln Trp Val His His Met Lys Thr Pro Val Ser Val
130                 135                 140

Ile Ser Leu Met Ile Gln Glu Gly Lys Asn Gly Thr Ser Ser Ser Phe
145                 150                 155                 160

Pro Thr Phe Leu Glu Glu Leu Glu Asp Glu Asn Glu Arg Phe Arg His
                165                 170                 175

Gly Leu Asp Met Met Leu Gln Thr Ala Arg Leu Glu Glu Phe Ala Phe
            180                 185                 190

Asp Val Lys Pro Gln Thr Phe Asp Leu Ala Glu Met Val Arg Ser Leu
        195                 200                 205

Ile Asn Gln Glu Lys Arg Gln Phe Ile Lys Arg Arg Leu Phe Pro Thr
    210                 215                 220

Leu His Val Pro Pro Asn Ala Val Gln Ile Ser Ser Asp Gln Lys Trp
225                 230                 235                 240

Leu Ser Phe Val Val Glu Gln Ile Leu Phe Asn Ala Leu Lys Tyr Ser
                245                 250                 255

Lys Gln Gly Val Gly Asp Pro Ile Thr Ile Arg Ile Glu Thr Gln Gly
            260                 265                 270

His Glu Thr Arg Leu Ser Val Ala Asp Glu Gly Ile Gly Ile Pro Pro
        275                 280                 285

Gln Asp Leu Pro Arg Ile Phe Asp Ala Phe Phe Thr Gly Glu Asn Gly
    290                 295                 300

Arg Thr Met Lys Glu Ala Thr Gly Met Gly Leu Tyr Leu Ala Lys Gln
305                 310                 315                 320

Val Cys Ser Arg Leu Gly His Lys Leu Tyr Ala Glu Ser Lys Glu Gly
                325                 330                 335

Ala Gly Thr Val Met Thr Ile Val Phe Ser Ser Asp Thr Leu Val Asn
            340                 345                 350

Val Thr Ala Leu
        355

<210> SEQ ID NO 94
<211> LENGTH: 320
<212> TYPE: PRT
<213> ORGANISM: Bacillus subtilis

<400> SEQUENCE: 94

-continued

```
Met Leu Leu Phe Thr Ala Val Ile Ser Val Pro Met Leu Leu Leu Ala
  1               5                  10                  15

Val Ser Val Leu Met Ser Val Ile Tyr Asp Ser Met Phe Lys Pro Met
             20                  25                  30

Asn His Gly Met Pro Phe His Arg Ser Phe Ala Tyr Pro Ala Met Ile
             35                  40                  45

Val Val Phe Leu Ile Ser Leu Leu Leu Ala Phe Leu Phe Ser Lys
         50                  55                  60

Ser Ile His Ser Leu Leu His Lys Ile Asn Leu Leu Asn Gln Thr Ile
 65                  70                  75                  80

Arg His Leu Ala Ser Asp Gln Arg Val Pro Asp Lys Ile Glu Val Asp
                 85                  90                  95

Arg Ala Asp Glu Ile Gly Glu Leu Ile Lys Ser Val Asn Leu Leu Ile
             100                 105                 110

Glu Arg Thr Thr Tyr Arg Glu Leu Glu Leu Arg Gln Gln Glu Glu Ile
             115                 120                 125

Lys Lys Glu Leu Leu Gln Lys Leu Arg His Lys Ile Asn Thr Pro Leu
         130                 135                 140

Thr Ala Leu Arg Leu Gln Leu Phe Tyr Leu Glu Asp Gln Cys His Gly
145                 150                 155                 160

Gln Ala Val Phe Glu Ser Leu Tyr Gln Gln Ile Glu Tyr Ile Ser Glu
             165                 170                 175

Leu Thr Asn Glu Phe Asn Leu Tyr Ser Ala Glu Thr Leu Glu Ser Ser
             180                 185                 190

Tyr Ile Val Asn Glu Glu Val Arg Leu Asn Glu Leu Leu Glu Thr Ala
         195                 200                 205

Val Lys Lys Trp Asp Tyr Leu Tyr Ser Met Ser Gly Ile Glu Leu His
210                 215                 220

Tyr Lys Pro Ala Asp Gln Asp Val Ile Trp Met Ser Asn Thr Leu Trp
225                 230                 235                 240

Met Glu Arg Leu Phe Asp Asn Ile Phe Gln Asn Thr Leu Arg His Ser
             245                 250                 255

Lys Ala Lys Lys Met Glu Val Thr Ile Glu His Gly Asp Val Phe Ile
             260                 265                 270

Arg Asp Asp Gly Ile Gly Phe Asp Arg Asn Glu Ser Glu Gly Leu
         275                 280                 285

Gly Leu Lys Ile Ile Glu Asp Thr Cys Arg Leu Leu Ala Ile Thr Tyr
    290                 295                 300

Glu Leu His Ile Asn Asp Asn Gly Thr Gly Phe Leu Phe Ser Lys Glu
305                 310                 315                 320
```

<210> SEQ ID NO 95
<211> LENGTH: 350
<212> TYPE: PRT
<213> ORGANISM: Clostridium acetobutylicum

<400> SEQUENCE: 95

```
Met Lys Leu Arg Ile Lys Leu Pro Leu Leu Phe Leu Val Met Phe Ile
  1               5                  10                  15

Val Phe Met Val Ser Ile Gly Ile Tyr Leu Lys Phe Ile Phe Ala Leu
             20                  25                  30

Tyr Ser Pro Ile Ser Gly Ser Leu Leu Asn Ser Ser Ser Ile Gly Leu
         35                  40                  45

Leu Phe Pro Ile Phe Ala Ile Ala Cys Phe Ile Phe Val Ile Leu Ile
     50                  55                  60
```

```
Met Tyr Ile Tyr Phe Phe Ile Glu Lys Pro Ile Gly Leu Leu Asn Thr
 65                  70                  75                  80

Arg Leu Glu Arg Ile Asn Ile Val His Pro Leu Pro Ser Leu Ala Leu
             85                  90                  95

Arg Ser Asn Asp Glu Ile Gly Asp Leu Tyr Asn His Phe Asn Asn Met
            100                 105                 110

Glu Lys Arg Leu Gln Leu Ala His Lys Glu Gln Thr Asp Met Ile Ala
        115                 120                 125

Ala Ile Ala His Asp Leu Lys Ala Pro Leu Thr Ser Ile Asn Gly Phe
130                 135                 140

Ala Glu Leu Leu Ala Met Gln Lys Gly Leu Ser Glu Asn Glu Lys Gln
145                 150                 155                 160

Glu Tyr Tyr Glu Leu Ile Gln Lys Ser Lys Tyr Met Ala Glu Leu
            165                 170                 175

Ile Asn Asp Phe Leu Ser Phe Thr Lys Glu Lys Leu Asp Leu Glu Ser
            180                 185                 190

Met Thr Val Lys Pro Val Asp Ala Ser Lys Leu Phe Glu Asn Ile Ala
            195                 200                 205

Leu Glu Tyr Glu His Glu Leu Ser Gly Leu Asp Cys Glu Leu Val Tyr
210                 215                 220

Lys His Leu Phe Thr Gly Asn Met Met Leu Met Val Asn Glu Ile Met
225                 230                 235                 240

Ile Gly Arg Val Phe Gly Asn Leu Phe Ser Asn Val Val Arg Tyr Gly
                245                 250                 255

Gly Lys Asn Glu Leu Lys Val Tyr Met Thr Gly Tyr Ser Gln Gly Ser
            260                 265                 270

Tyr Ala Tyr Phe Glu Ile Glu Asp Asn Gly Ile Gly Val Pro Asp Lys
            275                 280                 285

Asp Ile Ser Ser Leu Phe Leu Lys Phe Thr Val Asp Lys Ser Arg
290                 295                 300

Gln Ile Glu Asn Gly Gly Ile Gly Leu Gly Leu Ala Ser Cys Lys Ser
305                 310                 315                 320

Ile Ile Glu Tyr His Gly Gly Glu Ile Tyr Ala Tyr Ser Ser Glu Tyr
            325                 330                 335

Gly Gly Leu Gly Ile Lys Phe Ser Leu Pro Leu Ala Lys His
            340                 345                 350

<210> SEQ ID NO 96
<211> LENGTH: 349
<212> TYPE: PRT
<213> ORGANISM: Clostridium acetobutylicum

<400> SEQUENCE: 96

Met Asn Phe Arg Ala Phe Val Lys Asp Arg Met Ala Tyr Ile Val Val
 1               5                  10                  15

Tyr Gly Leu Ser Thr Val Leu Ala Ile Leu Ile Met Asn Leu Thr Ser
             20                  25                  30

Ile Ile Asn Arg Val Tyr Ile Ser Gly Ile Asn Ile Leu Tyr Ala Phe
         35                  40                  45

Leu Ile Ser Ala Ile Phe Leu Ile Val Phe Leu Met Tyr Asp Tyr Tyr
     50                  55                  60

Lys Asn Lys Lys Phe Tyr Asn Gln Leu Asp Leu Ile Leu Lys Ser Glu
 65                  70                  75                  80

Glu Asp Leu Asp Tyr Met Leu Asn Ile Glu Arg Gly Ser Thr Leu Glu
```

```
                85                  90                  95
Gln Glu Met Phe Arg Lys Ile Leu Leu Lys Leu Tyr Arg Leu Ser Glu
            100                 105                 110

Asn Lys Thr Val Lys Tyr Glu Lys Arg His Lys Glu Tyr Ile Tyr Phe
            115                 120                 125

Val Asn Gln Trp Val His Gln Met Lys Thr Pro Val Ser Val Ile Asn
    130                 135                 140

Leu Thr Leu Gln Asp Glu Ile Asn Glu Asp Asn Arg Ala Val Phe Glu
145                 150                 155                 160

Ser Ile Ser Glu Glu Asn Glu Lys Leu Gln His Gly Ile Asp Met Met
                165                 170                 175

Leu Tyr Asn Ala Arg Leu Asn Glu Phe Asn Phe Asp Phe Ser Val Glu
            180                 185                 190

Glu Leu Ser Ile Ala Ser Val Leu Arg Gln Val Ile Asn Asn Asn Lys
        195                 200                 205

Lys Ser Leu Ile Arg His His Ile Phe Pro Arg Ile Ile Glu Lys Glu
    210                 215                 220

Asn Val Val Glu Thr Asp Arg Lys Trp Ile Lys Phe Val Ile Asn
225                 230                 235                 240

Gln Ile Val Ile Asn Ala Ile Lys Tyr Ser Lys Glu Glu Lys Gly Asp
                245                 250                 255

Lys His Ile Thr Phe Glu Ile Lys Glu Glu Ala Ser Arg Ser Thr Leu
            260                 265                 270

Lys Ile Ala Asp Glu Gly Ile Gly Ile Pro Lys Glu Asp Leu Thr Arg
        275                 280                 285

Val Phe Asn Ala Phe Phe Thr Gly Lys Asn Gly Arg Lys Thr Asp Glu
    290                 295                 300

Ser Thr Gly Met Gly Met Tyr Leu Ser Lys Lys Ile Cys Asp Ala Leu
305                 310                 315                 320

Gly His Gln Ile Phe Ala Glu Thr Asn Glu Ile Lys Gly Ala Ser Phe
                325                 330                 335

Ser Ile Val Phe Tyr Lys Gly Lys Asn Ile Phe Lys Leu
            340                 345

<210> SEQ ID NO 97
<211> LENGTH: 334
<212> TYPE: PRT
<213> ORGANISM: Clostridium acetobutylicum

<400> SEQUENCE: 97

Met Tyr Lys Lys Ile Ile Lys Asn Phe Met Lys Glu Lys Leu Ser Tyr
1               5                   10                  15

Ser Ile Ser Phe Phe Leu Ser Ser Gly Ile Ile Leu Phe Tyr Phe Tyr
            20                  25                  30

Val Ser Lys Asn Ile Thr Asp Val Val Tyr Pro Ile Phe Met Val Val
        35                  40                  45

Ser Ile Tyr Ile Ile Phe Ile Val Thr Glu Trp Phe Lys Tyr Tyr Arg
    50                  55                  60

Phe Asn Ala Asn Leu Thr Arg Gly Ile Glu Arg Glu Tyr Tyr Asp Leu
65                  70                  75                  80

Glu Ser Val Thr Pro Glu Gln Arg Met Ala Gln Glu Ala Ile Leu Lys
                85                  90                  95

Ile His Lys Asn Tyr Ala Ala Lys Ile Ser Glu Ile Asp Tyr Lys Asn
            100                 105                 110
```

-continued

```
Ser Asp Ile Lys Tyr Phe Ile Ser Gln Trp Ile His Asn Met Lys Thr
        115                 120                 125

Pro Val Ser Val Ile Asp Leu Ile Val Gln Arg Glu Lys Glu Lys Leu
    130                 135                 140

Ser Gly Asp Val Ile Lys Asn Ile Glu Glu Asn Tyr Lys Ile Lys
145                 150                 155                 160

Asn Gly Met Asp Gln Val Leu Asn Ile Ile Arg Leu Asp Glu Phe Ser
                165                 170                 175

Arg Asp Tyr Glu Pro Glu Ile Val Asp Ile Val Glu Leu Val Lys Arg
            180                 185                 190

Thr Ile Asn Leu Lys Lys Asn Gln Phe Ile Tyr Gly Asn Ala Phe Pro
        195                 200                 205

Lys Val Glu Phe His Val Asp Lys Ala Leu Val Leu Thr Asp Lys Lys
    210                 215                 220

Trp Ser Thr Phe Ile Ile Asp Gln Ile Ile Ser Asn Ser Ile Lys Tyr
225                 230                 235                 240

Ser Lys Lys Glu Glu Lys Gly Tyr Val Tyr Phe Asn Ile Val Gln Ser
                245                 250                 255

Asn Asn Lys Thr His Leu Val Ile Lys Asp Asn Gly Val Gly Ile Pro
            260                 265                 270

Lys Tyr Asp Leu Lys Arg Ile Phe Glu Pro Phe Phe Thr Gly Glu Asn
        275                 280                 285

Gly Arg Asn Phe Glu Asn Ser Thr Gly Ile Gly Leu Tyr Ile Cys Lys
    290                 295                 300

Lys Ile Ala Asp Asn Leu Gly His Glu Ile Ser Val Glu Ser Glu Ile
305                 310                 315                 320

Asn Lys Gly Thr Ile Val Lys Ile Thr Tyr Met Ala Lys Val
                325                 330

<210> SEQ ID NO 98
<211> LENGTH: 339
<212> TYPE: PRT
<213> ORGANISM: Clostridium acetobutylicum

<400> SEQUENCE: 98

Met Ser Phe Ile Arg Tyr Leu Lys Asp Asn Phe Arg Phe Ile Leu Leu
  1               5                  10                  15

Tyr Val Leu Leu Gly Ala Phe Val Ser Ala Phe Thr Tyr Leu Asp Glu
                 20                  25                  30

Lys Asn Arg Met Leu Ser Ser Asn Ile Gly Tyr Met Ile Phe Val Met
             35                  40                  45

Phe Phe Ile Leu Leu Ile Phe Leu Cys Val Asp Tyr Ser Ile Lys Asn
         50                  55                  60

Lys His Ile Lys Lys Leu Ile Ala Asn Gly Glu Ile Lys Asp Lys Thr
 65                  70                  75                  80

Pro Ile Leu Pro Glu Pro Leu Glu Tyr Lys Asp Glu Val Tyr Ile Ser
                 85                  90                  95

Ile Ile Glu Asp Leu Tyr Lys Asp Tyr Asn Glu Arg Ile Val Ser Leu
            100                 105                 110

Glu Lys Glu Phe Glu Asp Asn Asn Glu Phe Met Thr Ala Trp Ile His
        115                 120                 125

Glu Ile Lys Thr Pro Ile Ala Thr Ala Lys Leu Leu Leu Glu Ser Gly
    130                 135                 140

Glu Ile Asp Ser Gln Leu Phe Met Glu Glu Ile Glu Lys Ile Asp Asp
145                 150                 155                 160
```

-continued

```
Tyr Val Glu Lys Val Leu Tyr Tyr Ser Arg Ser Asp Asn Phe Ser Lys
                165                 170                 175

Asp Tyr Ile Ile Ser Glu Val Asn Ile Ser Lys Leu Ile Lys Glu Cys
            180                 185                 190

Ile Lys Ser His Ser Lys Ile Phe Ile Lys His Ile Lys Leu Lys
        195                 200                 205

Leu Glu Ile Asp Glu Arg Phe Asn Val Glu Thr Asp Lys Lys Trp Phe
    210                 215                 220

Leu Phe Ile Leu Asn Gln Ile Ser Asn Ala Leu Lys Tyr Thr Asn
225                 230                 235                 240

Asp Met Gly Asn Ile Ile Lys Ala Phe Glu Asp Asn Glu Lys
            245                 250                 255

Val Val Ile Ile Glu Asp Asn Gly Ile Gly Ile Lys Lys Glu Asp Leu
            260                 265                 270

Asp Arg Ile Phe Ser Lys Ser Phe Thr Gly Tyr Asn Gly Arg Lys Glu
        275                 280                 285

Asn Ser Lys Ala Thr Gly Met Gly Leu Tyr Leu Ser Asn Lys Leu Ala
    290                 295                 300

Glu Lys Leu Gly His Asn Ile Thr Ile Glu Ser Lys Tyr Asn Glu Gly
305                 310                 315                 320

Thr Lys Leu Tyr Ile His Phe Pro Lys Trp Cys Asp Tyr Tyr Asp Val
            325                 330                 335

Thr Lys Met

<210> SEQ ID NO 99
<211> LENGTH: 336
<212> TYPE: PRT
<213> ORGANISM: Clostridium perfringens

<400> SEQUENCE: 99

Met Lys Leu Arg Asp Tyr Phe Glu Asp Lys Thr Phe Phe Leu Ile Val
  1               5                  10                  15

Asn Phe Ile Ile Phe Ala Thr Ile Gly Val Leu Leu Phe Ile Gly Asn
             20                  25                  30

Val Gly Ser Gly Ile Ile Phe Leu Ile Gly Cys Phe Trp Phe Ile Pro
         35                  40                  45

Leu Phe Thr Tyr Ile Ile Leu Asp Phe Tyr Lys Ser Lys Lys Phe Tyr
    50                  55                  60

Asp Asn Ile Ser Ile Thr Leu Asp Lys Leu Asp Arg Lys Tyr Leu Leu
65                  70                  75                  80

Pro Glu Val Ile Glu Glu Pro Asn Phe Tyr His Gly Lys Phe Leu Tyr
                85                  90                  95

Glu Val Leu Lys Glu Thr Asp Lys Asp Met His Glu His Val Lys Lys
            100                 105                 110

Tyr Ile Leu Glu Gln Lys Glu Tyr Arg Glu Tyr Ile Glu Thr Trp Val
        115                 120                 125

His Glu Ile Lys Thr Pro Ile Ala Ser Thr Arg Leu Ile Leu Glu Asn
    130                 135                 140

Asn Glu Ser Glu Ser Ser Glu Asn Ile Lys Lys Glu Ile Lys Lys Ile
145                 150                 155                 160

Glu Glu Tyr Ile Asp Gln Ala Leu Tyr Tyr Ala Arg Ser Thr Asp Val
                165                 170                 175

Ser Lys Asp Tyr Ile Val Lys Glu Phe Ser Leu Gly Lys Ser Val Arg
            180                 185                 190
```

```
Asn Val Ile Lys Lys Asn Ser Arg Asp Phe Ile Asn Lys Arg Ile Ala
            195                 200                 205

Ile Asp Leu Glu Asp Leu Asp Tyr Lys Val Tyr Ser Asp Glu Lys Trp
210                 215                 220

Val Glu Phe Ile Ile Asn Gln Val Ile Asn Asn Ala Ile Lys Tyr Ser
225                 230                 235                 240

Ala Lys Asn Ser Arg Val Lys Ile Phe Ala Asn Lys Ser Lys Asn Ser
            245                 250                 255

Ile Thr Leu Lys Ile Lys Asp Ser Gly Val Gly Ile His Asn Lys Asp
            260                 265                 270

Leu Gly Arg Val Phe Glu Lys Gly Phe Thr Gly Glu Asn Gly Arg Arg
            275                 280                 285

Phe Thr Lys Ser Thr Gly Met Gly Leu Tyr Leu Cys Lys Asn Leu Cys
            290                 295                 300

Asp Lys Leu Gly Leu Gly Leu Lys Ile Thr Ser Glu Glu Asn Glu Gly
305                 310                 315                 320

Thr Glu Val Asn Ile Ile Phe Pro Ile Gly Asp Ala Ile Ile Ala Asn
            325                 330                 335

<210> SEQ ID NO 100
<211> LENGTH: 341
<212> TYPE: PRT
<213> ORGANISM: Enterococcus faecalis

<400> SEQUENCE: 100

Met Thr Ile Leu Lys Tyr Leu Lys Asp Arg Trp Leu Leu Leu Ile Gly
1               5                   10                  15

Trp Leu Phe Phe Leu Phe Leu Thr Cys Phe Ile Leu Trp Leu Ala Pro
            20                  25                  30

Asn Val Arg Leu Asp Trp Thr Val Val Gly Tyr Ile Phe Leu Leu Gln
            35                  40                  45

Ser Val Phe Leu Ser Leu Phe Leu Thr Ile Asp Tyr Tyr Leu Lys Arg
    50                  55                  60

Lys Trp Trp Leu Ser Leu Ala Thr Glu Lys Glu Pro Pro Ser Leu Gln
65                  70                  75                  80

Glu Tyr Leu Asn Thr Ala Glu Lys Glu Glu Leu Leu Val Gln Thr
                85                  90                  95

Tyr Ile Asn Gly Leu Leu Gln Glu His Gln Gln Thr Met Gln Gln Ala
            100                 105                 110

Ile Asn Asn Gln Gln Asp Gln Lys Asp Tyr Ile Asp Ser Trp Val His
            115                 120                 125

Glu Ile Lys Val Pro Leu Ala Ala Ile Thr Leu Leu Val Gln Ser Val
            130                 135                 140

Glu Asp Asp Ile Pro Glu Lys Lys Tyr Leu Leu Glu Asn Glu Leu
145                 150                 155                 160

Gly Lys Ile Asp Glu Tyr Val Glu Gln Val Leu Tyr Tyr Ala Arg Leu
            165                 170                 175

Asp Ser Phe Ser Arg Asp Tyr Leu Gln Glu Tyr Ser Leu Lys Glu
            180                 185                 190

Ile Val Gln Ser Val Val Arg Thr Gln Ala Asn Tyr Phe Ile Gln Lys
            195                 200                 205

Arg Leu Gln Phe Ser Ile Glu Gly Glu Asp Glu Ala Val Leu Thr Asp
210                 215                 220

Arg Lys Trp Val Ile Phe Ile Phe Arg Gln Leu Leu Ser Asn Ala Val
```

```
                225                 230                 235                 240
Lys Tyr Thr Pro Glu Gly Gly Thr Ile Thr Val Leu Ile Ser Lys Asn
                    245                 250                 255

Lys Gln Gly Ile Tyr Leu Ser Leu Lys Asp Ser Gly Ile Gly Ile Pro
                260                 265                 270

Thr Gln Asp Gln Arg Arg Ile Phe Asp Lys Gly Phe Thr Gly Glu Asn
            275                 280                 285

Gly Arg Lys Ser Glu Gln His Ser Thr Gly Ile Gly Leu Tyr Leu Ala
        290                 295                 300

His Ser Leu Ala Lys Lys Leu Gly His Asp Leu Thr Val Glu Ser Thr
305                 310                 315                 320

Glu Gly Gln Gly Thr Thr Met Thr Leu Phe Phe Pro Ser Leu Ser Tyr
                325                 330                 335

Tyr Asn Glu Val Lys
            340

<210> SEQ ID NO 101
<211> LENGTH: 339
<212> TYPE: PRT
<213> ORGANISM: Actobacillus sakei

<400> SEQUENCE: 101

Met Thr Phe Lys Lys Phe Ile Arg Asp His Leu Phe His Ile Val Phe
1               5                   10                  15

Phe Phe Gly Gly Met Phe Val Leu Asp Ile Val Leu Trp Leu Asp Pro
                20                  25                  30

His Met Arg Leu Ala Lys Glu Thr Leu Met Tyr Leu Asp Phe Leu Leu
            35                  40                  45

Thr Ile Phe Phe Cys Ala Phe Leu Ile Gly Leu Tyr Leu Tyr His Arg
        50                  55                  60

Lys Trp Phe Arg Thr Ile Gln Ile Arg Leu Asn Ala Lys Glu Asp Ala
65                  70                  75                  80

Leu Asn Trp Pro Leu Thr Gly Ala Thr Ser Ala Glu Lys Gln Tyr Phe
                85                  90                  95

Gln Lys Tyr Val Asn Ser Leu Leu Asp Tyr His Gln Gln Ser Ile Glu
                100                 105                 110

Arg Leu Met His Ala Gln Gln Asp Gln Lys Asp Phe Ile Asp Gly Trp
            115                 120                 125

Val His Glu Ser Lys Val Pro Leu Ala Ala Thr Gln Leu Leu Val Glu
        130                 135                 140

Ser Ile Glu Asp Gln Ile Pro Glu Glu Lys Phe Asn Gln Leu Thr Asp
145                 150                 155                 160

Glu Leu Val Gln Ile Glu His Tyr Val Glu Gln Val Leu Tyr Tyr Ser
                165                 170                 175

Arg Leu Asp Ser Phe Ser Lys Asp Tyr Leu Val Gln Glu Tyr Ala Leu
            180                 185                 190

Lys Pro Leu Ile Asn Gln Thr Ile Arg Gln Asn Arg Asn Tyr Phe Ile
        195                 200                 205

Gln Asn Arg Ile Gln Phe Lys Leu Thr Gly Glu Glu Gln Thr Val Leu
    210                 215                 220

Thr Asp Ala Lys Trp Leu Val Phe Ile Leu Asn Gln Ile Val Ser Asn
225                 230                 235                 240

Ala Leu Lys Tyr Thr Pro Gln Asn Gly Gln Ile Thr Ile Asp Leu Ala
                245                 250                 255
```

```
His Asp Glu Gln Gly Val Trp Leu Ser Val Ser Asp Ser Gly Ile Gly
            260                 265                 270

Ile Pro Ala Glu Asp Leu Pro Arg Val Phe Asp Lys Gly Phe Thr Gly
        275                 280                 285

Gln Asn Gly Arg Gln Ser Asn Gln Arg Ser Thr Gly Leu Gly Leu Tyr
    290                 295                 300

Leu Ala Lys Ser Leu Ser Asn Lys Leu Gly His Ala Thr Leu Cys Gln
305                 310                 315                 320

Leu Asn Ala Arg Lys Trp Cys Asp Phe Gln Ile Thr Leu Tyr Leu Phe
                325                 330                 335

Lys Leu Leu

<210> SEQ ID NO 102
<211> LENGTH: 346
<212> TYPE: PRT
<213> ORGANISM: Listeria monocytogenes

<400> SEQUENCE: 102

Met Asn Trp Trp Ser Tyr Leu Lys Asp Lys Arg Phe Leu Leu Phe
  1               5                  10                  15

Phe Cys Ser Ile Met Phe Phe Val Gly Val Leu Ile Ser Ile Asp Pro
                 20                  25                  30

Asn Ser Lys Leu Thr Leu Gly Asn Phe Ile Tyr Leu Tyr Val Phe Val
             35                  40                  45

Leu Val Phe Leu Leu Ser Tyr Leu Val Leu Gly Tyr Phe Phe Lys Tyr
     50                  55                  60

Ser Tyr Trp Arg Glu Met Lys Glu Leu Val Ser Gly Glu Ile Glu Glu
 65                  70                  75                  80

Asn Ile Ile Glu Leu Leu Pro Lys Pro Arg Thr Arg Glu Gln Ala Phe
                 85                  90                  95

Phe Asn Gln Leu Met Ala Lys Lys His Lys Glu Glu Leu Arg Thr Ile
            100                 105                 110

Ser Lys Leu Gln Asp Lys Gln Gln Glu Tyr His Asp Phe Ile Leu Tyr
        115                 120                 125

Trp Val His Glu Val Lys Thr Pro Val Val Ala Ser Lys Met Leu Ile
    130                 135                 140

Asn Asn Pro Asp Leu Asn Asp Thr Glu Thr Ile Phe Lys Gln Ile Asp
145                 150                 155                 160

Glu Glu Leu Thr Thr Ile Asp Lys Leu Val Met Gln Ala Leu Tyr Phe
                165                 170                 175

Ser Arg Leu Asp Thr Phe Ser Lys Asp Tyr Phe Ile Gln Glu Gln Asn
            180                 185                 190

Leu Gly Val Val Val Arg Glu Ser Val Lys Arg His Ser Lys Leu Phe
        195                 200                 205

Ile Gly Lys Lys Met Lys Leu Asp Leu Gln Asn Val Asp Met Asp Val
    210                 215                 220

Arg Thr Asp Ser Lys Trp Leu Gly Phe Ile Leu Asp Gln Ile Leu Ser
225                 230                 235                 240

Asn Ala Leu Lys Tyr Thr Lys Ser Gly Gly Glu Val Lys Ile Trp Cys
                245                 250                 255

Asp Thr Glu Ala Ser Gly Lys Lys Val Leu His Met Lys Asp Asn Gly
            260                 265                 270

Arg Gly Ile Lys Glu Glu Asp Leu Pro Arg Val Phe Glu Gln Gly Phe
        275                 280                 285
```

-continued

```
Thr Gly Asn Ile Gly Arg Gln Glu Lys Lys Ala Thr Gly Met Gly Leu
    290                 295                 300
Tyr Leu Ala Lys Gln Met Ala Lys Leu Gly His Glu Ile Cys Ile
305                 310                 315                 320
Gln Ser Glu Ser Gly Val Gly Thr Glu Val Lys Ile Tyr Phe Glu Gln
                325                 330                 335
Lys Asp Asp Tyr Leu Leu Ile Ala Lys Asp
                340                 345
```

<210> SEQ ID NO 103
<211> LENGTH: 343
<212> TYPE: PRT
<213> ORGANISM: Staphylococcus aureus

<400> SEQUENCE: 103

```
Met Asn Asn Leu Lys Trp Val Ala Tyr Phe Leu Lys Ser Arg Met Asn
 1               5                  10                  15
Trp Ile Phe Trp Ile Leu Phe Leu Asn Leu Leu Met Leu Gly Ile Ser
                20                  25                  30
Leu Ile Asp Tyr Asp Phe Pro Ile Asp Ser Leu Phe Tyr Ile Val Ser
                35                  40                  45
Leu Asn Leu Ser Leu Thr Met Ile Phe Leu Ile Leu Thr Tyr Phe Lys
            50                  55                  60
Glu Val Lys Leu Tyr Lys His Phe Asp Lys Asp Lys Glu Ile Glu Glu
 65                  70                  75                  80
Ile Lys His Lys Asp Leu Ala Glu Thr Pro Phe Gln Arg His Thr Val
                85                  90                  95
Asp Tyr Leu Tyr Arg Gln Ile Ser Ala His Lys Glu Lys Val Val Glu
                100                 105                 110
Gln Gln Leu Gln Leu Asn Met His Glu Gln Thr Ile Thr Glu Phe Val
            115                 120                 125
His Asp Ile Lys Thr Pro Val Thr Ala Met Lys Leu Leu Ile Asp Gln
130                 135                 140
Glu Lys Asn Gln Glu Arg Lys Gln Ala Leu Leu Tyr Glu Trp Ser Arg
145                 150                 155                 160
Ile Asn Ser Met Leu Asp Thr Gln Leu Tyr Ile Thr Arg Leu Glu Ser
                165                 170                 175
Gln Arg Lys Asp Met Tyr Phe Asp Tyr Val Ser Leu Lys Arg Met Val
                180                 185                 190
Ile Asp Glu Ile Gln Leu Thr Arg His Ile Ser Gln Val Lys Gly Ile
            195                 200                 205
Gly Phe Asp Val Asp Phe Lys Val Asp Tyr Val Tyr Thr Asp Ile
210                 215                 220
Lys Trp Cys Arg Met Ile Ile Arg Gln Ile Leu Ser Asn Ala Leu Lys
225                 230                 235                 240
Tyr Ser Glu Asn Phe Asn Ile Glu Ile Gly Thr Glu Leu Asn Asp Gln
                245                 250                 255
His Val Ser Leu Tyr Ile Lys Asp Tyr Gly Arg Gly Ile Ser Lys Lys
                260                 265                 270
Asp Met Pro Arg Ile Phe Glu Arg Gly Phe Thr Ser Thr Ala Asn Arg
            275                 280                 285
Asn Glu Thr Thr Ser Ser Gly Met Gly Leu Tyr Leu Val Asn Ser Val
290                 295                 300
Lys Asp Gln Leu Gly Ile His Leu Gln Val Thr Ser Thr Val Gly Lys
305                 310                 315                 320
```

-continued

Gly Thr Thr Val Arg Leu Ile Phe Pro Leu Gln Asn Glu Ile Val Glu
                325                 330                 335

Arg Met Ser Glu Val Thr Asn
            340

<210> SEQ ID NO 104
<211> LENGTH: 295
<212> TYPE: PRT
<213> ORGANISM: Staphylococcus aureus

<400> SEQUENCE: 104

Met Thr Phe Leu Lys Ser Ile Thr Gln Glu Ile Ala Ile Val Ile Val
  1               5                  10                  15

Ile Phe Ala Leu Phe Gly Leu Met Phe Tyr Leu Tyr His Leu Pro Leu
                 20                  25                  30

Glu Ala Tyr Leu Leu Ala Leu Gly Val Ile Leu Leu Leu Leu Leu Ile
             35                  40                  45

Phe Ile Gly Ile Lys Tyr Leu Ser Phe Val Lys Thr Ile Ser Gln Gln
 50                  55                  60

Gln Gln Ile Glu Asn Leu Glu Thr Ala Leu Tyr Gln Leu Lys Asn Glu
 65                  70                  75                  80

Gln Ile Glu Tyr Lys Asn Asp Val Glu Ser Tyr Phe Leu Thr Trp Val
                 85                  90                  95

His Gln Met Lys Thr Pro Ile Thr Ala Ala Gln Leu Leu Leu Glu Arg
                100                 105                 110

Asp Glu Pro Asn Val Val Asn Arg Val Arg Gln Glu Val Ile Gln Ile
            115                 120                 125

Asp Asn Tyr Thr Ser Leu Ala Leu Ser Tyr Leu Lys Leu Leu Asn Glu
130                 135                 140

Thr Ser Asp Ile Ser Val Thr Lys Ile Ser Ile Asn Asn Ile Ile Arg
145                 150                 155                 160

Pro Ile Ile Met Lys Tyr Ser Ile Gln Phe Ile Asp Gln Lys Thr Lys
                165                 170                 175

Ile His Tyr Glu Pro Cys His His Glu Val Leu Thr Asp Val Arg Trp
            180                 185                 190

Thr Ser Leu Met Ile Glu Gln Leu Ile Asn Asn Ala Leu Lys Tyr Ala
        195                 200                 205

Arg Gly Lys Asp Ile Trp Ile Glu Phe Asp Glu Gln Ser Asn Gln Leu
210                 215                 220

His Val Lys Asp Asn Gly Ile Gly Ile Ser Glu Ala Asp Leu Pro Lys
225                 230                 235                 240

Ile Phe Asp Lys Gly Tyr Ser Tyr Asn Gly Gln Arg Gln Ser Asn
                245                 250                 255

Ser Ser Gly Ile Gly Leu Phe Ile Val Lys Gln Ile Ser Thr His Thr
            260                 265                 270

Asn His Pro Val Ser Val Val Ser Lys Gln Asn Glu Gly Thr Thr Phe
        275                 280                 285

Thr Ile Gln Phe Pro Asp Glu
        290                 295

<210> SEQ ID NO 105
<211> LENGTH: 343
<212> TYPE: PRT
<213> ORGANISM: Staphylococcus aureus

<400> SEQUENCE: 105

```
Met Asn Asn Leu Lys Trp Val Ala Tyr Phe Leu Lys Ser Arg Met Asn
 1               5                  10                  15

Trp Ile Phe Trp Ile Leu Phe Leu Asn Leu Leu Met Leu Gly Ile Ser
                 20                  25                  30

Leu Ile Asp Tyr Asp Phe Pro Ile Asp Ser Leu Phe Tyr Ile Val Ser
             35                  40                  45

Leu Asn Leu Ser Leu Thr Met Ile Phe Leu Ile Leu Thr Tyr Phe Lys
         50                  55                  60

Glu Val Lys Leu Tyr Lys His Phe Asp Lys Asp Lys Glu Ile Glu Glu
 65                  70                  75                  80

Ile Lys His Lys Asp Leu Ala Glu Thr Pro Phe Gln Arg His Thr Val
                 85                  90                  95

Asp Tyr Leu Tyr Arg Gln Ile Ser Ala His Lys Glu Lys Val Val Glu
             100                 105                 110

Gln Gln Leu Gln Leu Asn Met His Glu Gln Thr Ile Thr Glu Phe Val
             115                 120                 125

His Asp Ile Lys Thr Pro Val Thr Ala Met Lys Leu Leu Ile Asp Gln
130                 135                 140

Glu Lys Asn Gln Glu Arg Lys Gln Ala Leu Leu Tyr Glu Trp Ser Arg
145                 150                 155                 160

Ile Asn Ser Met Leu Asp Thr Gln Leu Tyr Ile Thr Arg Leu Glu Ser
                 165                 170                 175

Gln Arg Lys Asp Met Tyr Phe Asp Tyr Val Ser Leu Lys Arg Met Val
             180                 185                 190

Ile Asp Glu Ile Gln Leu Thr Arg His Ile Ser Gln Val Lys Gly Ile
         195                 200                 205

Gly Phe Asp Val Asp Phe Lys Val Asp Asp Tyr Val Tyr Thr Asp Ile
         210                 215                 220

Lys Trp Cys Arg Met Ile Ile Arg Gln Ile Leu Ser Asn Ala Leu Lys
225                 230                 235                 240

Tyr Ser Glu Asn Phe Asn Ile Glu Ile Gly Thr Glu Leu Asn Asp Gln
                 245                 250                 255

His Val Ser Leu Tyr Ile Lys Asp Tyr Gly Arg Gly Ile Ser Lys Lys
             260                 265                 270

Asp Met Pro Arg Ile Phe Glu Arg Gly Phe Thr Ser Thr Ala Asn Arg
             275                 280                 285

Asn Glu Thr Thr Ser Ser Gly Met Gly Leu Tyr Leu Val Asn Ser Val
         290                 295                 300

Lys Asp Gln Leu Gly Ile His Leu Gln Val Thr Ser Thr Val Gly Lys
305                 310                 315                 320

Gly Thr Thr Val Arg Leu Ile Phe Pro Leu Gln Asn Glu Ile Val Glu
                 325                 330                 335

Arg Met Ser Glu Val Thr Asn
             340

<210> SEQ ID NO 106
<211> LENGTH: 353
<212> TYPE: PRT
<213> ORGANISM: Staphylococcus aureus

<400> SEQUENCE: 106

Met Leu Ser Ile Arg Ser Gln Ile Ile Ile Gly Val Val Ser Ser Ile
 1               5                  10                  15

Pro Leu Thr Ser Thr Ile Leu Ala Ile Ala Tyr Ile Leu Met Trp Phe
```

```
                    20                  25                  30
Asn Gly His Met Thr Leu Thr Leu Thr Thr Ile Ile Thr Ser
         35                  40                  45

Cys Leu Thr Leu Leu Ile Cys Ser Ile Phe Ile Asn Pro Leu Ile Gln
 50                  55                  60

Lys Ile Lys Gln Phe Asn Ile Lys Thr Lys Pro Phe Ala Asn Gly Asn
 65                  70                  75                  80

Tyr Ala Ser Asn Asp Lys Thr Phe Asn Ser Pro Lys Glu Ile Tyr Glu
                 85                  90                  95

Leu Asn Gln Ser Phe Asn Lys Met Ala Ser Glu Ile Thr Gln Gln Met
                100                 105                 110

Asn Gln Ile Lys Ser Glu Gln Gln Glu Lys Thr Glu Leu Ile Gln Asn
            115                 120                 125

Leu Ala His Asp Leu Lys Thr Pro Leu Ala Ser Ile Ile Ser Tyr Ser
    130                 135                 140

Glu Gly Leu Arg Asp Gly Ile Ile Thr Lys Asp His Glu Ile Lys Glu
145                 150                 155                 160

Ser Tyr Asp Ile Leu Ile Lys Gln Ala Asn Arg Leu Ser Thr Leu Phe
                165                 170                 175

Asp Asp Met Thr His Ile Ile Thr Leu Asn Thr Gly Lys Thr Tyr Pro
                180                 185                 190

Pro Glu Leu Ile Gln Leu Asp Gln Leu Leu Val Ser Ile Leu Pro Thr
            195                 200                 205

Ile Gly Ala Thr Tyr Pro Asn Met Lys Thr Ala Thr Leu Glu Val Asn
    210                 215                 220

Phe Cys Lys Arg Asn Ser Cys Ile Leu Ser Ile Ser Lys Arg Gln Leu
225                 230                 235                 240

Glu Arg Ile Leu Asn Lys Thr Tyr Leu Met Asn Ala Leu Lys Phe Ser
                245                 250                 255

Asn Val Gly Ser Arg Ile Asp Ile Asn Ile Ser Glu Asn Glu Asp Gln
                260                 265                 270

Asp Thr Ile Asp Ile Ala Ile Ser Asp Gly Gly Ile Gly Ile Ile Pro
            275                 280                 285

Glu Leu Gln Glu Arg Ile Phe Glu Arg Thr Phe Arg Val Glu Asn Ser
    290                 295                 300

Arg Asn Thr Lys Thr Gly Gly Ser Gly Leu Gly Leu Tyr Ile Ala Asn
305                 310                 315                 320

Glu Leu Ala Gln Gln Asn Asn Ala Lys Ile Ser Val Arg Ser Asp Ile
                325                 330                 335

Asp Val Gly Thr Thr Val Thr Val Thr Leu His Lys Leu Asp Ile Thr
            340                 345                 350

Ser

<210> SEQ ID NO 107
<211> LENGTH: 298
<212> TYPE: PRT
<213> ORGANISM: Staphylococcus epidermidis

<400> SEQUENCE: 107

Met Lys Phe Ala Tyr Ile Gln Ser Ile Arg Asn Glu Ile Ser Ile Ile
 1               5                  10                  15

Leu Ile Ile Leu Leu Phe Phe Ala Leu Ile Phe Tyr Val Phe Ser Leu
                20                  25                  30

Pro Phe Asp Ala Tyr Val Leu Ala Ile Ser Ile Ile Leu Leu Leu Met
```

```
                35                  40                  45
Cys Val Arg Trp Trp Ile Lys Tyr Leu Ser Phe Lys Lys Asn Glu His
 50                  55                  60
Leu Lys Asp Lys Val Ala Tyr Leu Glu His Glu Leu Ala His Val Lys
 65                  70                  75                  80
Asn Gln Gln Ile Glu Tyr Arg Asn Asp Val Glu Ser Tyr Phe Leu Thr
                 85                  90                  95
Trp Val His Gln Ile Lys Thr Pro Ile Thr Ala Ser Gln Leu Leu Leu
                100                 105                 110
Glu Arg Asn Glu Glu Asn Val Val Asn Arg Val Arg Gln Glu Ile Val
                115                 120                 125
His Ile Asp Asn Tyr Thr Ser Leu Ala Leu Ser Tyr Leu Lys Leu Leu
130                 135                 140
Asn Glu Glu Ser Asp Met Thr Ile Thr Lys Val Thr Val Asp Asp Leu
145                 150                 155                 160
Ile Arg Pro Leu Ile Leu Lys Tyr Arg Ile Gln Phe Ile Glu Gln Lys
                165                 170                 175
Thr Gln Ile His Tyr Glu Lys Ser Glu Asp Ile Ile Leu Thr Asp Ala
                180                 185                 190
Gln Trp Ala Ser Ile Met Ile Glu Gln Leu Leu Asn Asn Ala Leu Lys
                195                 200                 205
Tyr Ala Lys Gly Lys Asp Ile Trp Ile Asp Phe Asp Val Ala Asn Gln
                210                 215                 220
Thr Leu Gln Ile Lys Asp Asn Gly Ile Gly Ile Ser Lys Ala Asp Ile
225                 230                 235                 240
Pro Lys Ile Phe Asp Lys Gly Tyr Ser Gly Phe Asn Gly Arg Leu Asn
                245                 250                 255
Glu Gln Ser Thr Gly Ile Gly Leu Phe Ile Val Gln His Ile Ala Asn
                260                 265                 270
His Leu Asn Ile Gln Val Thr Val Gln Ser Glu Leu Asn His Gly Thr
                275                 280                 285
Val Phe Phe Ile His Phe Thr Lys Glu Lys
                290                 295

<210> SEQ ID NO 108
<211> LENGTH: 343
<212> TYPE: PRT
<213> ORGANISM: Staphylococcus epidermidis

<400> SEQUENCE: 108

Met Asn Asn Phe Arg Trp Phe Trp Phe Phe Ile Lys Ser Arg Ile Asn
  1               5                  10                  15
Trp Ile Leu Trp Ile Leu Phe Leu Asn Ile Ile Leu Leu Gly Val Ala
                 20                  25                  30
Tyr Ile Asp Tyr Glu Ile Ser Val Glu Ser Val Phe Tyr Ile Val Ile
                 35                  40                  45
Leu Asn Val Gly Leu Ser Ile Leu Phe Leu Leu Phe Thr Phe Val Lys
 50                  55                  60
Glu Val Arg Leu Ser Lys His Phe Tyr Glu Asp Lys Glu Ile Glu Glu
 65                  70                  75                  80
Ile Lys His Lys Asp Leu Ala Glu Thr Pro Phe Gln Gln Val Ile
                 85                  90                  95
Asp Tyr Leu Tyr Arg His Ile Ala Ala Gln Lys Glu Lys Val Val Glu
                100                 105                 110
```

-continued

Gln Gln Leu Gln Ile Lys Asn His Glu Gln Thr Ile Thr Glu Phe Val
        115                 120                 125

His Asp Ile Lys Thr Pro Val Thr Ala Met Lys Leu Leu Ile Asp Gln
    130                 135                 140

Glu Asn Asp Asp Gln Arg Lys Arg Ala Leu Leu Phe Glu Trp Ser Arg
145                 150                 155                 160

Ile Asn Glu Met Leu Asp Lys Gln Leu Tyr Leu Thr Arg Leu Glu Thr
                165                 170                 175

His His Arg Asp Met Tyr Phe Asp Tyr Ile Ser Leu Lys Arg Met Val
            180                 185                 190

Ile Asp Glu Ile Gln Val Thr Arg His Ile Ser Gln Ala Lys Gly Ile
        195                 200                 205

Gly Phe Glu Leu Asp Phe Lys Asp Glu Gln Lys Val Tyr Thr Asp Val
    210                 215                 220

Lys Trp Cys Arg Met Met Ile Arg Gln Val Leu Ser Asn Ser Leu Lys
225                 230                 235                 240

Tyr Ser Asp Asn Ser Thr Ile Asn Leu Ser Gly Tyr Asn Ile Glu Gly
                245                 250                 255

His Val Leu Lys Ile Lys Asp Tyr Gly Arg Gly Ile Ser Lys Arg
            260                 265                 270

Asp Leu Pro Arg Ile Phe Asp Arg Gly Phe Thr Ser Thr Asp Arg
    275                 280                 285

Asn Asp Thr Ala Ser Ser Gly Met Gly Leu Tyr Leu Val Gln Ser Val
290                 295                 300

Lys Glu Gln Leu Gly Ile Glu Val Lys Val Asp Ser Ile Val Gly Lys
305                 310                 315                 320

Gly Thr Thr Phe Tyr Phe Ile Phe Pro Gln Gln Asn Glu Ile Ile Glu
                325                 330                 335

Arg Met Ser Lys Val Thr Arg
            340

<210> SEQ ID NO 109
<211> LENGTH: 312
<212> TYPE: PRT
<213> ORGANISM: Streptococcus agalactiae

<400> SEQUENCE: 109

Met Ile Arg Gln Phe Leu Arg Glu His Leu Ile Trp Tyr Ile Leu Tyr
1               5                   10                  15

Ile Met Met Phe Val Leu Phe Phe Ile Ser Phe Tyr Leu Tyr His Leu
            20                  25                  30

Pro Met Pro Tyr Leu Phe Asn Ser Leu Gly Leu Asn Val Ile Val Leu
        35                  40                  45

Leu Gly Ile Ser Ile Trp Gln Tyr Ser Arg Tyr Arg Lys Lys Met Leu
    50                  55                  60

His Leu Lys Tyr Phe Asn Ser Ser Gln Asp Pro Thr Phe Glu Leu Gln
65                  70                  75                  80

Pro Ser Asp Tyr Ala Tyr Phe Asn Ile Ile Thr Gln Leu Glu Ala Arg
                85                  90                  95

Glu Ala Gln Lys Val Ser Glu Thr Ile Glu Gln Thr Asn His Val Ala
            100                 105                 110

Leu Met Ile Lys Met Trp Ser His Gln Met Lys Val Pro Leu Ala Ala
        115                 120                 125

Ile Ser Leu Met Ala Gln Thr Asn His Leu Asp Pro Lys Glu Val Glu
    130                 135                 140

```
Gln Gln Leu Leu Lys Leu Gln His Tyr Leu Glu Thr Leu Leu Ala Phe
145                 150                 155                 160

Leu Lys Phe Arg Gln Tyr Arg Asp Asp Phe Arg Phe Glu Ala Val Ser
            165                 170                 175

Leu Arg Glu Val Val Glu Ile Ile Lys Ser Tyr Lys Val Ile Cys
        180                 185                 190

Leu Ser Lys Ser Leu Ser Ile Ile Ile Glu Gly Asp Asn Ile Trp Lys
            195                 200                 205

Thr Asp Lys Lys Trp Leu Thr Phe Ala Leu Ser Gln Val Leu Asp Asn
210                 215                 220

Ala Ile Lys Tyr Ser Asn Pro Glu Ser Lys Ile Ile Ser Ile Gly
225                 230                 235                 240

Glu Glu Ser Ile Arg Ile Gln Asp Tyr Gly Ile Gly Ile Leu Glu Glu
                245                 250                 255

Asp Ile Pro Arg Leu Phe Glu Asp Gly Phe Thr Gly Tyr Asn Gly His
                260                 265                 270

Glu His Gln Lys Ala Thr Gly Met Gly Leu Tyr Met Thr Lys Glu Val
            275                 280                 285

Leu Ser Ser Leu Asn Leu Ser Ile Ser Val Asp Ser Lys Ile Asn Tyr
    290                 295                 300

Gly Thr Ala Val Ser Ile His Lys
305                 310

<210> SEQ ID NO 110
<211> LENGTH: 345
<212> TYPE: PRT
<213> ORGANISM: Streptococcus agalactiae

<400> SEQUENCE: 110

Met Lys Leu Lys Tyr Tyr Ile Val Ile Gly Tyr Leu Ile Ser Met Leu
1               5                   10                  15

Ile Thr Val Ala Gly Val Phe Phe Gly Leu Asn His Met Leu Ile Glu
            20                  25                  30

Thr Arg Gly Val Tyr Tyr Ile Leu Ser Val Thr Ile Ile Ala Cys Ile
        35                  40                  45

Val Gly Gly Ile Val Asn Leu Phe Leu Leu Ser Ser Val Phe Thr Ser
    50                  55                  60

Leu Lys Lys Leu Lys Gln Lys Met Lys Asp Ile Ser Gln Arg Cys Phe
65                  70                  75                  80

Asp Thr Lys Ala Gln Ile Cys Ser Pro Gln Glu Phe Lys Asp Leu Glu
                85                  90                  95

Thr Ala Phe Asn Gln Met Ser Ser Glu Leu Glu Ser Thr Phe Lys Ser
            100                 105                 110

Leu Asn Glu Ser Glu Arg Glu Lys Thr Met Met Ile Ala Gln Leu Ser
        115                 120                 125

His Asp Ile Lys Thr Pro Ile Thr Ser Ile Gln Ser Thr Val Glu Gly
    130                 135                 140

Ile Leu Asp Gly Ile Ile Ser Glu Glu Glu Val Asn Tyr Tyr Leu Asn
145                 150                 155                 160

Thr Ile Ser Arg Gln Thr Asn Arg Leu Asn His Leu Val Glu Glu Leu
                165                 170                 175

Ser Phe Ile Thr Leu Glu Thr Met Ser Asp Thr Ala Glu Pro His Lys
            180                 185                 190

Glu Glu Thr Ile Tyr Leu Asp Lys Leu Leu Ile Asp Ile Leu Ser Glu
```

```
                195                 200                 205
Phe Gln Leu Val Phe Glu Lys Glu Asn Arg Gln Val Met Ile Asp Val
    210                 215                 220

Ala Pro Asp Val Ser Lys Leu Ser Ser Gln Tyr Asp Lys Leu Ser Arg
225                 230                 235                 240

Ile Leu Leu Asn Leu Ile Ser Asn Ala Val Lys Tyr Ser Asp Pro Gly
                245                 250                 255

Ser Pro Leu Thr Ile Lys Ala Tyr Ser Asn Arg Gln Asp Ile Val Ile
            260                 265                 270

Asp Ile Ile Asp Gln Gly Tyr Gly Ile Lys Asp Glu Asp Leu Ala Ser
        275                 280                 285

Ile Phe Asn Arg Leu Tyr Arg Val Glu Ser Ser Arg Asn Met Lys Thr
    290                 295                 300

Gly Gly His Gly Leu Gly Leu Tyr Ile Ala Arg Gln Leu Ala His Gln
305                 310                 315                 320

Leu Asn Gly Asp Ile Leu Val Glu Ser Gln Tyr Gln Lys Gly Ser Lys
                325                 330                 335

Phe Ser Leu Val Leu Lys Leu Gln Lys
                340                 345

<210> SEQ ID NO 111
<211> LENGTH: 356
<212> TYPE: PRT
<213> ORGANISM: Streptococcus agalactiae

<400> SEQUENCE: 111

Met Thr Lys Leu Arg Arg Phe Arg Phe Pro Leu Arg Phe Tyr Phe Thr
1               5                   10                  15

Leu Met Phe Val Leu Thr Met Leu Phe Ser Val Leu Ala Ser Leu Leu
                20                  25                  30

Leu Val Ala Ala Ile Val Phe Thr Phe Gln Gly Val Leu Thr Thr
            35                  40                  45

His Val Leu Gln Val Ser Ala Leu Ala Val Val Phe Leu Ser Leu Val
        50                  55                  60

Ile Ala Ser Ile Ser Met Trp Tyr Gly Ser Tyr His Leu Thr Lys Pro
65                  70                  75                  80

Ile Leu Asp Ile Ser Arg Ile Val Ser Asn Val Ala Asp Gly Asp Phe
                85                  90                  95

Glu Gly His Ile Tyr Arg Asn Ser Asn Arg Arg Lys Ser Tyr Glu Tyr
                100                 105                 110

Tyr Asn Glu Leu Asp Glu Leu Ser Glu Ser Ile Asn Gln Met Ile Val
            115                 120                 125

Ser Leu Ser His Met Asp His Met Arg Lys Asp Phe Ile Thr Asn Val
        130                 135                 140

Ser His Glu Leu Lys Thr Pro Ile Ala Ala Val Ala Asn Ile Val Glu
145                 150                 155                 160

Leu Leu Gln Asp Pro Glu Leu Asp Glu Glu Thr Gln Ser Glu Leu Leu
                165                 170                 175

Gly Leu Val Lys Thr Glu Ser Leu Arg Leu Thr Arg Leu Cys Asp Thr
            180                 185                 190

Met Leu Gln Met Ser Arg Val Asp Asn Gln Glu Thr Ile Gly Glu Leu
        195                 200                 205

Ser Ser Val Arg Val Asp Glu Gln Ile Arg Gln Ala Met Ile Ser Leu
210                 215                 220
```

```
Thr Glu Arg Trp Gln Ala Lys Arg Ile Asn Phe Gln Leu Asp Ser Lys
225                 230                 235                 240

Pro Tyr Thr Val Tyr Ser Asn Ser Asp Leu Leu Met Gln Val Trp Ile
            245                 250                 255

Asn Leu Leu Asp Asn Ala Ile Lys Tyr Ser Asp Asp Ile Val Asp Leu
                260                 265                 270

Arg Val Arg Met Glu Thr Asn Asn His Tyr Leu Arg Val Ile Ile
            275                 280                 285

Ser Asp Lys Gly Arg Gly Ile Ser Gln Tyr Asp Val Gln His Ile Phe
    290                 295                 300

Asp Lys Phe Tyr Gln Ala Asp Gln Ser His Asn Gln Gln Gly Asn Gly
305                 310                 315                 320

Leu Gly Leu Ala Ile Val Lys Arg Ile Ile Val Leu Cys Lys Gly Arg
                325                 330                 335

Ile Ser Val Ser Ser Gln Phe Glu Ile Gly Thr Glu Phe Cys Val Glu
                340                 345                 350

Leu Pro Leu Ser
        355

<210> SEQ ID NO 112
<211> LENGTH: 317
<212> TYPE: PRT
<213> ORGANISM: Streptococcus mutans

<400> SEQUENCE: 112

Met Ile Arg Ser Tyr Leu Arg Glu Tyr Ser Ile Trp Tyr Leu Asn Tyr
1               5                   10                  15

Ala Ile Val Ser Leu Ala Phe Leu Leu Thr Phe Tyr Leu Tyr His Leu
                20                  25                  30

Pro Leu Val Tyr Phe Ile Asn Ser Leu Ile Leu Ser Leu Thr Ile Leu
            35                  40                  45

Leu Ile Thr Ser Leu Ile Leu Tyr Trp Arg Phe His Gln Lys Leu Lys
    50                  55                  60

Asn Leu His His Phe Ile Tyr Val Lys Glu Pro Arg Asn Leu Thr Met
65                  70                  75                  80

Leu Thr Ala Pro Ser Asp Leu Val Tyr Lys Glu Ile Leu Lys Leu
                85                  90                  95

Leu Gln Glu Gln Ser Asp Ile Asn Leu Gln His Lys Thr Gln Glu Glu
            100                 105                 110

Gln Leu Gln Gln Leu Ile Lys Leu Trp Ser His Gln Met Lys Val Pro
        115                 120                 125

Ile Ser Ala Leu Ser Leu Met Ala Gln Thr Gly His Leu Asp Lys Glu
    130                 135                 140

Asp Val Gln Arg Gln Leu Leu Arg Leu Glu Asn Asp Leu Ser Arg Leu
145                 150                 155                 160

Leu Asn Tyr Leu Lys Phe Ser Gln Asn Gln Ser Asp Phe Arg Phe Glu
                165                 170                 175

Lys Cys Gln Ile Arg Asn Ile Leu Ile Asp Leu Ile Lys Lys Asn Gln
            180                 185                 190

Val Phe Phe Leu Gln Lys Asp Leu Ser Leu Thr Ile Asp Gly Asp Trp
        195                 200                 205

Glu Ile Lys Ser Asp Lys Lys Trp Leu Ser Phe Val Phe Ser Gln Ile
    210                 215                 220

Leu Asp Asn Ala Ile Lys Tyr Asn Lys Lys Gly Gly Gln Ile Thr Ile
225                 230                 235                 240
```

-continued

Lys Ile Lys Glu Asn Gln Ile Leu Ile Arg Asp Thr Gly Ile Gly Ile
                245                 250                 255

Leu Lys Glu Asp Ile Pro Arg Leu Phe Glu Glu Gly Phe Thr Gly Tyr
            260                 265                 270

Asn Gly His Glu His Gln Lys Ala Thr Gly Leu Gly Leu Tyr Met Ala
            275                 280                 285

Lys Lys Val Leu Asn Asn Leu Glu Leu Asp Ile Asn Ile Glu Ser Gln
290                 295                 300

Ile Asp Gln Gly Thr Gln Val Tyr Val Thr Lys Arg Arg
305                 310                 315

<210> SEQ ID NO 113
<211> LENGTH: 350
<212> TYPE: PRT
<213> ORGANISM: Streptococcus pneumoniae

<400> SEQUENCE: 113

Met Lys Leu Lys Ser Tyr Ile Leu Val Gly Tyr Ile Ile Ser Thr Leu
1               5                   10                  15

Leu Thr Ile Leu Val Val Phe Trp Ala Val Gln Lys Met Leu Ile Ala
            20                  25                  30

Lys Gly Glu Ile Tyr Phe Leu Leu Gly Met Thr Ile Val Ala Ser Leu
        35                  40                  45

Val Gly Ala Gly Ile Ser Leu Phe Leu Leu Pro Val Phe Thr Ser
    50                  55                  60

Leu Gly Lys Leu Lys Glu His Ala Lys Arg Val Ala Ala Lys Asp Phe
65                  70                  75                  80

Pro Ser Asn Leu Glu Val Gln Gly Pro Val Glu Phe Gln Gln Leu Gly
                85                  90                  95

Gln Thr Phe Asn Glu Met Ser His Asp Leu Gln Val Ser Phe Asp Ser
            100                 105                 110

Leu Glu Glu Ser Glu Arg Glu Lys Gly Leu Met Ile Ala Gln Leu Ser
        115                 120                 125

His Asp Ile Lys Thr Pro Ile Thr Ser Ile Gln Ala Thr Val Glu Gly
    130                 135                 140

Ile Leu Asp Gly Ile Ile Lys Glu Ser Glu Gln Ala His Tyr Leu Ala
145                 150                 155                 160

Thr Ile Gly Arg Gln Thr Glu Arg Leu Asn Lys Leu Val Glu Glu Leu
                165                 170                 175

Asn Phe Leu Thr Leu Asn Thr Ala Arg Asn Gln Val Glu Thr Thr Ser
            180                 185                 190

Lys Asp Ser Ile Phe Leu Asp Lys Leu Leu Ile Glu Cys Met Ser Glu
        195                 200                 205

Phe Gln Phe Leu Ile Glu Gln Glu Arg Arg Asp Val His Leu Gln Val
    210                 215                 220

Ile Pro Glu Ser Ala Arg Ile Glu Gly Asp Tyr Ala Lys Leu Ser Arg
225                 230                 235                 240

Ile Leu Val Asn Leu Val Asp Asn Ala Phe Lys Tyr Ser Ala Pro Gly
                245                 250                 255

Thr Lys Leu Glu Val Val Ala Lys Leu Glu Lys Asp Gln Leu Ser Ile
            260                 265                 270

Ser Val Thr Asp Glu Gly Gln Gly Ile Ala Pro Glu Asp Leu Glu Asn
        275                 280                 285

Ile Phe Lys Arg Leu Tyr Arg Val Glu Thr Ser Arg Asn Met Lys Thr

```
                   290                 295                 300
Gly Gly His Gly Leu Gly Leu Ala Ile Ala Arg Glu Leu Ala His Gln
305                 310                 315                 320

Leu Gly Gly Glu Ile Thr Val Ser Ser Gln Tyr Gly Leu Gly Ser Thr
                325                 330                 335

Phe Thr Leu Val Leu Asn Leu Ser Gly Ser Glu Asn Lys Ala
                340                 345                 350

<210> SEQ ID NO 114
<211> LENGTH: 324
<212> TYPE: PRT
<213> ORGANISM: Streptococcus pneumoniae

<400> SEQUENCE: 114

Met Leu Asp Trp Lys Gln Phe Phe Leu Ala Tyr Leu Arg Ser Arg Ser
  1               5                  10                  15

Arg Leu Phe Ile Tyr Leu Leu Ser Leu Ala Phe Leu Val Leu Leu Phe
                 20                  25                  30

Gln Phe Leu Phe Ala Ser Leu Gly Ile Tyr Phe Leu Tyr Phe Phe Phe
             35                  40                  45

Leu Cys Cys Phe Val Thr Ile Leu Phe Phe Thr Trp Asp Ile Leu Val
 50                  55                  60

Glu Thr Gln Val Tyr Arg Gln Glu Leu Leu Tyr Gly Glu Arg Glu Ala
 65                  70                  75                  80

Lys Ser Pro Leu Glu Ile Ala Leu Ala Glu Lys Leu Glu Ala Arg Glu
                 85                  90                  95

Met Glu Leu Tyr Gln Gln Arg Ser Lys Ala Glu Arg Lys Leu Thr Asp
            100                 105                 110

Leu Leu Asp Tyr Tyr Thr Leu Trp Val His Gln Ile Lys Thr Pro Ile
            115                 120                 125

Ala Ala Ser Gln Leu Leu Val Ala Glu Val Val Asp Arg Gln Leu Lys
130                 135                 140

Gln Gln Leu Glu Gln Glu Ile Phe Lys Ile Asp Ser Tyr Thr Asn Leu
145                 150                 155                 160

Val Leu Gln Tyr Leu Arg Leu Glu Ser Phe His Asp Asp Leu Val Leu
                165                 170                 175

Lys Gln Val Gln Ile Glu Asp Leu Val Lys Glu Ile Ile Arg Lys Tyr
            180                 185                 190

Ala Leu Phe Phe Ile Gln Lys Gly Leu Asn Val Asn Leu His Asp Leu
            195                 200                 205

Asp Lys Glu Ile Val Thr Asp Lys Lys Trp Leu Leu Val Val Ile Glu
210                 215                 220

Gln Ile Ile Ser Asn Ser Leu Lys Tyr Thr Lys Glu Gly Gly Leu Glu
225                 230                 235                 240

Ile Tyr Met Asp Asp Gln Glu Leu Cys Ile Lys Asp Thr Gly Ile Gly
                245                 250                 255

Ile Lys Asn Ser Asp Val Leu Arg Val Phe Glu Arg Gly Phe Ser Gly
            260                 265                 270

Tyr Asn Gly Arg Leu Thr Gln Gln Ser Ser Gly Leu Gly Leu Tyr Leu
            275                 280                 285

Ser Lys Lys Ile Ser Glu Glu Leu Gly His Gln Ile Arg Ile Glu Ser
            290                 295                 300

Glu Val Gly Lys Gly Thr Thr Val Arg Ile Gln Phe Ala Gln Val Asn
305                 310                 315                 320
```

Leu Val Leu Glu

<210> SEQ ID NO 115
<211> LENGTH: 358
<212> TYPE: PRT
<213> ORGANISM: Bifidobacterium longum

<400> SEQUENCE: 115

Met Met Ala Ser Lys Lys Gln Gln Gln Ser Arg Leu Asp Ala Met Lys
1               5                   10                  15

Pro Arg Val Lys Pro Val Asp Leu Phe Ser Ser Leu Lys Leu Glu Leu
            20                  25                  30

Ser Ala Leu Ile Val Ile Ala Thr Ala Ile Ala Phe Ala Met Cys Trp
        35                  40                  45

Phe Leu Leu Lys Phe Gly Trp Ser Gly Trp Ile Ala Met Pro Leu Thr
    50                  55                  60

Leu Val Val Ala Leu Gly Ile Thr Tyr Phe Phe Ser Arg Gly Ile Thr
65                  70                  75                  80

Ala Pro Leu Arg Gln Met Arg Asp Val Ala Glu Ala Met Ala Asp Gly
                85                  90                  95

Asp Tyr Thr Val Arg Val Asp Ile Asp Gln Asp Arg His Asp Glu Val
            100                 105                 110

Gly Lys Leu Ala Arg Ser Phe Asn Glu Met Ala Gly Glu Leu Glu His
        115                 120                 125

Ala Asp Lys Met Arg Arg Asp Met Ile Ala Asn Val Ser His Glu Leu
    130                 135                 140

Arg Thr Pro Val Ser Ala Leu Gln Ala Met Val Glu Asn Met Ala Asp
145                 150                 155                 160

Gly Val Thr Glu Pro Thr Pro Thr Asn Leu Glu Ser Ile Leu Thr Gln
                165                 170                 175

Thr Gln Arg Leu Ser Asp Leu Ile Ala Phe Leu Leu Asp Leu Ser Arg
            180                 185                 190

Met Glu Ala Gly Ala Ala Ser Leu Asn Ile Glu Lys Phe Asn Phe Ala
        195                 200                 205

Asp Phe Leu Asp Glu Thr Ile Glu Pro Leu Glu Ile Ala Asp Gly Gly
    210                 215                 220

His Ala His Asp Ile Arg Val Thr Val Pro Ala Asp Ile Thr Met Glu
225                 230                 235                 240

Gly Asp Gln Asp Arg Leu Arg Gln Leu Phe Thr Asn Ile Ile Ala Asn
                245                 250                 255

Ala Leu Lys His Ser Ala Asp Gly Thr Thr Val Leu Val Asp Ala His
            260                 265                 270

Glu Asp Glu Asn Gln Gly Thr Ile Val Thr Asn Val Val Asn Phe Gly
        275                 280                 285

Ser Gln Ile Ala Pro Ser Asp Arg Leu Asp Ile Phe Arg Arg Phe Val
    290                 295                 300

Lys Gly Lys Thr Gly Pro Gly Thr Glu Ser Gly Gly Thr Gly Leu Gly
305                 310                 315                 320

Leu Ser Ile Ala Arg Trp Ala Ala Gln Leu His Gly Gly Thr Val Lys
                325                 330                 335

Val Val Asp Asp Thr Arg Gly Ala Asp Phe Glu Ile Ile Leu Pro Lys
            340                 345                 350

Tyr His Ile Ala Glu Arg
        355

<210> SEQ ID NO 116
<211> LENGTH: 368
<212> TYPE: PRT
<213> ORGANISM: Streptococcus avermitilis

<400> SEQUENCE: 116

Met Ser Asp Gly Pro Ala Ala Arg Arg Gly Pro Gly Asp Pro Trp Gly
 1               5                  10                  15

Gly Val Arg Pro Phe Ser Ile Lys Thr Lys Leu Gly Ala Leu Val Val
                20                  25                  30

Ile Ser Val Leu Ile Thr Thr Gly Leu Ser Met Ile Ala Val His Thr
            35                  40                  45

Lys Thr Glu Leu Arg Phe Ile Thr Val Phe Ser Met Ile Ala Thr Leu
        50                  55                  60

Leu Ile Thr Gln Phe Val Ala His Ser Leu Thr Ala Pro Leu Asp Asp
 65                  70                  75                  80

Met Asn Thr Val Ala Arg Ser Ile Ser Arg Gly Asp Tyr Thr Arg Arg
                 85                  90                  95

Val Arg Glu Asn Arg Trp Asp Glu Leu Gly Asp Leu Ala His Thr Ile
            100                 105                 110

Asn Leu Met Ala Asp Glu Leu Glu Ala Gln Asp Arg Gln Arg Lys Glu
        115                 120                 125

Leu Val Ala Asn Val Ser His Glu Leu Arg Thr Pro Ile Ala Gly Leu
130                 135                 140

Arg Ala Val Leu Glu Asn Ile Val Asp Gly Ile Ser Ala Ala Asp Pro
145                 150                 155                 160

Glu Thr Met Arg Thr Ala Leu Lys Gln Thr Glu Arg Leu Gly Arg Leu
                165                 170                 175

Val Glu Thr Leu Leu Asp Leu Ser Arg Leu Asp Asn Gly Val Val Pro
            180                 185                 190

Leu Arg Lys Arg Arg Phe Glu Val Trp Pro Tyr Leu Ser Gly Val Leu
        195                 200                 205

Lys Glu Ala Asn Met Val Ala Ser Ala Arg Ala Ser Leu Ala Thr Gly
    210                 215                 220

Ser Gly Ser His Thr Arg Thr Asp Val His Leu His Leu Asp Val Ser
225                 230                 235                 240

Pro Pro Glu Leu Thr Ala His Ala Asp Pro Glu Arg Ile His Gln Val
                245                 250                 255

Val Ala Asn Leu Ile Asp Asn Ala Val Lys His Ser Pro Pro His Gly
            260                 265                 270

Arg Val Thr Val Lys Ala Arg Arg Gly Pro Ala Pro Glu Ser Leu Asp
        275                 280                 285

Leu Glu Val Leu Asp Glu Gly Pro Gly Ile Pro Glu Ser Glu Trp His
    290                 295                 300

Arg Val Phe Glu Arg Phe Asn Arg Gly Ala Val Ser Ala Pro His Gly
305                 310                 315                 320

Pro Gly Ser Asp Gly Gly Thr Gly Leu Gly Leu Ala Ile Ala Arg Trp
                325                 330                 335

Ala Val Asp Leu His Gly Gly Arg Ile Gly Val Ala Glu Ser Gln Arg
            340                 345                 350

Gly Cys Arg Ile Gln Val Thr Leu Pro Gly Leu Pro Ser Leu Pro Ser
        355                 360                 365

<210> SEQ ID NO 117

<211> LENGTH: 385
<212> TYPE: PRT
<213> ORGANISM: Streptococcus avermitilis

<400> SEQUENCE: 117

```
Met Gly Val Met Thr Asp Gly Arg Gly Arg Arg Ala Glu Arg Leu
 1               5                  10                  15

Val Gly Ala Ala Ala Trp Pro Arg Ser Gly Lys Glu Gly Thr Pro Arg
                20                  25                  30

Glu His Arg Gly Thr Pro Thr Gly Gly Asp Gly Lys Arg Ser Val Ser
                35                  40                  45

Leu Phe Arg Arg Ile Phe Leu Leu Asn Ala Val Gly Leu Thr Val Ala
        50                  55                  60

Thr Ala Leu Leu Leu Gly Pro Val Thr Val Ser Thr Pro Val Leu Pro
 65                  70                  75                  80

Gly Glu Ala Leu Val Val Leu Ala Gly Leu Ala Val Met Leu Val Val
                85                  90                  95

Asn Ala Val Val Leu Trp Ile Gly Leu Ala Pro Leu Gln Arg Leu Gly
                100                 105                 110

Arg Ala Met Ala Thr Ala Asp Leu Leu His Pro Gly Ala Arg Ala Val
            115                 120                 125

Val Thr Gly Pro Ala Glu Met Ala Asp Leu Ile Ser Thr Tyr Asn Thr
130                 135                 140

Met Leu Asp Arg Leu Glu Thr Glu Arg Ala Thr Ser Ala Ala Arg Ala
145                 150                 155                 160

Leu Ser Ala Gln Glu Arg Glu Arg His Arg Val Ser Gln Glu Leu His
                165                 170                 175

Asp Glu Val Gly Gln Thr Leu Thr Ala Val Leu Leu Gln Leu Arg Arg
            180                 185                 190

Val Ala Asp Arg Ala Pro Glu Gly Leu Arg Ala Glu Val Arg Gln Ala
        195                 200                 205

Gln Glu Ala Thr Arg Gly Ser Leu Asp Glu Ile Arg Arg Ile Ala Arg
    210                 215                 220

Arg Leu Arg Pro Gly Val Leu Glu Glu Leu Gly Leu Leu Ser Ala Leu
225                 230                 235                 240

Arg Ala Leu Thr Thr Glu Phe Thr Ala His Gly Leu Ser Val Arg His
                245                 250                 255

His Phe Asp Gly Glu Leu Pro Gln Leu Ser Glu Glu Thr Glu Leu Val
            260                 265                 270

Val Tyr Arg Val Ala Gln Glu Gly Leu Thr Asn Thr Ala Arg His Ala
        275                 280                 285

Gly Ala Asp Arg Ala Glu Leu Arg Leu His Arg Val Ala Asp Gly Val
    290                 295                 300

Glu Leu Leu Val Arg Asp Asn Gly Thr Gly Ala Gly Arg Ala Pro Glu
305                 310                 315                 320

Gly Ala Gly Ile Arg Gly Met Arg Glu Arg Ala Leu Leu Ile Gly Ala
                325                 330                 335

Gly Leu Ala Val Glu Pro Gly Pro Asp Arg Gly Thr Asp Ile Arg Leu
            340                 345                 350

Arg Ile Thr Ser Thr Thr Ser Thr Ser Thr Ser Thr Ser Val Met Asn
        355                 360                 365

Ala Thr Ser Thr Gly Asp Arg Ser Gly Pro Arg Thr Gly Thr Pro Pro
    370                 375                 380

His
```

385

<210> SEQ ID NO 118
<211> LENGTH: 375
<212> TYPE: PRT
<213> ORGANISM: Streptococcus coelicolor

<400> SEQUENCE: 118

| | | | | | | | | | | | | | | |
|---|---|---|---|---|---|---|---|---|---|---|---|---|---|---|
| Met | Ser | Ser | Arg | Gly | Arg | Glu | Ala | Ala | Arg | Arg | Asn | Pro | Gly | Pro | Arg |
| 1 | | | | 5 | | | | | 10 | | | | | 15 | |
| Thr | Thr | Gly | Glu | Pro | Trp | Gly | Gly | Val | Arg | Pro | Phe | Ser | Ile | Lys | Thr |
| | | | 20 | | | | | 25 | | | | | 30 | | |
| Lys | Leu | Gly | Ala | Leu | Val | Val | Thr | Ser | Val | Leu | Ile | Thr | Thr | Gly | Leu |
| | | | 35 | | | | 40 | | | | | 45 | | | |
| Ser | Val | Ile | Ala | Val | His | Thr | Lys | Thr | Glu | Leu | Arg | Phe | Ile | Thr | Val |
| | 50 | | | | | 55 | | | | | 60 | | | | |
| Phe | Ser | Met | Ile | Ala | Thr | Leu | Leu | Ile | Thr | Gln | Phe | Val | Ala | His | Ser |
| 65 | | | | | 70 | | | | | 75 | | | | | 80 |
| Leu | Thr | Ala | Pro | Leu | Asp | Glu | Met | Asn | Ala | Val | Ala | Arg | Ser | Ile | Ser |
| | | | | 85 | | | | | 90 | | | | | 95 | |
| His | Gly | Asp | Tyr | Thr | Arg | Arg | Val | Arg | Glu | Asn | Arg | Arg | Asp | Glu | Leu |
| | | | | 100 | | | | | 105 | | | | | 110 | |
| Gly | Asp | Leu | Ala | Val | Thr | Ile | Asn | Arg | Met | Ala | Asp | Asp | Leu | Glu | Ala |
| | | | 115 | | | | | 120 | | | | | 125 | | |
| Gln | Asp | Leu | Gln | Arg | Lys | Glu | Leu | Val | Ala | Asn | Val | Ser | His | Glu | Leu |
| | 130 | | | | | 135 | | | | | 140 | | | | |
| Arg | Thr | Pro | Ile | Ala | Gly | Leu | Arg | Ala | Val | Leu | Glu | Asn | Ile | Val | Asp |
| 145 | | | | | 150 | | | | | 155 | | | | | 160 |
| Gly | Val | Thr | Glu | Ala | Asp | Pro | Glu | Thr | Met | Arg | Thr | Ala | Leu | Gly | Gln |
| | | | | 165 | | | | | 170 | | | | | 175 | |
| Thr | Glu | Arg | Leu | Gly | Arg | Leu | Val | Glu | Thr | Leu | Leu | Asp | Leu | Ser | Arg |
| | | | | 180 | | | | | 185 | | | | | 190 | |
| Leu | Asp | Asn | Gly | Val | Ile | Pro | Leu | Arg | Lys | Arg | Arg | Phe | Glu | Val | Trp |
| | | | 195 | | | | | 200 | | | | | 205 | | |
| Pro | Tyr | Leu | Ser | Gly | Val | Leu | Lys | Glu | Ala | Asn | Met | Val | Ala | Ser | Ala |
| | 210 | | | | | 215 | | | | | 220 | | | | |
| Arg | Ala | Gly | Ile | Ala | Ser | Gly | Ser | Gly | Ser | His | Ser | Arg | Thr | Asp | Val |
| 225 | | | | | 230 | | | | | 235 | | | | | 240 |
| His | Leu | Ala | Leu | Asp | Val | Phe | Pro | Pro | Glu | Leu | Thr | Ala | His | Ala | Asp |
| | | | | 245 | | | | | 250 | | | | | 255 | |
| Pro | Glu | Arg | Ile | His | Gln | Val | Val | Ala | Asn | Leu | Ile | Asp | Asn | Ala | Val |
| | | | | 260 | | | | | 265 | | | | | 270 | |
| Lys | His | Ser | Pro | Pro | His | Gly | Arg | Val | Thr | Val | Arg | Ala | Arg | Arg | Gly |
| | | | 275 | | | | | 280 | | | | | 285 | | |
| Glu | Leu | Pro | Glu | Ser | Leu | Glu | Leu | Glu | Val | Leu | Asp | Glu | Gly | Pro | Gly |
| | 290 | | | | | 295 | | | | | 300 | | | | |
| Ile | Pro | Arg | Ser | Glu | Trp | Arg | Arg | Val | Phe | Glu | Arg | Phe | Asn | Arg | Gly |
| 305 | | | | | 310 | | | | | 315 | | | | | 320 |
| Ser | Val | Ser | Arg | Pro | His | Gly | Pro | Gly | Ser | Asp | Gly | Thr | Gly | Leu |
| | | | | 325 | | | | | 330 | | | | | 335 | |
| Gly | Leu | Ala | Ile | Ala | Arg | Trp | Ala | Val | Asp | Leu | His | Gly | Gly | Arg | Ile |
| | | | 340 | | | | | 345 | | | | | 350 | | |
| Gly | Val | Ala | Glu | Ser | Glu | Arg | Gly | Cys | Arg | Ile | Leu | Ile | Thr | Leu | Pro |
| | | | 355 | | | | | 360 | | | | | 365 | | |

```
Gly Leu Pro Ser Thr Ser Gly
    370             375

<210> SEQ ID NO 119
<211> LENGTH: 331
<212> TYPE: PRT
<213> ORGANISM: Streptococcus coelicolor

<400> SEQUENCE: 119

Met Ala Arg Val Pro Asp Ala Ala Val Pro Leu Phe Trp Arg Ile
 1               5                  10                  15

Ser Leu Phe Asn Ser Val Val Leu Ile Ala Ala Thr Ala Leu Leu Leu
                20                  25                  30

Gly Pro Val Thr Val Ser Thr Pro Val Leu Leu Thr Glu Ala Ala Ile
            35                  40                  45

Leu Thr Ala Gly Leu Val Val Ile Leu Ile Ala Asn Ile Leu Leu Leu
        50                  55                  60

Arg Ile Gly Phe Gly Pro Leu Arg Gln Leu Ala Arg Ala Met Thr Thr
 65                 70                  75                  80

Thr Asp Leu Leu Arg Pro Arg Val Arg Pro Lys Val Asp Gly Asp Gly
                85                  90                  95

Glu Ile Ala Glu Leu Ile Thr Thr Phe Asn Thr Met Leu Asp Arg Leu
            100                 105                 110

Glu Ala Glu Arg Ala Leu Ser Ala Ala Arg Thr Leu Ser Ala Gln Glu
        115                 120                 125

Ser Glu Arg His Arg Val Ala Gln Glu Leu Tyr Asp Glu Val Gly Gln
    130                 135                 140

Thr Leu Ala Ala Val Leu Leu Asp Leu Lys Arg Val Ala Asp Gln Ala
145                 150                 155                 160

Pro Glu Glu Val Arg Glu Gln Leu Ser Gln Val Gln Glu Thr Thr Arg
                165                 170                 175

Ala Ser Leu Asp Glu Ile Arg Arg Ile Ala Arg Arg Leu Leu Pro Gly
            180                 185                 190

Val Leu Glu Glu Leu Gly Leu Ser Ser Ala Leu Arg Ser Leu Ser Asp
        195                 200                 205

Glu Phe Thr Gly Pro Ser Leu Thr Val Arg His Asp Ile Ala Thr Gly
    210                 215                 220

Leu Pro Gly Leu Gly Asp Asn Ala Asp Leu Val Leu Tyr Arg Val Ala
225                 230                 235                 240

Gln Glu Gly Leu Thr Asn Ala Ala Arg His Ser Gly Ala Arg Leu Val
                245                 250                 255

Val Leu Ser Leu Glu Arg Ala Gly Asp Ala Val Arg Leu Arg Val Arg
            260                 265                 270

Asp Asp Gly Arg Gly Phe Asp Asp Ser Gly Gly Ala Val Glu Gly Ala
        275                 280                 285

Gly Ile Arg Gly Met Arg Glu Arg Ala Leu Leu Ile Gly Ala Asp Leu
    290                 295                 300

Val Val Gly Pro Ala Arg Gly Gly Thr Glu Val Arg Leu Thr Val
305                 310                 315                 320

Pro Val Gly Asp Arg Val Pro Asp Arg Val Ala
                325                 330

<210> SEQ ID NO 120
<211> LENGTH: 358
<212> TYPE: PRT
<213> ORGANISM: Streptococcus coelicolor
```

-continued

```
<400> SEQUENCE: 120

Met Gly Val Val Thr Asp Ile Arg Ser Arg Ser Arg Ser Ala Lys Leu
  1               5                  10                  15

Ala Ala Gly Val Ser Cys Glu Lys Ala Gly Arg Ser Gly Lys Arg Asn
             20                  25                  30

Val Ser Leu Phe Trp Arg Ile Phe Ser Leu Asn Ala Ala Gly Leu Val
         35                  40                  45

Val Ala Thr Ala Leu Leu Gly Pro Val Thr Val Ser Thr Pro Val
     50                  55                  60

Leu Ala Gly Glu Ala Leu Val Leu Ala Gly Leu Ala Ala Leu Leu
 65                  70                  75                  80

Ala Gly Asn Ala Val Leu Arg Ile Gly Leu Thr Pro Leu His Arg
             85                  90                  95

Leu Gly Arg Ala Met Ser Thr Ala Asp Leu Leu Val Pro Gly Thr Arg
             100                 105                 110

Pro Glu Val Ser Gly Pro Ala Glu Ala Ala Gln Leu Ile Ala Thr Tyr
             115                 120                 125

Asn Thr Met Leu Asp Arg Leu Gln Ala Glu Arg Ala Gly Ala Gly
130                 135                 140

Arg Ala Leu Gln Ala Gln Glu Arg Glu Arg His Arg Ile Ala Arg Glu
145                 150                 155                 160

Leu His Asp Glu Val Gly Gln Thr Leu Thr Ala Val Leu Leu Gln Leu
             165                 170                 175

Lys Arg Val Ala Asp Arg Val Pro Gly Glu Leu Arg Asp Glu Val Thr
             180                 185                 190

Leu Ala Gln Glu Ala Thr Arg Ala Gly Leu Asp Glu Ile Arg Arg Ile
             195                 200                 205

Ala Arg Arg Leu Arg Pro Gly Val Leu Glu Glu Leu Gly Leu Ala Ser
210                 215                 220

Ala Leu Arg Ser Leu Ala Ala Glu Phe Thr His His Gly Leu Thr Val
225                 230                 235                 240

Gln His His Ile Pro Gly Asp Leu Pro Pro Leu Ala Pro Glu Ala Glu
             245                 250                 255

Leu Val Leu Tyr Arg Val Ala Gln Glu Gly Leu Thr Asn Thr Ala Arg
             260                 265                 270

His Ala Asp Ala Ala Arg Ala Ala Leu Thr Leu His Pro Leu Pro Gly
             275                 280                 285

Asp Ala Gly Val Glu Leu Leu Val Arg Asp Asp Gly Thr Gly Leu Gly
290                 295                 300

Thr Ala Ala Glu Gly Ala Gly Ile Arg Gly Met Arg Glu Arg Ala Leu
305                 310                 315                 320

Leu Ile Gly Ala Glu Ile His Phe Glu Pro Ala Pro Gly Gly Gly Thr
             325                 330                 335

Asp Val Arg Leu Arg Val Pro Ala Pro Pro Gly Asp Arg Cys Ala Asp
             340                 345                 350

Arg Thr Gly Asp Ser Pro
            355

<210> SEQ ID NO 121
<211> LENGTH: 370
<212> TYPE: PRT
<213> ORGANISM: Streptococcus coelicolor

<400> SEQUENCE: 121
```

```
Met His Ala Thr Phe Leu Ile Ala Leu Tyr Ala Phe Ala Gly Ala Ala
 1               5                  10                  15

Ala Ala Gly Leu Val Gly Ala Ala Val Leu Arg Leu Ile Arg Arg Arg
             20                  25                  30

Ser Leu Thr Ala Ser Leu Ala Val Val Ala Ala Val Ala Val Leu Ala
             35                  40                  45

Met Leu Ala Gly Thr Leu Ala Val Ala Trp Ala Met Phe Leu Ser Pro
 50                  55                  60

His Asp Leu Ser Val Val Thr Thr Val Ala Met Ala Ala Val Val
 65                  70                  75                  80

Ser Leu Ala Thr Ala Leu Leu Leu Gly Arg Trp Val Val Ala Arg Ser
             85                  90                  95

Arg Glu Leu Ala Ala Ala Arg Ser Phe Gly Asp Asp Gly Asp Tyr
             100                 105                 110

Ala Ala Pro Ser Thr Pro Ala Thr Ala Glu Leu Asp Ala Leu Ser Arg
             115                 120                 125

Glu Leu Ala Ala Thr Ser Ala Arg Leu Ala Glu Ser Arg Glu Arg Glu
 130                 135                 140

Arg Ala Leu Glu Ala Ser Arg Arg Glu Leu Val Ala Trp Ile Ser His
145                 150                 155                 160

Asp Leu Arg Thr Pro Leu Ala Gly Leu Arg Ala Met Ser Glu Ala Leu
             165                 170                 175

Glu Asp Gly Val Ala Ala Asp Pro Asp Arg Tyr Leu Arg Gln Ile Arg
             180                 185                 190

Ala Glu Val Glu Arg Leu Asn Asp Met Val Gly Asp Leu Phe Glu Leu
             195                 200                 205

Ser Arg Ile His Ala Gly Thr Leu Val Leu Ala Pro Ala Arg Ile Ser
             210                 215                 220

Leu Tyr Asp Leu Ile Gly Asp Ala Leu Ala Gly Ala Asp Pro Leu Ala
225                 230                 235                 240

Arg Arg His Gly Val Arg Leu Val Gly Asp Ala Val Ala Ala Val Pro
             245                 250                 255

Val Glu Val Asp Gly Lys Glu Met Ser Arg Val Leu Gly Asn Leu Leu
             260                 265                 270

Val Asn Ala Ile Arg Arg Thr Pro Ala Asp Gly Thr Val Ala Val Ala
             275                 280                 285

Ala Glu Arg Ser Ala Asp Gly Val Val Ser Val Thr Asp Gly Cys
             290                 295                 300

Gly Gly Ile Pro Glu Glu Asp Leu Pro Arg Val Phe Asp Thr Gly Trp
305                 310                 315                 320

Arg Gly Thr His Ala Arg Thr Pro Pro Ala Gly Ala Gly Leu Gly Leu
             325                 330                 335

Ala Ile Val Arg Gly Ile Val Glu Ala His Arg Gly Arg Ala Thr Val
             340                 345                 350

Arg Asn Ile Pro Gly Gly Cys Arg Phe Glu Val Ile Leu Pro Pro Ala
             355                 360                 365

Gly Ala
 370
```

<210> SEQ ID NO 122
<211> LENGTH: 344
<212> TYPE: PRT
<213> ORGANISM: Nostoc sp.

<400> SEQUENCE: 122

| | | | | | | | | | | | | | | |
|---|---|---|---|---|---|---|---|---|---|---|---|---|---|---|
| Met | Ile | Ser | Met | Glu | Phe | Ser | Thr | Pro | Thr | Glu | Tyr | Val | Phe | Gly | Tyr |
| 1 | | | | 5 | | | | | 10 | | | | | 15 | |

Leu Tyr Thr Gly Pro Ile Leu Leu Ala Asn His Trp Phe Gly Arg Ile
            20                25                30

Ala Thr Leu Leu Thr Thr Phe Ile Ala Val Phe Leu Thr Ile Leu Asn
       35               40              45

Leu Gly Phe Pro Asn Asn Glu Val Ile Arg Phe Pro Thr Val Ala Ser
   50               55              60

Arg Met Ile Ala Cys Met Ser Leu Ile Val Thr Gly Ile Leu Ser Asp
65                70              75              80

Arg Leu Arg Arg Ser Gln Glu Ala Ile Ala Leu Thr Arg Ala Lys Leu
           85               90              95

Glu Ser Gln Glu Glu Leu Val Arg Leu Arg Glu Asp Phe Ala Ser Thr
       100              105            110

Leu Thr His Asp Leu Lys Thr Pro Leu Leu Gly Ala Ile Glu Thr Leu
      115              120            125

Lys Ala Val Gln Gln Glu Lys Phe Gly Ala Val Ser Ser Ala Gln Gln
130                135              140

Pro Val Leu Ala Thr Ile Ile Arg Ser His Gln Thr Ser Leu Gln Leu
145              150              155              160

Leu Glu Thr Leu Leu Asp Ile Tyr Arg Asn Asp Thr Glu Gly Leu Gln
           165             170            175

Leu Asn Leu Ile Pro Val Asp Leu Thr Thr Leu Ala Glu Glu Ala Ala
      180              185            190

Ser Thr Leu Ile Asp Leu Ala Ala Ser Arg Arg Val His Ile Ser Phe
      195              200            205

Asn Tyr Gly Asp Ser Asp Trp Arg Arg Ser Leu Trp Val Asn Gly Asp
   210               215              220

Pro Leu Gln Leu Gln Arg Val Leu Tyr Asn Leu Leu Val Asn Ala Ile
225                230              235              240

Asn His Ser Arg Arg Gly Asp Arg Val Glu Val Val Leu Glu Thr Gln
           245             250            255

Ala Ser Tyr Gln Val Val Lys Ile Ser Asp Thr Gly Ala Gly Ile Gln
      260              265            270

Ala Glu Gln Phe Pro His Leu Phe Glu Arg Phe Tyr Gln Gly His Ser
      275              280            285

Glu Arg Gln Ala Lys Gly Ser Gly Leu Gly Leu Tyr Leu Ser Arg Gln
   290               295              300

Ile Ile Ala Ala His Asn Gly Ile Ile Trp Ala Glu Asn Arg Val Pro
305                310              315              320

Thr Gly Ala Met Phe Ala Phe Lys Leu Pro Phe Leu Pro Phe Gln Pro
           325               330              335

Ser Leu Ser Ala Ser Asp Gly Phe
      340

<210> SEQ ID NO 123
<211> LENGTH: 325
<212> TYPE: PRT
<213> ORGANISM: Haemophilus influenzae

<400> SEQUENCE: 123

Met Lys Asn Phe Lys Tyr Phe Ala Gln Ser Tyr Val Asp Trp Val Ile
1                5              10              15

-continued

```
Arg Leu Gly Arg Leu Arg Phe Ser Leu Leu Gly Val Met Ile Leu Ala
            20                  25                  30

Val Leu Ala Leu Cys Thr Gln Ile Leu Phe Ser Leu Phe Ile Val His
        35                  40                  45

Gln Ile Ser Trp Val Asp Ile Phe Arg Ser Val Thr Phe Gly Leu Leu
    50                  55                  60

Thr Ala Pro Phe Val Ile Tyr Phe Phe Thr Leu Leu Val Glu Lys Leu
65                  70                  75                  80

Glu His Ser Arg Leu Asp Leu Ser Ser Ser Val Asn Arg Leu Glu Asn
                85                  90                  95

Glu Val Ala Glu Arg Ile Ala Ala Gln Lys Lys Leu Ser Gln Ala Leu
            100                 105                 110

Glu Lys Leu Glu Lys Asn Ser Arg Asp Lys Ser Thr Leu Leu Ala Thr
        115                 120                 125

Ile Ser His Glu Phe Arg Thr Pro Leu Asn Gly Ile Val Gly Leu Ser
    130                 135                 140

Gln Ile Leu Leu Asp Asp Glu Leu Asp Asp Leu Gln Arg Asn Tyr Leu
145                 150                 155                 160

Lys Thr Ile Asn Ile Ser Ala Val Ser Leu Gly Tyr Ile Phe Ser Asp
                165                 170                 175

Ile Ile Asp Leu Glu Lys Ile Asp Ala Ser Arg Ile Glu Leu Asn Arg
            180                 185                 190

Gln Pro Thr Asp Phe Pro Ala Leu Leu Asn Asp Ile Tyr Asn Phe Ala
        195                 200                 205

Ser Phe Leu Ala Lys Glu Lys Asn Leu Ile Phe Ser Leu Glu Leu Glu
    210                 215                 220

Pro Asn Leu Pro Asn Trp Leu Asn Leu Asp Arg Val Arg Leu Ser Gln
225                 230                 235                 240

Ile Leu Trp Asn Leu Ile Ser Asn Ala Val Lys Phe Thr Asp Gln Gly
                245                 250                 255

Asn Ile Ile Leu Lys Ile Met Arg Asn Gln Asp Cys Tyr His Phe Ile
            260                 265                 270

Val Lys Asp Thr Gly Met Gly Ile Ser Pro Glu Glu Gln Lys His Ile
        275                 280                 285

Phe Glu Met Tyr Tyr Gln Val Lys Glu Ser Arg Gln Gln Ser Ala Gly
    290                 295                 300

Ser Gly Ile Gly Leu Ala Ile Ser Lys Asn Leu Ala Gln Leu Met Gly
305                 310                 315                 320

Arg Gly Phe Asn Ser
                325
```

<210> SEQ ID NO 124
<211> LENGTH: 365
<212> TYPE: PRT
<213> ORGANISM: Ralstonia solanacearum

<400> SEQUENCE: 124

```
Met Lys Leu Pro Val Gly Arg Leu Phe Trp Lys Cys Phe Ala Val Leu
  1               5                  10                  15

Trp Leu Ala Met Val Ala Ala Phe Val Cys Ala Gly Leu Tyr Leu Arg
            20                  25                  30

Leu Thr Gly His Pro Pro Pro Pro Ser Glu Pro Arg Trp Phe Phe Leu
        35                  40                  45

Ile Pro Val Val Ser Gly Ala Ala Val Gly Leu Pro Val Ala Phe Ala
    50                  55                  60
```

```
Leu Ala Trp Tyr Leu Ala Lys Pro Leu His Leu Ser Met Ala Leu
 65                  70                  75                  80

Arg His Ala Ala Arg Ala Arg Phe Asp Val Arg Val Leu Pro Leu Leu
                 85                  90                  95

Gly Ser Arg Arg Asp Glu Leu Val Glu Leu Ala Arg Glu Phe Asp His
            100                 105                 110

Met Ala Ala Leu Leu Gln Gln Ala Ala Gln His Arg Gln Leu Phe
        115                 120                 125

His Asp Val Ser His Glu Leu Arg Ser Pro Leu Ala Arg Ile Gln Ala
    130                 135                 140

Ala Val Gly Leu Met Gln Gln Ser Pro Gln Ser Gly Pro Val Met Ala
145                 150                 155                 160

Glu Arg Ile Ala Arg Glu Ala Glu Arg Leu Asp Arg Leu Ile Glu Glu
                165                 170                 175

Leu Leu Thr Leu His Lys Leu Glu Ala Gly Ala Ile Gly Pro Val Arg
            180                 185                 190

Glu Arg Ile Asp Val Met Glu Leu Leu Ala Asp Ile Ala Gln Asp Ala
        195                 200                 205

Ala Phe Glu Ala Gln Ala Arg Ala Cys Ala Val Thr Leu Asp Ala Pro
    210                 215                 220

Gly Ser Phe Val Ala Glu Val Ala Gly Glu Thr Leu Tyr Arg Ala Phe
225                 230                 235                 240

Glu Asn Val Val Arg Asn Ala Val Lys Tyr Thr Ala Pro Asn Thr Thr
                245                 250                 255

Val Glu Ile His Ala Gln Val Ser Ala Pro Ala Thr Pro Gln Gly Gly
            260                 265                 270

Asp Val Lys Trp Leu Glu Val Ser Val Cys Asp Arg Gly Pro Gly Val
        275                 280                 285

Pro Ala Glu Phe Cys Glu Thr Ile Phe Glu Pro Phe Arg Arg Leu Glu
    290                 295                 300

Pro His Trp His Glu Gly Ala Ala Gln Ala Val Pro Gly Thr Gly Leu
305                 310                 315                 320

Gly Leu Ala Ile Ala Arg Arg Ala Leu Ala Leu His Gly Gly Ser Ile
                325                 330                 335

Arg Ala Val Pro Arg Glu Gly Gly Leu Arg Val Thr Ala Arg Leu
            340                 345                 350

Pro Ser Ala Val Met Ser Ala Pro Pro Ser Asp His Pro
355                 360                 365

<210> SEQ ID NO 125
<211> LENGTH: 342
<212> TYPE: PRT
<213> ORGANISM: Xenorhabdus nematophilus

<400> SEQUENCE: 125

Met Arg Arg Leu Trp Leu Ser Leu Cys Ala Leu Cys Pro Arg Pro Leu
  1               5                  10                  15

Ser Val Met Leu Ala Met Leu Leu Gly Ser Leu Leu Ile Ser Val Leu
                 20                  25                  30

Ile Ala Gln Leu Leu Thr Met Ile Glu Thr Leu Ser Phe Asp Ser Val
             35                  40                  45

Phe Pro Tyr Ile Phe Ile Ser Val Phe Ala Ala Ser Ser Leu Val Phe
         50                  55                  60

Ala Ala Phe Trp Arg Tyr Leu His Leu Gln Lys Gln Ser Leu Arg Ala
```

```
               65                  70                  75                  80
Met Gln Lys Ala Ala Leu Glu Met Gly Lys Gly Arg Thr Ala Ala Ser
                    85                  90                  95

Leu Pro Glu Thr Gly Thr Leu Thr Ile Arg Ala Leu Thr Gly Val Phe
            100                 105                 110

Asn Gln Met Ser Glu Arg Leu Lys Leu Gln Glu Asn Asp Gln Ala Val
            115                 120                 125

Leu Met Ala Gly Val Ser His Asp Leu Arg Thr Pro Leu Thr Arg Ile
    130                 135                 140

Arg Leu Ala Thr Glu Met Met Gln Gly Lys Asp Asn Phe Leu Ala Glu
145                 150                 155                 160

Ser Ile His Arg Asp Ile Glu Glu Cys Asn Ala Ile Ile Asp Gln Phe
                165                 170                 175

Ile Asp Tyr Gln Arg Ala Gly Gln Asn Met Pro Leu Thr Cys Cys Asp
            180                 185                 190

Leu Asn Glu Leu Leu Glu Ala Val Ile Glu Leu Glu Thr Val Ile Gly
            195                 200                 205

Ala Glu Gln His Gly Glu Val Asn Ile Glu His Cys Leu Ser Asp His
    210                 215                 220

Pro Ile Phe Ile Leu Ala Asn Pro Leu Ser Ile Lys Arg Ala Ile Ala
225                 230                 235                 240

Asn Met Phe Thr Asn Ala Gln Arg Tyr Gly Asn Gly Trp Ile Arg Ile
                245                 250                 255

Ser Ser Gly Thr Thr Glu Ala Phe Gly Trp Phe Gln Val Glu Asp Asp
            260                 265                 270

Gly Ser Gly Met Thr Lys Glu Glu Ala Asp Val Leu Phe Gln Pro Phe
            275                 280                 285

Thr Gln Gly Lys Arg Phe Arg His Val Arg His Asn Ser Gly Ala Gly
    290                 295                 300

Leu Gly Leu Ser Ile Ile Arg Arg Ile Ile Asp Ser His Glu Gly Tyr
305                 310                 315                 320

Ile Glu Val Arg Glu Ser Glu Lys Gly Gly Leu Ser Ile Arg Ala Cys
                325                 330                 335

Phe Pro Leu Asn Thr Lys
            340

<210> SEQ ID NO 126
<211> LENGTH: 319
<212> TYPE: PRT
<213> ORGANISM: Thermotoga maritima

<400> SEQUENCE: 126

Met Arg Val Ile Glu Leu Glu Asp Leu Asp His Ile Arg Glu Ala Ile
1               5                   10                  15

Val Ile Leu Lys Gly Leu Glu Val Glu Gly Ala Asn Lys Pro Gly Glu
                20                  25                  30

Lys Leu Gly Phe Lys Lys Gly Lys Asn Leu Met Ser Ile Phe Thr Cys
            35                  40                  45

Lys Glu Met Asp Arg Phe Ile Arg Asp Val Gln Glu Arg Lys Asn Phe
        50                  55                  60

Ser Leu Glu Thr Asn Ala Tyr Phe Phe Glu Leu His Ser Lys Arg Phe
65                  70                  75                  80

Val Ser Leu Arg Tyr Leu Pro Lys Lys Ser Leu Leu Phe Val Asn Asp
                85                  90                  95
```

-continued

```
Leu Thr Glu Glu Arg Thr Leu Ser Glu Ala Lys Leu Asp Phe Val Thr
            100                 105                 110

Ala Val Ser His Glu Leu Phe Thr Pro Leu Ser Ala Ser Lys Ala Asn
            115                 120                 125

Val Phe Leu Leu Lys Asp Ile Glu Asn Asp Pro Glu Lys Leu Glu Ile
    130                 135                 140

Leu Gly Lys Val Glu Arg Ser Leu Asp Arg Met Glu Thr Ile Ile Arg
145                 150                 155                 160

Gln Leu Lys Val Leu Thr Met Ile Gln Leu Arg Leu Tyr Glu Leu Lys
                165                 170                 175

Met Glu His Ile Pro Val Glu Glu Val Val His Met Val Leu Glu Glu
                180                 185                 190

Leu Arg Glu Lys Ile Glu Ser Lys Lys Ile Lys Val Asn Val Phe Val
            195                 200                 205

Asp Val Glu Thr Ile Glu Thr Asp Arg Phe Val Phe His Thr Ile Leu
    210                 215                 220

Lys Asn Leu Val Ser Asn Ala Val Lys Tyr Ser Tyr Pro Asp Ser Val
225                 230                 235                 240

Val Glu Ile Ser Ile Thr Gly Glu Arg Leu Ser Val Lys Asp Gln Gly
                245                 250                 255

Ile Gly Ile Lys Glu Glu Glu Lys Ser Arg Ile Phe Glu Arg Phe Tyr
            260                 265                 270

Arg Gly Ser Glu Ala Leu Lys Met Ala Pro Gly Ser Gly Leu Gly Leu
            275                 280                 285

Ser Ile Val Lys His Leu Cys Asp Thr Ile Gly Tyr Arg Leu Glu Val
    290                 295                 300

Asn Ser Gln Trp Leu Val Gly Ser Glu Phe Ile Val His Phe Lys
305                 310                 315
```